US012797133B2

(12) United States Patent
Metcalfe et al.

(10) Patent No.: US 12,797,133 B2
(45) Date of Patent: Nov. 17, 2026

(54) PREOPERATIVE SURGICAL PLANNING SYSTEMS AND METHODS USING SCAPULOTHORACIC JOINT KINEMATICS

(71) Applicant: ARTHREX, INC., Naples, FL (US)

(72) Inventors: Nick Metcalfe, Bonita Springs, FL (US); Sergii Poltaretskyi, Ependes (CH); Steven Jim DeLeon, Naples, FL (US); Siddhant Thakur, Naples, FL (US); David Knopf, Bonita Springs, FL (US); Philipp Moroder, Meilen (CH)

(73) Assignee: ARTHREX, INC., Naples, FL (US)

( * ) Notice: Subject to any disclaimer, the term of this patent is extended or adjusted under 35 U.S.C. 154(b) by 0 days.

(21) Appl. No.: 19/289,197

(22) Filed: Aug. 4, 2025

(65) Prior Publication Data

US 2026/0047890 A1 Feb. 19, 2026

Related U.S. Application Data

(60) Provisional application No. 63/683,295, filed on Aug. 15, 2024.

(51) Int. Cl.

| | |
|---|---|
| ***A61B 34/10*** | (2016.01) |
| ***A61F 2/46*** | (2006.01) |
| ***G16H 30/20*** | (2018.01) |

(52) U.S. Cl.

CPC ............ *A61B 34/10* (2016.02); *A61F 2/4612* (2013.01); *G16H 30/20* (2018.01); (Continued)

(58) Field of Classification Search

CPC .............. A61B 34/10; A61B 2034/105; A61B 2034/101; A61B 2034/104; (Continued)

(56) References Cited

U.S. PATENT DOCUMENTS

| | | | |
|---|---|---|---|
| 6,161,080 | A | 12/2000 | Aouni-Ateshian et al. |
| 6,205,411 | B1 | 3/2001 | DiGioia, III et al. |

(Continued)

FOREIGN PATENT DOCUMENTS

| | | | | |
|---|---|---|---|---|
| WO | WO-2015068035 A1 * | 5/2015 | ............. | A61B 34/10 |
| WO | 2018067966 A8 | 5/2018 | | |

(Continued)

OTHER PUBLICATIONS

Kim, YoungBeom, Byung-Ha Park, Kwang-Mo Jung and Junghyun Han. "Data-driven Shoulder Inverse Kinematics." International Journal of Computer Graphics & Animation (IJCGA) vol. 6, No. 4, Oct. 2016 (Year: 2016).*

(Continued)

*Primary Examiner* — Linh Giang Le

(74) *Attorney, Agent, or Firm* — Carlson, Gaskey & Olds, P.C.

(57) ABSTRACT

Improved surgical planning systems and methods are provided for planning orthopaedic procedures, including pre-operatively, intra-operatively, and/or post-operatively to create, edit, execute, and/or review surgical plans. The surgical planning systems and methods may be utilized for planning and implementing orthopaedic procedures to restore functionality to a joint. A scapulothoracic contribution to a range of motion may be determined. Range of motion simulations may be performed on a shoulder joint based on the scapulothoracic contribution.

20 Claims, 49 Drawing Sheets

(52) U.S. Cl.
CPC . *A61B 2034/105* (2016.02); *A61F 2002/4633* (2013.01); *A61F 2002/4668* (2013.01)

(58) Field of Classification Search
CPC ............. A61B 2034/108; A61F 2/4612; A61F 2002/4633; A61F 2002/4668; G16H 30/20
See application file for complete search history.

(56) References Cited

U.S. PATENT DOCUMENTS

| | | | | |
|---|---|---|---|---|
| 7,899,220 | B2 | 3/2011 | Haex et al. | |
| 8,831,302 | B2 | 9/2014 | Mahfouz | |
| 8,983,813 | B2 | 3/2015 | Miles et al. | |
| 9,101,394 | B2 | 8/2015 | Arata et al. | |
| 9,129,054 | B2 | 9/2015 | Nawana et al. | |
| 9,233,001 | B2 | 1/2016 | Miles et al. | |
| 9,271,848 | B2 | 3/2016 | Brooks | |
| 9,320,604 | B2 | 4/2016 | Miles et al. | |
| 9,408,698 | B2 | 8/2016 | Miles et al. | |
| 9,665,686 | B2 | 5/2017 | Van Vorhis et al. | |
| 9,700,292 | B2 | 7/2017 | Nawana et al. | |
| 9,717,508 | B2 | 8/2017 | Iannotti et al. | |
| 9,730,628 | B2 | 8/2017 | Iasemidis et al. | |
| 9,741,263 | B2 | 8/2017 | Iannotti et al. | |
| 9,827,051 | B2 | 11/2017 | Arata et al. | |
| 9,913,691 | B2 | 3/2018 | Brooks | |
| 9,913,692 | B2 | 3/2018 | Arata et al. | |
| 9,916,421 | B2 | 3/2018 | Vorhis et al. | |
| 10,130,378 | B2 | 11/2018 | Bryan | |
| 10,172,675 | B2 | 1/2019 | Mahfouz | |
| 10,327,852 | B2 | 6/2019 | Meridew et al. | |
| 10,449,003 | B2 | 10/2019 | Reid et al. | |
| 10,452,238 | B2 | 10/2019 | Nikou et al. | |
| 10,512,496 | B2 | 12/2019 | Iannotti et al. | |
| 10,537,390 | B2 | 1/2020 | Varadarajan et al. | |
| 10,595,943 | B2 | 3/2020 | Barsoum et al. | |
| 10,600,515 | B2 | 3/2020 | Otto et al. | |
| 10,621,384 | B2 | 4/2020 | Lemieux et al. | |
| 10,624,655 | B2 | 4/2020 | Iannotti et al. | |
| 10,660,705 | B2 | 5/2020 | Piron et al. | |
| 10,660,709 | B2 | 5/2020 | Chaoui | |
| 10,736,697 | B2 | 8/2020 | Chaoui et al. | |
| 10,739,963 | B2 | 8/2020 | Nikou et al. | |
| 10,973,580 | B2 | 4/2021 | Berend et al. | |
| 10,987,175 | B2 * | 4/2021 | Britton .................. | A61B 90/06 |
| 11,083,525 | B2 | 8/2021 | Varadarajan et al. | |
| 11,096,721 | B2 | 8/2021 | Theodore et al. | |
| 11,419,680 | B2 | 8/2022 | Kontaxis et al. | |
| 11,443,846 | B2 | 9/2022 | Schoenefeld et al. | |
| 11,464,569 | B2 | 10/2022 | Lambers et al. | |
| 11,478,168 | B2 | 10/2022 | Fleig et al. | |
| 11,488,721 | B2 | 11/2022 | Otto et al. | |
| 11,532,402 | B2 | 12/2022 | Farley et al. | |
| 11,839,550 | B1 | 12/2023 | Kellar et al. | |
| 12,086,998 | B2 | 9/2024 | Lang | |
| 12,133,688 | B2 | 11/2024 | Chaoui | |
| 12,150,714 | B2 | 11/2024 | Varadarajan et al. | |
| 12,178,517 | B2 | 12/2024 | Chaoui | |
| 2002/0009222 | A1 | 1/2002 | McGibbon et al. | |
| 2004/0102866 | A1 | 5/2004 | Harris et al. | |
| 2004/0233387 | A1 | 11/2004 | Huang et al. | |
| 2012/0276509 | A1 | 11/2012 | Iannotti et al. | |
| 2014/0013565 | A1 | 1/2014 | Macdonald et al. | |
| 2014/0257402 | A1 | 9/2014 | Barsoum | |
| 2014/0272881 | A1 | 9/2014 | Barsoum | |
| 2014/0278322 | A1 | 9/2014 | Jaramaz et al. | |
| 2014/0303990 | A1 | 10/2014 | Schoenefeld et al. | |
| 2015/0093734 | A1 | 4/2015 | Kaouk | |
| 2016/0278868 | A1 | 9/2016 | Berend et al. | |
| 2017/0296205 | A1 | 10/2017 | Iannotti et al. | |
| 2018/0033338 | A1 | 2/2018 | Iannotti et al. | |
| 2018/0233222 | A1 | 8/2018 | Daley et al. | |
| 2018/0358120 | A1 | 12/2018 | Schoenefeld et al. | |
| 2019/0005186 | A1 | 1/2019 | Nikou et al. | |
| 2019/0231431 | A1 | 8/2019 | Paszicsnyek | |
| 2019/0380792 | A1 | 12/2019 | Poltaretskyi et al. | |
| 2019/0388153 | A1 | 12/2019 | Running et al. | |
| 2020/0030034 | A1 | 1/2020 | Kontaxis et al. | |
| 2020/0113632 | A1 | 4/2020 | Varadarajan et al. | |
| 2020/0188026 | A1 | 6/2020 | De Souza et al. | |
| 2020/0205900 | A1 | 7/2020 | Buckland et al. | |
| 2020/0219626 | A1 | 7/2020 | Otto et al. | |
| 2020/0246075 | A1 | 8/2020 | Dohmen et al. | |
| 2020/0246077 | A1 | 8/2020 | Chaoui | |
| 2021/0000380 | A1 | 1/2021 | West et al. | |
| 2021/0093385 | A1 | 4/2021 | Morvan et al. | |
| 2021/0093391 | A1 | 4/2021 | Poltaretskyi et al. | |
| 2021/0093414 | A1 | 4/2021 | Moore et al. | |
| 2021/0100620 | A1 | 4/2021 | Chaoui et al. | |
| 2021/0104325 | A1 | 4/2021 | Chaoui et al. | |
| 2021/0210189 | A1 | 7/2021 | Casey et al. | |
| 2021/0307833 | A1 | 10/2021 | Farley et al. | |
| 2021/0315640 | A1 | 10/2021 | Dees, Jr. et al. | |
| 2021/0322148 | A1 | 10/2021 | Mitra et al. | |
| 2022/0039868 | A1 | 2/2022 | Chaoui et al. | |
| 2022/0047400 | A1 | 2/2022 | Chaoui et al. | |
| 2022/0059212 | A1 | 2/2022 | Chaoui et al. | |
| 2022/0059213 | A1 | 2/2022 | Chaoui et al. | |
| 2022/0117663 | A1 | 4/2022 | Mcguan et al. | |
| 2022/0117755 | A1 | 4/2022 | Mcguan et al. | |
| 2022/0156924 | A1 | 5/2022 | Poltaretskyi et al. | |
| 2022/0226044 | A1 | 7/2022 | Metcalfe et al. | |
| 2022/0273281 | A1 | 9/2022 | McKinnon et al. | |
| 2022/0287778 | A1 | 9/2022 | Bellettre et al. | |
| 2022/0370142 | A1 | 11/2022 | Schoenefeld et al. | |
| 2023/0048940 | A1 | 2/2023 | Kontaxis et al. | |
| 2023/0346480 | A1 | 11/2023 | Walch | |
| 2023/0390080 | A1 | 12/2023 | Cole et al. | |
| 2023/0390081 | A1 | 12/2023 | Cole et al. | |
| 2024/0050233 | A1 | 2/2024 | Kellar et al. | |
| 2025/0057599 | A1 | 2/2025 | Chaoui et al. | |
| 2025/0090235 | A1 | 3/2025 | Chaoui | |

FOREIGN PATENT DOCUMENTS

| | | | |
|---|---|---|---|
| WO | 2018107042 | A2 | 6/2018 |
| WO | 2019245849 | A1 | 12/2019 |
| WO | 2019245865 | A1 | 12/2019 |
| WO | 2019245854 | A3 | 2/2020 |
| WO | 2020033568 | A2 | 2/2020 |
| WO | 2020037308 | A1 | 2/2020 |
| WO | 2020072255 | A1 | 4/2020 |
| WO | 2020123706 | A1 | 6/2020 |
| WO | 2020163317 | A1 | 8/2020 |
| WO | 2020163318 | A1 | 8/2020 |
| WO | 2020163324 | A1 | 8/2020 |
| WO | 2020163352 | A1 | 8/2020 |
| WO | 2020163358 | A1 | 8/2020 |
| WO | 2021086687 | A1 | 5/2021 |
| WO | 2022066693 | A1 | 3/2022 |
| WO | 2022076773 | A1 | 4/2022 |
| WO | 2024039493 | A1 | 2/2024 |

OTHER PUBLICATIONS

Smith + Nephew launches CORIOGRAPH pre-op planning and modeling services for total shoulder arthroplasty. Retrieved from: https://www.smith-nephew.com/en/news/2025/10/01/01102025-coriograph-pre-op-planning-and-modeling-services-for-total-shoulder-arthroplasty.

International Search Report for International Application No. PCT/US2025/040454 mailed Dec. 22, 2025.

Alta, T.D.W., de Toledo, J.M., Veeger, H.E., Janssen, T.W.J., Willems, W.J. (2014). The active and passive kinematic difference between primary reverse and total shoulder prostheses. J Shoulder Elbow Surg (2014). pp. 1-8.

Borich, M.R., Bright, J.M., Lorello, D., Cieminski, C.J., Buisman, T., & Ludewig, P.M. (2006). Scapular angular positioning at end range internal rotation in cases of glenohumeral internal rotation deficit. Journal of Orthopaedic & Sports Physical Therapy. vol. 36(12). Dec. 2006. pp. 926-934.

(56) References Cited

OTHER PUBLICATIONS

Braman, J.P., Engel, S.C., LaPrade, R.F. & Ludewig, PT. (2009). J shoulder Elbow Surg. vol. 18(6). 2009. pp. 960-967.

De Baets, L., Van Deun, S., Desloovere, K., Jaspers, E. (2013). Dynamic scapular movement analysis: Is it feasible and reliable in stroke patients during arm elevation? PLoS One vol. 8(11). Nov. 2013. pp. 1-10.

International Preliminary Report on Patentability for International Application No. PCT/US2023/028524 mailed Feb. 27, 2025.

International Search Report & Written Opinion for International Application No. PCT/US2023/028549 mailed Jan. 4, 2024.

International Search Report and Written Opinion for International Application No. PCT/US2022/043287 dated Feb. 6, 2023.

International Search Report and Written Opinion for International Application No. PCT/US2023/028524 mailed Oct. 13, 2023.

Itoi, E., Morrey, B.F., & An, K-N. Biomechanics of the shoulder. Musculoskeletal Key. Chapter 6. Retrieved Jun. 21, 2023 from: https://musculoskeletalkey.com/biomechanics-of-the-shoulder/.

Karduna, A.R., McClure, P.W., Michener, L.A., & Sennett, B. (2001). Dynamic measurements of three-dimensional scapular kinematics: A validation study. Journal of Biomechanical Engineering. vol. 123. Apr. 2001. pp. 184-190.

Kozic, N. (2009). Statistical shape space analysis based on level sets for optimization of orthopaedic implant design. PhD Thesis. Graduate School for Cellular and Biomedical Sciences. University of Bern. Retrieved from: https://biblio.unibe.ch/download/eldiss/09kozic_n.pdf.

Kwon, Y.W., Pinto, V.J., Yoon, J., Frankle, M.A, Dunning, P.E. & Sheikhzadeh, A. (2012). J Shoulder Elbow Surg. vol. 21. 2012. pp. 1184-1190.

Kwon, Y.W., Pinto, V.J., Yoon, J., Frankle, M.A., Dunning, P.E., Sheikhzadeh, A. (2012). Kinematic analysis of dynamic shoulder motion in patients with reverse total shoulder arthoroplasty. J Shoulder Elbow Surg. vol. 21. pp. 1184-1190.

Lawrence, R.L., Braman, J.P., Laprade, R.F. & Ludewig, P.M. (2014). Comparison of 3-dimensional shoulder complex kinematics in individuals with an without shoulder pain, part 1: Sternoclavicular, acromioclavicular, and scapulothoracic joints. Journal of Orthopaedic & Sports Physical Therapy. vol. 44(9). Sep. 2014. pp. 636-645 and appendices.

Ludewig, P.M, Phadke, V., Braman, J.P., Hassett, D.R., Cieminski, C.J., & Laprade, R.F. (2009). Motion of the shoulder complex during multiplanar humeral elevation. J Bone Joint Surg Am. 2009. pp. 378-389.

McClure, P.W., Michener, L.A., Sennett, B.J., & Karduna, A.R. (2001). Direct 3-dimensional measurement of scapular kinematics during dynamic movements in vivo. J Shoulder Elbow Surg. vol. 10(3). May/Jun. 2021. pp. 269-277.

Moroder, P., Akgun, D., Plachel, F., Baur, A.D.J., Siegert, P. (2020). The influence of posture and scapulothoracic orientation on the choice of humeral component retrotorsion in reverse total shoulder arthroplasty. Journal of Shoulder and Elbow Surgery. vol. 29. pp. 1992-2001.

Moroder, P., MEng, MU., Raiss, P., Werthel, J-D., Akgun, D., Chaoui, J., Siegert, P. (2022). Patient posture affects simulated ROM in reverse total shoulder arthroplasty: A modeling study using preoperative planning software. Clin Orthop Relat Res (2022) 480:619-631.

Moroder, P., Urvoy, M., Raiss, P., Werthel, J-D., Akgun, D., Chaoui, J., Siegert, P. (2022). Patient posture affects simulated ROM in reverse total shoulder arthroplasty: A modeling study using preoperative planning software. Clincal Orthopaedics and Related Reserach. vol. 480(3). pp. 619-631.

Poltaretskyi, S., Chaoui, J., Mayya, M., Hamitouche, C., Bercik, M.J., Boileau, P., Walch, G. (2017). Prediction of the pre-morbid 3D anatomy of the proximal humerus based on statistical shape modelling. The Bone & Joint Journal. vol. 99-B(7). Jul. 2017. pp. 927-933.

Poppen, N.K. & Walker, P.S. (1976). Normal and abnormal motion of the shoulder. J Bone Join Surg Am. vol. 58-A(2). Mar. 1976. pp. 195-201.

Seth, A., Matias, R., Veloso, A.P., & Delp, S.L. (2016). A biomechanical model of the scapulothoracic joint to accurately capture scapular kinematics during shoulder movements. PLoS One vol. 11(1). Jan. 2016. pp. 1-18.

Simon, P., Diaz, M., Cusick, M., Santoni, B., and Frankle, M. (2018). 3D image-based morphometric analysis of the scapular neck length in subjects undergoing reverse shoulder arthroplasty. Clinical Anatomy. vol. 31(1). Jul. 27, 2017. pp. 43-55.

Steinhaus, M.E., Mclawhorn, A.S., Richardson, S., Maher, P., Mayman, D.J. (2016). Handheld navigation device and patient-specific cutting guides result in similar coronal alignment for primary total knee arthroplasty: A retrospective matched cohort study. HSS Journal. vol. 12(3). Feb. 29, 2016. pp. 224-234.

Von Eisenhart-Rothe , R., Jager, A., Englmeier, K-H., Vogl, T., Graichen, H. (2003). Pathomechanics in atraumatic shoulder instability—Correlation between scapular kinematics and humeral head position. 49th Annual Meeting of the Orthopaedic Research Society. Feb. 2-5, 2003.

Williams, Jr., G.R, Shakil, M., Klimkiewicz, J., & Iannotti, J.P. (1999). Anatomy of the scapulothoracic articulation. Clinical Orthopaedics and Related Research. No. 359. 1999. pp. 237-246.

Youtube. Scapulohumeral rhythm. Retrieved Jun. 21, 2023 from: https://www.youtube.com/watch?v=rpzBGIOEW4E.

Zdravkovic, V., Alexander, N., Wegener, R., Spross, C. & Jost, B. (2020). How do scapulothoracic kinematics during shoulder elevation differ between adults with and without rotator cuff arthropathy? Clin Orthop Relat Res vol. 478(11). 2020. pp. 2640-2649.

Zhao, K.D., Van Straaten, M.G., Cloud, B.A., Morrow, M.M., An, K-N & Ludewig, P.M. (2015). Scapulothoracic and glenohumeral kinematics during daily tasks in users of manual wheelchairs. Frontiers in Bioengineering and Biotechnology. vol. 3. Nov. 2015. pp. 1-10.

* cited by examiner

PREOPERATIVE SURGICAL PLANNING SYSTEMS AND METHODS USING SCAPULOTHORACIC JOINT KINEMATICS

CROSS-REFERENCE TO RELATED APPLICATIONS

This application claims the benefit of U.S. Provisional Application No. 63/683,295, filed Aug. 15, 2024, which is incorporated herein by reference in its entirety.

BACKGROUND

This disclosure is directed to surgical planning, and more particularly to improved surgical planning systems and methods for planning orthopedic procedures.

Arthroplasty is a type of orthopedic surgical procedure performed to repair or replace diseased joints. Surgeons may desire to establish a surgical plan for preparing a surgical site, selecting an implant, and placing the implant at the surgical site prior to performing arthroplasty in order to improve outcomes. Surgical planning may include capturing an image of the surgical site and determining a position of an implant based on the image.

SUMMARY

This disclosure relates to improved surgical planning systems and methods.

The surgical planning system and methods of this disclosure may be utilized in some implementations for planning orthopaedic procedures, including pre-operatively, intra-operatively, and/or post-operatively to create, edit, execute, and/or review surgical plans. The surgical planning systems and methods may be utilized for planning and implementing orthopaedic procedures to restore functionality to a joint.

A scapulothoracic contribution to a range of motion of a shoulder joint may be determined. A range of motion simulation may be performed on the shoulder joint based on the scapulothoracic contribution.

A surgical planning system for performing an orthopaedic procedure may include one or more processors operably coupled to memory. The memory may be configured to store a plurality of three-dimensional bone models associated with one or more bones. The plurality of bone models may include a humerus model, a scapula model, and a thorax model associated with a patient. The humerus model and the scapula model may be associated with a shoulder joint model. The scapula model and the thorax model may be associated with a scapulothoracic joint model. The one or more processors may be collectively operable to execute a planning environment. The planning environment may be operable to position at least one implant model relative to the shoulder joint model. The planning environment may be operable to determine an overall range of motion of the humerus model relative to one or more kinematic planes based on the position of the at least one implant model. The overall range of motion may be based on a humeroscapular contribution of humeroscapular movement between the humerus model and the scapula model and a scapulothoracic contribution of scapulothoracic movement between the scapula model and the thorax model. The planning environment may be operable to determine a numerical relationship between the humeroscapular contribution and the scapulothoracic contribution for at least one position relative to the overall range of motion. The planning environment may be operable to establish a surgical plan associated with the overall range of motion based on the numerical relationship.

A surgical planning system for performing an orthopaedic procedure may include one or more processors operably connected to memory. The memory may be operable to store a plurality of three-dimensional bone models associated with respective bones of a representative patient population. The plurality of bone models may include a first set associated with a scapula, a second set associated with a thorax, and a third set associated with a humerus. The one or more processors may be collectively operable to execute a planning environment. The planning environment may be operable to select a representative scapula model from the first set of the bone models in response to comparing the representative scapula model to a patient scapula model associated with the scapula of a patient. The representative scapula model may be associated with a representative thorax model of the second set of the bone models. The patient scapula model and a patient thorax model may establish a first spatial relationship. The representative scapula and thorax models may establish a second spatial relationship. The planning environment may be operable to determine a range of motion of a patient humerus model associated with a humerus of the patient model relative to one or more kinematic planes in response to comparing the first and second spatial relationships.

A computer implemented surgical planning method may include positioning a three-dimensional scapula model relative to a three-dimensional thorax model of a patient to establish a scapulothoracic joint model. The method may include positioning a three-dimensional humerus model relative to the scapula model to establish a shoulder joint model. The method may include positioning at least one implant model at a respective implant position relative to the shoulder joint model. the method may include determining an overall range of motion of the humerus model relative to one or more kinematic planes based on the position of the at least one implant model, including determining a humeroscapular contribution of humeroscapular movement between the humerus model and the scapula model and determining a scapulothoracic contribution of scapulothoracic movement between the scapula model and the thorax model. The method may include determining a numerical relationship between the humeroscapular contribution and the scapulothoracic contribution for at least one position relative to the overall range of motion. the method may include establishing a surgical plan associated with the shoulder joint model based on the determined numerical relationship.

The embodiments, examples, and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

BRIEF DESCRIPTION OF THE DRAWINGS

Like reference numbers and designations in the various drawings indicate like elements.

DETAILED DESCRIPTION

Figure 1:
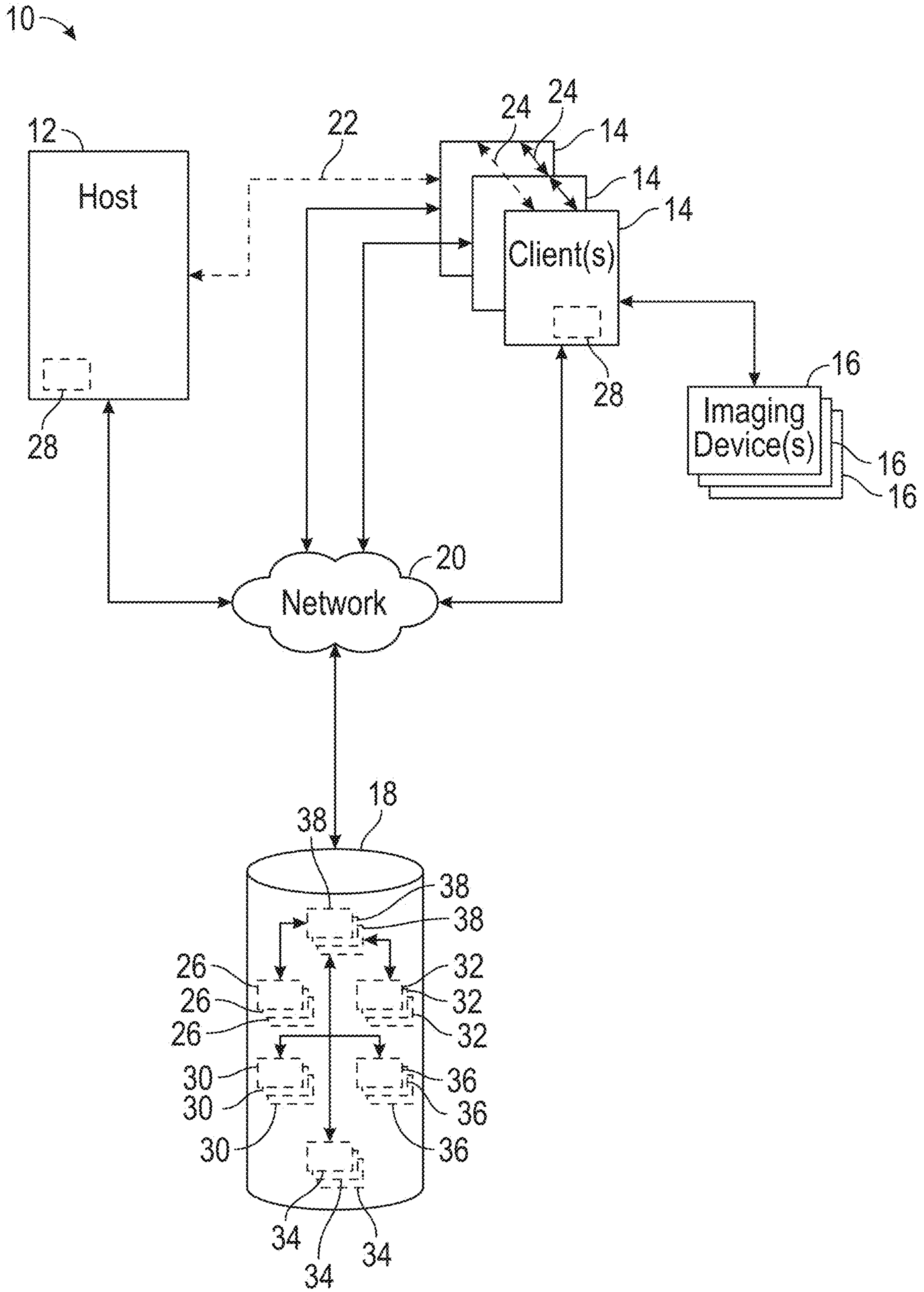
FIG. 1 discloses a surgical planning system according to an implementation.

This disclosure is directed to improved surgical planning systems and methods for planning orthopaedic procedures, including pre-operatively, intra-operatively, and/or post-operatively to create, edit, execute, and/or review surgical plans. The surgical planning systems and methods may be utilized for planning and implementing orthopaedic procedures to restore functionality to a joint. These and other features of this disclosure are discussed in greater detail in the following paragraphs of this detailed description.

A surgical planning system for performing an orthopaedic procedure may include one or more processors operably coupled to memory. The memory may be configured to store a plurality of three-dimensional bone models associated with one or more bones. The plurality of bone models may include a humerus model, a scapula model, and a thorax model associated with a patient. The humerus model and the scapula model may be associated with a shoulder joint model. The scapula model and the thorax model may be associated with a scapulothoracic joint model. The one or more processors may be collectively operable to execute a planning environment. The planning environment may be operable to position at least one implant model relative to the shoulder joint model. The planning environment may be operable to determine an overall range of motion of the humerus model relative to one or more kinematic planes based on the position of the at least one implant model. The overall range of motion may be based on a humeroscapular contribution of humeroscapular movement between the humerus model and the scapula model and a scapulothoracic contribution of scapulothoracic movement between the scapula model and the thorax model. The planning environment may be operable to determine a numerical relationship between the humeroscapular contribution and the scapulothoracic contribution for at least one position relative to the overall range of motion. The planning environment may be operable to establish a surgical plan associated with the overall range of motion based on the numerical relationship.

In any implementations, the planning environment may be operable to display the numerical relationship in a user interface.

In any implementations, the planning environment may be operable to receive image data associated with the patient. The planning environment may be operable to generate the scapula, thorax and humerus models based on the image data.

In any implementations, the numerical relationship may include a contribution ratio between the humeroscapular contribution and the scapulothoracic contribution. The planning environment may be operable to determine the contribution ratio for a set of positions relative to the overall range of motion. The set of positions may include a first position associated with commencement of the scapulothoracic contribution and a second position associated with a maximum limit relative to the overall range of motion. The contribution ratio associated with the first position may differ from the contribution ratio associated with the second position. The planning environment may be operable to display the contribution ratio for a/the set of positions relative to the overall range of motion. The planning environment may be operable to determine the scapulothoracic contribution based on a parametric relationship with respect to the humeroscapular contribution.

In any implementations, the parametric relationship may include a step function and/or a curve progression.

In any implementations, the planning environment may be operable to determine an amount of the scapulothoracic movement based on one or more posture parameters associated with a posture of the patient.

In any implementations, the one or more posture parameters may include a scapular angle associated with a scapula.

In any implementations, the one or more posture parameters may include a set of posture types. Each of the posture types may be associated with a discrete range of scapular angles.

In any implementations, the planning environment may be operable to determine the one or more posture parameters. The planning environment may be operable to receive the one or more posture parameters based on a user input.

In any implementations, the planning environment may be operable to determine a starting position of the humerus model and/or a starting position of the scapula model based on the one or more posture parameters. The planning environment may be operable to determine the humeroscapular contribution based on the starting position of the humerus model and/or determine the scapulothoracic contribution based on the starting position of the scapula model.

In any implementations, the three-dimensional bone models may include one or more bone models associated with one or more bones of a representative patient population. The planning environment may be operable to determine the scapulothoracic movement in response to comparing the scapula model and the thorax model of the patient to a representative scapula model and a representative thorax model of another patient of the representative patient population.

In any implementations, the planning environment may be operable to select the representative scapula model in response to analyzing the representative patient population within a statistical shape model.

In any implementations, the planning environment may be operable to adjust a position of the at least one implant model relative to the shoulder joint model based on a previously determined iteration of the overall range of motion.

In any implementations, the planning environment may be operable to determine an amount of the scapulothoracic movement based on one or more landmark characteristics associated with the humerus model, the scapula model, and/or the thorax model. The planning environment may be operable to assign the scapulothoracic contribution based on the determined amount of the scapulothoracic movement.

In any implementations, the one or more landmark characteristics may include an amount of lateralization of an acromion associated with the scapula model. The one or more landmark characteristics may include an amount of curvature of an angulus inferior associated with the scapula model. The one or more landmark characteristics may include a collapsed condition of the humerus model with respect to a premorbid boundary. The one or more landmark characteristics may include a broken gothic arch condition associated with a position of the humerus model relative to the scapula model.

In any implementations, the three-dimensional bone models may include one or more bone models associated with one or more bones of a/the representative patient population. The planning environment may be operable to determine the amount of curvature of the angulus inferior in response to comparing the scapula model of the patient to a/the representative scapula model of another patient of the representative patient population. The planning environment may be operable to determine the collapsed condition of the humerus model in response to comparing the humerus model of the patient to the premorbid boundary associated with a representative humerus model of another patient of the representative patient population.

In any implementations, the planning environment may be operable to select the representative scapula model in response to analyzing the representative patient population within a/the statistical shape model.

In any implementations, the planning environment may be operable to determine one or more soft tissue insertion points along the scapula model and/or the humerus model. The planning environment may be operable to determine an/the amount of the scapulothoracic movement based the one or more soft tissue insertion points.

A surgical planning system for performing an orthopaedic procedure may include one or more processors operably connected to memory. The memory may be operable to store a plurality of three-dimensional bone models associated with respective bones of a representative patient population. The plurality of bone models may include a first set associated with a scapula, a second set associated with a thorax, and a third set associated with a humerus. The one or more processors may be collectively operable to execute a planning environment. The planning environment may be operable to select a representative scapula model from the first set of the bone models in response to comparing the representative scapula model to a patient scapula model associated with the scapula of a patient. The representative scapula model may be associated with a representative thorax model of the second set of the bone models. The patient scapula model and a patient thorax model may establish a first spatial relationship. The representative scapula and thorax models may establish a second spatial relationship. The planning environment may be operable to determine a range of motion of a patient humerus model associated with a humerus of the patient model relative to one or more kinematic planes in response to comparing the first and second spatial relationships.

In any implementations, the planning environment may be operable to position at least one implant model relative to the patient scapula model and/or the patient humerus model. The planning environment may be operable to determine the range of motion of the humerus model based on the position of the at least one implant model.

In any implementations, the range of motion may be an overall range of motion of the patient humerus model relative to the one or more kinematic planes. The planning environment may be operable to determine the overall range of motion based on a humeroscapular contribution of humeroscapular movement between the patient humerus model and the patient scapula model and a scapulothoracic contribution of scapulothoracic movement between the patient scapula model and the patient thorax model. The planning environment may be operable to determine a numerical relationship between the humeroscapular contribution and the scapulothoracic contribution for at least one position relative to the overall range of motion.

In any implementations, the planning environment may be operable to display the numerical relationship in a user interface.

In any implementations, the planning environment may be operable to select the representative scapula model in response to analyzing the representative patient population within a statistical shape model.

In any implementations, the planning environment may be operable to create a plurality of anatomical makeup classifications based on a plurality of predefined modes within the statistical shape model that characterize anatomical differences within the representative patient population and a plurality of standard deviations of anatomical variances contained within each of the plurality of predefined modes. The planning environment may be operable to assign the anatomical makeup classifications to the bone models. The memory may be operable to store the anatomical makeup classifications.

In any implementations, the planning environment may be operable to select the representative scapula model in response to varying one or more of the predefined modes.

In any implementations, the planning environment may be operable to assign the anatomical makeup classification associated with the representative scapula model to the patient scapula model and/or assign the anatomical makeup classification associated with the representative thorax model to the patient thorax model. The planning environment may be operable to determine the range of motion in response to performing a range of motion simulation for the assigned anatomical makeup classification.

In any implementations, the predefined modes may include a posture mode associated with posture. The planning environment may be operable to assign the anatomical makeup classifications to the bone models based on the posture mode. The planning environment may be operable to determine one or more posture parameters associated with a posture of the patient based on the anatomical makeup classification associated with the representative scapula model and/or the representative thorax model. The planning environment may be operable to determine the range of motion based on the one or more posture parameters.

In any implementations, the one or more posture parameters may include a scapular angle associated with a scapula.

In any implementations, the one or more posture parameters may include a set of posture types. Each of the posture types may be associated with a discrete range of scapular angles of a scapula.

In any implementations, the planning environment may be operable to determine a starting position of the patient humerus model and/or a starting position of the patient scapula model based on the one or more posture parameters. The planning environment may be operable to determine a/the humeroscapular contribution associated with the range of motion based on the starting position of the patient humerus model and/or determine a/the scapulothoracic contribution associated with the range of motion based on the starting position of the patient scapula model.

In any implementations, the planning environment may be operable to perform a range of motion simulation based on the one or more posture parameters and/or the assigned anatomical makeup classification.

A computer implemented surgical planning method may include positioning a three-dimensional scapula model relative to a three-dimensional thorax model of a patient to establish a scapulothoracic joint model. The method may include positioning a three-dimensional humerus model relative to the scapula model to establish a shoulder joint model. The method may include positioning at least one implant model at a respective implant position relative to the shoulder joint model. the method may include determining an overall range of motion of the humerus model relative to one or more kinematic planes based on the position of the at least one implant model, including determining a humeroscapular contribution of humeroscapular movement between the humerus model and the scapula model and determining a scapulothoracic contribution of scapulothoracic movement between the scapula model and the thorax model. The method may include determining a numerical relationship between the humeroscapular contribution and the scapulothoracic contribution for at least one position relative to the overall range of motion. the method may include establishing a surgical plan associated with the shoulder joint model based on the determined numerical relationship.

In any implementations, the method may include displaying the numerical relationship in a user interface.

In any implementations, the surgical plan may include a plurality of implant parameters. The implant parameters may include an implant type, an implant dimension and/or the implant position. The method may include determining the overall range of motion in response to setting the implant parameters. The method may include establishing the surgical plan based on the implant parameters.

In any implementations, the step of determining the scapulothoracic movement may include comparing the scapula model and the thorax model of the patient to a three-dimensional representative scapula model and a three-dimensional representative thorax model of another patient of a representative patient population.

In any implementations, the method may include selecting the representative scapula model and/or the representative thorax model in response to analyzing the representative patient population within a statistical shape model.

In any implementations, the step of determining the humeroscapular contribution and/or the scapulothoracic contribution may include determining one or more posture parameters associated with a posture of the patient.

In any implementations, the step of determining the humeroscapular contribution and/or the step of determining the scapulothoracic contribution may include performing a range of motion simulation of the humerus model in the one or more kinematic planes based on the one or more posture parameters.

In any implementations, the method may include determining the scapulothoracic contribution based on one or more landmark characteristics associated with the humerus model, the scapula model and/or the thorax model of the patient.

In any implementations, the method may include determining the one or more landmark characteristics. Determining the one or more landmark characteristics may include determining an amount of lateralization of an acromion associated with the scapula model. Determining the one or more landmark characteristics may include determining an amount of curvature of an angulus inferior associated with the scapula model. Determining the one or more landmark characteristics may include determining a collapsed condition of the humerus model with respect to a premorbid boundary. Determining the one or more landmark characteristics may include determining a broken gothic arch condition associated with a position of the humerus model relative to the scapula model.

FIG. 1 discloses a surgical planning system 10. The system 10 may be used for planning orthopaedic procedures, including pre-operatively, intra-operatively, and/or post-operatively to create, edit, review, refine, and/or execute surgical plans. The system 10 may be utilized for various orthopaedic and other surgical procedures, such as an arthroplasty to repair a joint.

Shoulder arthroplasty may be periodically referenced throughout this disclosure to illustrate or emphasize certain features of the system 10. However, the teachings of this disclosure are not intended to be limited to any particular joint of the human musculoskeletal system and should therefore be understood as being applicable to the shoulder, knee, hip, ankle, wrist, etc. Moreover, the teachings of this disclosure are not intended to be limited to arthroplasty procedures and are therefore applicable to the repair of fractures and/or other deformities within the scope of this disclosure.

The system 10 may include, among other things, at least one host computer 12, one or more client computers 14, one or more imaging devices 16, a cloud-based storage system 18, and a network 20. The system 10 may include a greater or fewer number of subsystems within the scope of this disclosure.

The host computer 12 may be configured to execute one or more software programs. In some implementations, the host computer 12 may be more than one computer jointly configured to process software instructions serially or in parallel.

The host computer 12 may be in communication with the network 20, which itself may include one or more computing devices. The network 20 may be a private local area network (LAN), a private wide area network (WAN), the Internet, or a mesh network, for example.

The host computer 12 and each client computer 14 may include one or more of a computer processor, memory, storage means, network device and input and/or output devices and/or interfaces. The input devices may include a keyboard, mouse, etc. The output devices may include a monitor, speakers, printers, etc. The memory may, for example, include UVPROM, EEPROM, FLASH, RAM, ROM, DVD, CD, a hard drive, or other computer readable medium that may store data and/or other information relating to the surgical planning and implementation techniques disclosed herein. The host computer 12 and each client computer 14 may be a desktop computer, laptop computer, smart phone, tablet, virtual machine, or any other computing device. The interfaces may facilitate communication with the other systems and/or components of the network 20.

Each client computer 14 may be configured to communicate with the host computer 12 either directly, such as via a direct client interface 22, or over the network 20. In other implementations, the client computers 14 are configured to communicate with each other directly via a peer-to-peer interface 24.

Each client computer 14 may be coupled to one or more of the imaging devices 16. Each imaging device 16 may be configured to capture or acquire one or more images 26 of patient anatomy residing within a scan field (e.g., window) of the imaging device 16. The imaging device 16 may be configured to capture or acquire two dimensional (2D) and/or three dimensional (3D) greyscale and/or color images 26. Various imaging devices 16 may be utilized, including but not limited to an X-ray machine, a computerized tomography (CT) machine, or a magnetic resonance imaging (MRI) machine, for obtaining one or more images 26 of a patient.

The client computers 14 may also be configured to execute one or more software programs, such as those associated with various surgical planning tools. Each client computer 14 may be operable to access and locally and/or remotely execute a planning environment 28 for creating, editing, executing, refining, and/or reviewing one or more surgical plans 36 during pre-operative, intra-operative and/or post-operative phases of a surgery. The planning environment 28 may be a standalone software package or may be incorporated into another surgical tool. The planning environment 28 may be configured to communicate with the host computer 12 either over the network 20 or directly through the direct client interface 22.

The planning environment 28 may be further configured to interact with one or more of the imaging devices 16 to capture or acquire images 26 of patient anatomy. The planning environment 28 may provide a display or visualization of one or more images 26, bone models 30, implant models 32, transfer models 34, and/or surgical plans 36 via one or more graphical user interfaces (GUI). Each image 26, bone model 30, implant model 32, transfer model 34, surgical plan 36, and other data and/or information may be stored in one or more files or records according to a specified data structure.

The planning environment 28 may include various modules for performing the desired planning functions. For example, as further discussed below, the planning environment 28 may include a data module for accessing, retrieving, and/or storing data concerning the surgical plans 36, a display module for displaying the data (e.g., within one or more GUIs), a spatial module for modifying the data displayed by the display module, and a comparison module for determining one or more relationships between selected bone models and selected implant models. However, a greater or fewer number of modules may be utilized, and/or one or more of the modules may be combined to provide the disclosed functionality.

The storage system 18 may be operable to store or otherwise provide data from/to other computing devices, such as the host computer 12 and/or the one or more client computers 14, of the system 10. The storage system 18 may be a storage area network device (SAN) configured to communicate with the host computer 12 and/or the client computers 14 over the network 20, for example. Although shown as a separate device of the system 10, the storage system 18 may in some implementations be incorporated within or directly coupled to the host computer 12 and/or client computers 14. The storage system 18 may be configured to store one or more of computer software instructions, data, database files, configuration information, etc.

In some implementations, the system 10 may be a client-server architecture configured to execute computer software on the host computer 12, which may be accessible by the client computers 14 using either a thin client application or a web browser that can be executed on the client computers 14. The host computer 12 may load the computer software instructions from local storage, or from the storage system 18, into memory and may execute the computer software using the one or more computer processors.

The system 10 may further include one or more databases 38. The databases 38 may be stored at a central location, such as on the storage system 18. In another implementation, one or more databases 38 may be stored at the host computer 12 and/or may be a distributed database provided by one or more of the client computers 14. Each database 38 may be a relational database configured to associate one or more images 26, bone models 30, implant models 32, and/or transfer models 34 to each other and/or to a respective surgical plan 36. Each surgical plan 36 may be associated with the anatomy of a respective patient. Each image 26, bone model 30, implant model 32, transfer model 34, and surgical plan 36 may be assigned a unique identifier or database entry for storage on the storage system 18. Each database 38 may be configured to store data and other information corresponding to the images 26, bone models 30, implant models 32, transfer models 34, and surgical plans 36 in one or more database records or entries, and/or may be configured to link or otherwise associate one or more files corresponding to each respective image 26, bone model 30, implant model 32, transfer model 34, and surgical plan 36. The various data stored in the database(s) 38 may correspond to respective patient anatomies from prior surgical cases, and may be arranged into one or more predefined categories such as sex, age, ethnicity, defect category, procedure type, anatomical makeup classification, surgeon, facility or organization, etc.

Each image 26 and bone model 30 may include data and other information obtained from one or more medical devices or tools, such as the imaging devices 16. The bone models 30 may include one or more digital images and/or coordinate information relating to an anatomy of the patient obtained or derived from image(s) 26 captured or otherwise obtained by the imaging device(s) 16.

Each implant model 32 and transfer model 34 may include coordinate information associated with a predefined design or a design established or modified by the planning environment 28. The predefined design may correspond to one or more components. The planning environment 28 may incorporate and/or interface with one or more modeling packages, such as a computer aided design (CAD) package, to render the models 30, 32, and 34 as two-dimensional (2D) and/or three-dimensional (3D) volumes or constructs, which may overlay one or more of the images 26 in a display screen of a GUI.

The implant models 32 may correspond to implants and components of various shapes and sizes. Each implant may include one or more components that may be situated at a surgical site including screws, anchors, grafts, etc. Each implant model 32 may correspond to a single component or may include two or more components that may be configured to establish an assembly. Each implant and associated component(s) may be formed of various materials, including metallic and/or non-metallic materials. Each bone model 30, implant model 32, and transfer model 34 may correspond to 2D and/or 3D geometry, and may be utilized to generate a wireframe, mesh, and/or solid construct in a GUI.

Each surgical plan 36 may be associated with one or more of the images 26, bone models 30, implant models 32, and/or transfer models 34. The surgical plan 36 may include various parameters associated with the images 26, bone models 30, implant models 32, and/or transfer models 34. For example, the surgical plan 36 may include parameters relating to bone density and bone quality associated with patient anatomy captured in the image(s) 26. The surgical plan 36 may include parameters including spatial information relating to relative positioning and coordinate information of the selected bone model(s) 30, implant model(s) 32, and/or transfer model(s) 34.

The surgical plan 36 may define one or more revisions to a bone model 30 and information relating to a position of an implant model 32 and/or transfer model 34 relative to the original and/or revised bone model 30. The surgical plan 36 may include coordinate information relating to the revised bone model 30 and a relative position of the implant model 32 and/or transfer model 34 in one or more predefined data structure(s). The planning environment 28 may be configured to implement one or more revisions to the various models, either automatically or in response to user interaction with the user interface(s). Revisions to each bone model 30, implant model 32, transfer model 34, and/or surgical plan 36 may be stored in one or more of the databases 38, either automatically and/or in response to user interaction with the system 10.

One or more surgeons and/or other staff users may be presented with the planning environment 28 via the client computers 14 and may simultaneously access each image 26, bone model 30, implant model 32, transfer model 34, and surgical plan 36 stored in the database(s) 38. Each user may interact with the planning environment 28 to create, view, refine, and/or modify various aspects of the surgical plan 36. Each client computer 14 may be configured to store local instances of the images 26, bone models 30, implant models 32, transfer models 34, and/or surgical plans 36, which may be synchronized in real-time or periodically with the database(s) 38. The planning environment 28 may be a standalone software package executed on a client computer 14 or may be provided as one or more web-based services executed on the host computer 12, for example.

The system 10 described above may be configured for preoperatively planning surgical procedures. The preoperative planning provided by the system 10 may include, but is not limited to, features such as constructing a virtual model of a patient's anatomy, classifying the virtual model, identifying landmarks within the virtual model, selecting and orienting virtual implants within the virtual model, etc.

Figure 2:
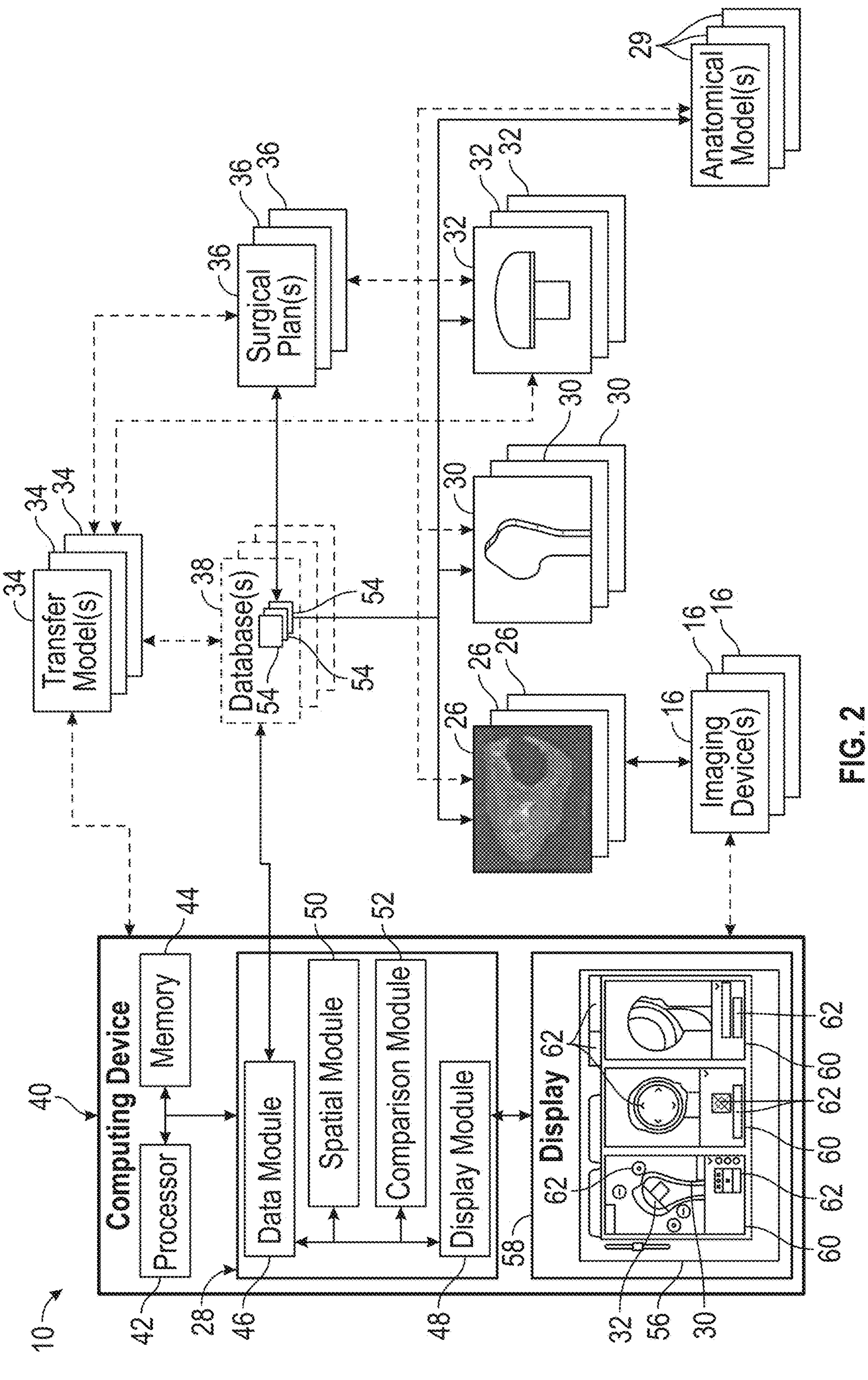
FIG. 2 discloses aspects of the surgical planning system of FIG. 1 according to an implementation.

Referring now to FIG. 2, with continuing reference to FIG. 1, the system 10 may include a computing device 40 including at least one or more processors 42 operably coupled to memory 44 capable of storing computer executable instructions. The computing device 40 may be considered representative of any of the computing devices disclosed herein, including but not limited to the host computer 12 and/or the client computers 14. The one or more processors 42 may be collectively configured (e.g., operable) to execute one or more of the planning environments 28. The planning environment 28 may be operable to create, edit, execute, refine, and/or review one or more surgical plans 36 and any associated bone models 30, implant models 32, and transfer models 34 during pre-operative, intra-operative, and/or post-operative phases of a surgery.

The processor 42 can be a custom made or commercially available processor, central processing unit (CPU), or generally any device for executing software instructions. The memory 44 can include any one or combination of volatile memory elements and/or nonvolatile memory elements. The processor 42 may be operably coupled to the memory 44 and may be configured to execute one or more programs stored in the memory 44 based on various inputs received from other devices or data sources.

The planning environment 28 may include at least a data module 46, a display module 48, a spatial module 50, and a comparison module 52. Although four modules are shown, it should be understood that a greater or fewer number of modules could be utilized, and/or further that one or more of the modules could be combined to provide the disclosed functionality.

The data module 46 may be configured to access, retrieve, and/or store data and other information in the database(s) 38 corresponding to one or more images 26 of patient anatomy, bone model(s) 30, implant model(s) 32, transfer model(s) 34, and/or surgical plan(s) 36. The data and other information may be stored in one or more databases 38 as one or more records or entries 54. In some implementations, the data and other information may be stored in one or more files that are accessible by referencing one or more objects or memory locations referenced by the entries 54.

The memory 44 may be configured to access, load, edit, and/or store instances of one or more images 26, bone models 30, implant models 32, transfer models 34, and/or surgical plans 36 in response to one or more commands from the data module 46. The data module 46 may be configured to cause the memory 44 to store a local instance of the image(s) 26, bone model(s) 30, implant model(s) 32, transfer model(s) 34, and/or surgical plan(s) 36, which may be synchronized with the entries 54 stored in the database(s) 38.

The data module 46 may be configured to receive data and other information corresponding to at least one or more images 26 of patient anatomy from various sources, such as the imaging device(s) 16, for example. The data module 46 may be further configured to command the imaging device 16 to capture or acquire the images 26 automatically or in response to user interaction.

The display module 48 may be configured to display data and other information relating to one or more surgical plans 36 in at least one graphical user interface (GUI) 56, including one or more of the images 26, bone models 30, implant models 32, and/or transfer models 34. The computing device 40 may incorporate or be coupled to a display device 58. The display module 48 may be configured to allow the display device 58 to display information in the user interface 56. A surgeon or other user may interact with the user interface 56 within the planning environment 28 to view one or more images 26 of patient anatomy and/or any associated bone models 30, implant models 32, and transfer models 34. The surgeon or other user may interact with the user interface 56 via the planning environment 28 to create, edit, execute, refine, and/or review one or more surgical plans 36.

The user interface 56 may include one or more display windows 60 and one or more objects 62 that may be presented within the display windows 60. The display windows 60 may include any number of windows, and the objects 62 may include any number of objects within the scope of this disclosure.

A surgeon or user may interact with the user interface 56, including the objects 62 and/or display windows 60, to retrieve, view, edit, store, etc., various aspects of a respective surgical plan 36, which may include information from the selected image(s) 26, bone model(s) 30, implant model(s) 32 and/or transfer model(s) 34. The objects 62 may include graphics such as menus, tabs, buttons, drop-down lists, directional indicators, etc. The objects 62 may be organized in one or more menu items associated with the respective display windows 60. Geometric objects, including selected image(s) 26, bone model(s) 30, implant model(s) 32, transfer model(s) 34, and/or other information relating to the surgical plan 36, may be displayed in one or more of the display windows 60. Each transfer model 34 may include one or more surgical instruments used to implant a selected implant as part of the surgical plan 36.

The surgeon may interact with the objects 62 to specify various aspects of the surgical plan 36. For example, the surgeon may select one of the tabs to view or specify aspects of the surgical plan 36 for one portion of a joint, such as a glenoid, for example, and may select another one of the tabs to view or specify aspects of the surgical plan 36 for another portion of the joint, such as a humerus, for example. The surgeon may take various measurements (e.g., linear, angular, tissue density, etc.) of the joint as part specifying aspects of the surgical plan 36.

The surgeon may interact with the menu items to select and specify various aspects of the bone models 30, implant models 32, and/or transfer models 34 from the database 38. For example, the display module 48 may be configured to display one or more bone models 30 together with the respective image(s) 26 of the patient anatomy and implant models 32 selected in response to user interaction with the user interface 56. The user may interact with the drop-down lists of the objects 62 within the display windows 60 to specify implant type, resection angle, and implant size. The resection angle menu item may be further associated with a resection plane.

The user may also interact with various buttons to change (e.g., increase or decrease) a resection angle. The user may interact with buttons adjacent the selected implant model 32 to change (e.g., increase or decrease) a size of a component of the selected implant model 32. The buttons may be overlaid onto or may be situated adjacent to the display windows 60.

The user may further interact with directional indicators to move a portion of the selected implant model 32 in different directions (e.g., up, down, left, right) in one of the display windows 60. The surgeon may drag or otherwise move the selected implant model 32 to a desired position in the display window 60 utilizing a mouse or other input device, for example. The surgeon may interact with one of the drop-down lists to specify a type and/or size of a component of the selected implant model 32.

The display module 48 may be configured to superimpose one or more of the bone models 30, the implant models 32, and the transfer models 34 over one or more of the images 26 within one or more of the display windows 60. The implant model 32 may include one or more components that establish an assembly. At least a portion of the implant model 32 may be configured to be at least partially received in a volume of a selected one of the bone models 30. In some implementations, the implant model 32 may have an articulation surface dimensioned to mate with an articular surface of an opposed bone or implant.

The display windows 60 may be configured to display the images 26, bone models 30, implant models 32, and/or transfer models 34 at various orientations. The display module 48 may be configured to display two dimensional (2D) representation(s) of the selected bone model(s) 30, implant model(s) 32, and/or transfer model(s) 34 in the some of the display windows 60, and may be configured to display 3D representation(s) of the selected bone model 30, implant model 32, and/or transfer model(s) 34 in another of the display windows 60, for example. The surgeon may interact with the user interface 56 to move (e.g., up, down, left, right, rotate, etc.) the selected bone model 30, selected implant model 32, and/or selected transfer model 34 in 2D space and/or 3D space. Other implementations for displaying 2D and/or 3D representations in the various display windows 60 are further contemplated within the scope of this disclosure.

The display module 48 may be further configured such that the selected image(s) 26, bone model(s) 30, implant model(s) 32, and/or transfer model(s) 34 may be selectively displayed and hidden (e.g., toggled) in one or more of the display windows 60 in response to user interaction with the user interface 56, which may provide the surgeon with enhanced flexibility in reviewing aspects of the surgical plan 36. For example, the surgeon may interact with drop-down lists of the objects 62 to selectively display and hide components of the selected implant model 32 in one of the display windows 60.

The selected bone model 30 may correspond to a bone associated with a joint, including any of the exemplary joints disclosed herein. The display module 48 may be configured to display a sectional view of the selected bone model 30 and selected implant model 32 in one or more of the display windows 60, for example. The sectional view of the bone model(s) 30 may be presented or displayed together with the associated image(s) 26 of the patient anatomy.

The spatial module 50 may be configured to establish one or more resection planes along the selected bone model 30. A volume of the selected implant model 32 may be at least partially received in a volume of the selected bone model 30 along the resection plane(s). The resection plane(s) may be defined by a resection angle.

The spatial module 50 may be further configured to cause the display module 48 to display an excised portion of the selected bone model 30 to be displayed in one of the display windows 60 in a different manner than a remainder of the bone model 30 on an opposed side of the resection plane. For example, the excised portion of the bone model 30 may be hidden from display in the display window 60 such that the respective portion of the 26 of the patient anatomy is shown. In other implementations, the excised portion of the selected bone model 30 may be displayed in a relatively darker shade. The spatial module 50 may determine the excised portion by comparing coordinates of the bone model 30 with respect to a position of the resection plane, for example. The user may interact with one or more buttons of the objects 62 to toggle between a volume of previous and revised (e.g., resected) states of the selected bone model 30.

The planning environment 28 may be further configured such that changes in one of the display windows 60 are synchronized with each of the other windows 60. The changes may be synchronized between the display windows 60 automatically and/or manually in response to user interaction.

The surgeon may utilize various instrumentation and devices to implement each surgical plan 36, including preparing the surgical site and securing one or more implants to bone or other tissue to restore functionality to the respective joint. Each of the transfer models 34 may be associated with a respective surgical instrument or device (e.g., transfer guides, etc.) or a respective implant model 32.

The surgical plan 36 may be associated with one or more positioning objects such as a guide pin (e.g., guide wire or Kirschner wire) dimensioned to be secured in tissue to position and orient the various instrumentation, devices and/or implants. The display module 48 may be configured to display a virtual position and virtual axis in one or more of the display windows 60. The virtual position may be associated with a specified position of the positioning object relative to the patient anatomy (as represented by the image (s) 26). The virtual axis may extend through the virtual position and may be associated with a specified orientation of the positioning object relative to the patient anatomy. The spatial module 50 may be configured to set the virtual position and/or virtual axis in response to placement of a respective implant model 32 relative to the bone model 30 and associated patient anatomy. The virtual position and/or virtual axis may be set and/or adjusted automatically based on a position and orientation of the selected implant model 32 relative to the selected bone model 30 and/or in response to user interaction with the user interface 56.

The spatial module 50 may be further configured to determine one or more collision or contact points associated with the patient anatomy. The contact points may be associated with one or more landmarks or other surface features along the bone model 30 and/or other portions of the patient anatomy. Each contact point may be established along an articular surface or non-articular surface of a joint. The spatial module 50 may be configured to set the contact points based on the virtual position, virtual axis, and/or position and orientation of the respective implant model 32 relative to the patient anatomy. The spatial module 50 may be configured to cause the display module 48 to display the contact points in one or more of the display windows 60. In some implementations, the contact points may be set and/or adjusted automatically based on a position of the implant model 32 and/or in response to user interaction with the user interface 56. The virtual position, virtual axis, and/or contact points may be stored in one or more entries 54 in the database 38 and may be associated with the respective surgical plan 36.

The comparison module 52 may be configured to generate or set one or more parameters associated with implementing the surgical plan 36. The parameters may include one or more settings or dimensions associated with the respective transfer models 34. The parameters may be based on the virtual position, virtual axis, and/or contact points. The comparison module 52 may be configured to determine one or more settings or dimensions associated with the respective transfer models 34 relative to the patient anatomy, bone model(s) 30, implant model(s) 32, virtual position, virtual axis, and/or contact points CP. The dimensions and settings may be utilized to form a physical instance of each respective transfer model 34. The settings may be utilized to specify a position and orientation of each respective transfer model 34 relative to the implant model 32 and/or bone model 30. The settings may be utilized to configure one or more transfer members (e.g., objects) and related instrumentation or devices associated with the transfer model 34. The comparison module 52 may be configured to generate the settings and/or dimensions such that the transfer model 34 contacts one or more predetermined positions at or along the bone model 30 or patient anatomy in an installed position when coupled to the respective implant model 32. The predetermined positions may include one or more of the contact points. The settings and dimensions may be communicated utilizing various techniques, including one or more graphics in the user interface 56 or output files. The settings and/or dimensions may be stored in one or more entries 54 in the database 38 associated with the transfer models 34.

The user may interact with a list of the objects 62 associated with one of the display windows 60 to select a desired transfer model 34 from the database 38. The display module 48 may be configured to display the selected transfer model 34 in the display windows 60 at various positions and orientations. The spatial module 50 may be configured to set an initial position of the selected transfer model 34 according to the virtual position, virtual axis, and/or contact points.

The user may interact with the user interface 56 to set or adjust a position and/or orientation of the selected transfer model 34. The user may interact with directional indicators of the objects 62 to move the selected transfer model 34 and/or virtual position in different directions (e.g., up, down, left, right) in the display windows 60. The surgeon may drag or otherwise move the selected transfer model 34 and/or virtual position to a desired position in the display windows 60 utilizing a mouse or other input device, for example. The user may interact with rotational indicators of the objects to adjust a position and/or orientation of the transfer model 34 about the virtual axis relative to the selected bone model 30 and/or implant model 32. The user may interact with tilt indicators of the objects 62 to adjust an orientation of the selected transfer model 34 and associated virtual axis at the virtual position relative to the selected bone model 30 and/or implant model 32. The user may interact with other buttons and/or directional indicators to cause the transfer model 34 to articulate or otherwise move. The transfer model 34 may be articulated or otherwise moved independently or synchronously, which may occur manually in response to user interaction and/or automatically in response to situating the transfer model 34 relative to the bone model 30 and/or implant model 32. Movement of the transfer model 34 may cause an automatic adjustment to the respective contact points.

Various transfer members may be utilized with the planning environment 28 to implement the surgical plan(s) 36. Each transfer member may be associated with a respective transfer model 34. The transfer members may be incorporated into transfer guides, implants, and/or assemblies to set a position and orientation of the respective implant prior to fixing or otherwise securing the implant at a surgical site.

Figure 3:
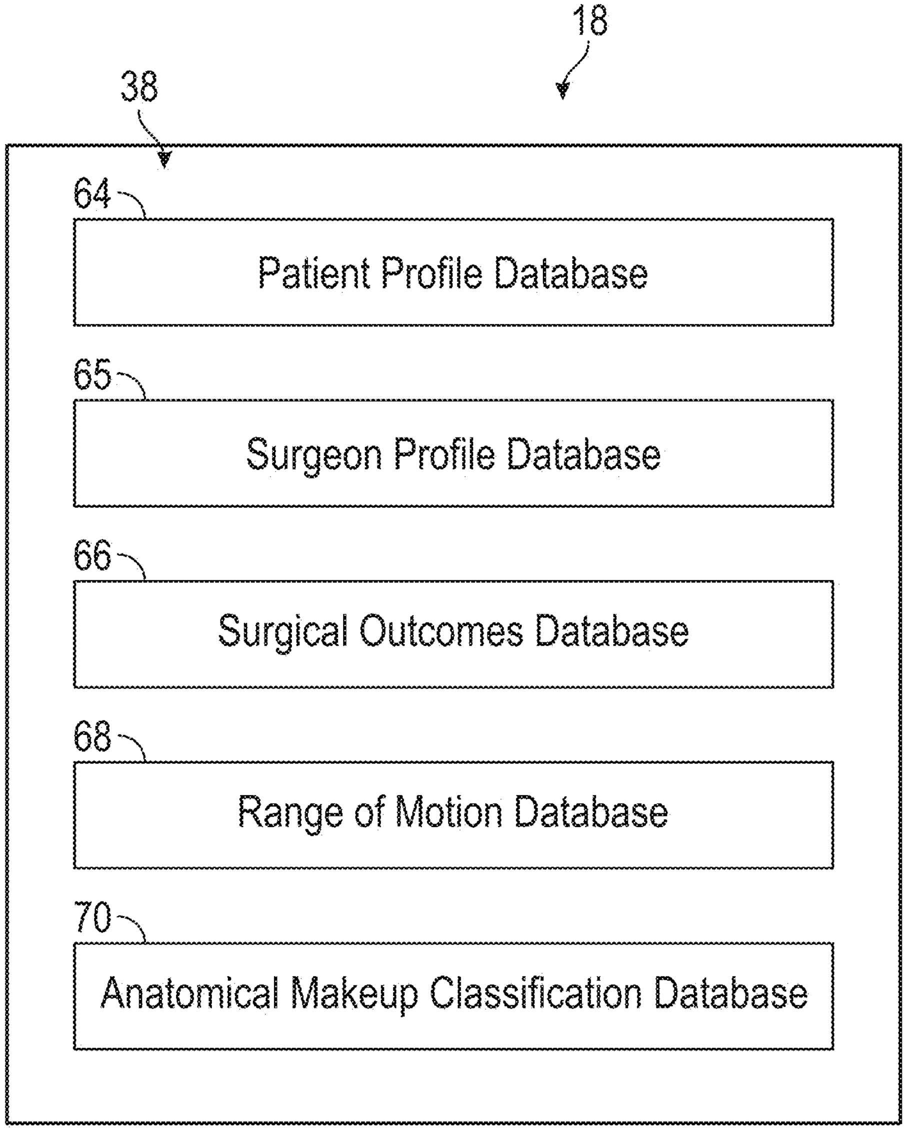
FIG. 3 discloses cloud-based databases that may be accessed by a surgical planning system.

Referring now to FIG. 3, with continued reference to FIG. 2, the computing device 40 including the processor 42 may be operably connected to storage system(s), such the storage system 18. The computing device 40 may interface with the storage system 18 over the network 20 for accessing various databases 38 stored thereon in order to establish and implement the surgical plans 36.

The databases 38 of the storage system 18 may include a patient profile database 64, a surgeon profile database 65, a surgical outcomes database 66, a range of motion database 68, and an anatomical makeup classification database 70. Additional databases could be stored on and accessed from the storage system 18 within the scope of this disclosure. Moreover, although shown as separate databases, one or more of the databases could be combined or linked together. For example, the anatomical makeup classification database 70 could be combined or linked with the surgical outcomes database 66, the range of motion database 68, or both.

The patient profile database 64 may include information that is part of an indexed and stored record or entry related to one or more current patients associated with the system 10. The information stored on the patient profile database 64 may include the sex, age, ethnicity, height, weight, defect category, procedure type, surgeon, facility or organization, dominant joint, acts of daily living/lifestyle goals profile (e.g., desired post-surgery range of motion for abduction, adduction, external rotation, internal rotation, extension, flexion, external rotation combined with 60° abduction, internal rotation with 60° abduction, etc.), current surgical plan information, etc. for each patient. The patient profile database 64 may further store or link to the images 26 for a given patient.

The surgeon profile database 65 may include information that is part of indexed and stored records or entries related to one or more surgeon users associated with the system 10. The information stored on the surgeon profile database 65 may include the surgeon's name, facility or organization, historical data concerning the types of prior surgeries planned by the surgeon using the system 10, data concerning the types of implants included in the surgeon's preoperative surgical plans, data concerning the actual implants utilized in the surgeon's prior surgeries, etc. In some implementations, the surgeon profile database 65 may interface with the patient profile database 64 for linking each surgeon from the surgeon profile database 65 to his/her patients listed in the patient profile database 64.

The surgical outcomes database 66 may include information that is part of indexed and stored records or entries related to one or more prior patients associated with the system 10. The surgical outcomes database 66 may be created based on information logged by surgeons and/or other staff users after performing each surgery and at each follow-up visit for indicating the progress of the prior patient. The information stored on the surgical outcomes database 66 may include the sex, age, ethnicity, height, weight, defect category, procedure type, specific implants used, surgeon, facility or organization, dominant joint, visual analog pain scores, ASES scores, achieved acts of daily living/lifestyle profile (e.g., achieved post-surgery range of motion for abduction, adduction, external rotation, internal rotation, extension, flexion, external rotation combined with 60° abduction, internal rotation with 60° abduction, etc.), surgical plan information, etc. for each prior patient. The surgical outcomes database 66 may additionally store or link to preoperative and postoperative images 26 for each prior patient.

The range of motion database 68 may include information that is part of indexed and stored records or entries related to one or more current and prior patients associated with the system 10. The range of motion database 68 may store range of motion data derived from range of motion simulations performed by the computing device 40 for each surgical plan 36. The range of motion data may include information related to simulated joint motions (e.g., abduction/adduction, flexion/extension, internal/external rotation, etc.), identified contact or collision points for various implant positions, angular arc and mode of collision (e.g., implant-to-implant, implant-to-bone, bone-to-bone, etc.) for various implant positions, adjusted center of rotation of implants in multiple increments and offset directions for various implant positions, etc.

The anatomical makeup classification database 70 may store a plurality of anatomical makeup classifications that characterize anatomical differences and variances within the anatomical differences within a representative patient population for one or more intended surgeries (e.g., total shoulder, reverse shoulder, etc.). In some implementations, the representative patient population may be derived by analyzing image data, such as images from the prior patients stored on the surgical outcomes database 66 and/or any other imaging source, associated with a plurality of prior patients who have already received the intended surgery. Each of the plurality of anatomical makeup classifications is a numerical classification of an anatomical makeup of a bone or a joint of the representative patient population.

Figure 4:
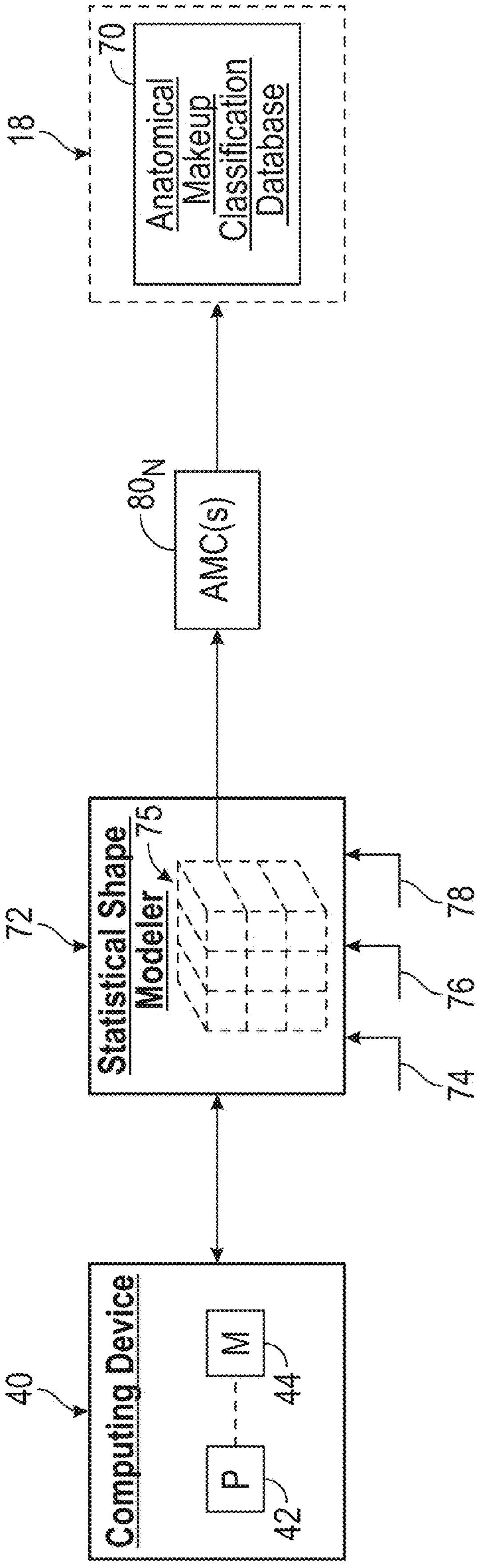
FIG. 4 discloses aspects of the surgical planning system of FIG. 1 including a statistical shape modeler.

Referring now to FIG. 4, with continued reference to FIGS. 1-3, the computing device 40 may interface with a statistical shape modeler 72 for creating the anatomical makeup classification database 70. The statistical shape modeler 72 may be a software package stored in the memory 44 of the computing device 40 or in the storage system 18 and which may be executed by the processor 42.

The statistical shape modeler 72 may receive a plurality of sets of image data 74 associated with a bone or joint of interest. In some implementations, the sets of image data 74 is made up of tens of thousands of sets of image data. Each set of image data 74 may include 2D and/or 3D anatomical images specific to prior patients of a representative patient population for the bone or joint of interest and related to a given type of surgery. The statistical shape modeler 72 may analyze the plurality of sets of image data 74 for constructing a statistical shape model (SSM) 75.

As an input, the statistical shape modeler 72 may receive a plurality of predefined modes 76 to be used for analyzing the plurality of sets of image data 74. Each of the modes 76 is a descriptor configured for characterizing anatomical differences in the bone or joint associated with the statistical shape model 75. Exemplary modes 76 that may be provided to the statistical shape modeler 72 may include but are not limited to size of glenoid, size of scapula, amount of inclination, amount of version, projected amount of glenoid and sagittal neck length, angle of glenoid relative to scapular neck, critical shoulder angle, projection of acromion and/or coracoid, size of humeral head, varus/valgus of humeral head, varus/valgus of femur and/or tibia, internal/external rotation of femur and/or tibia, integrity of subscapularis, deltoid, and/or supraspinatus, ML and AP width, intercondylar notch depth, tibial slope, Q-angle of the knee, ACL/PCL stability, MCL/LCL stability, amount of flexion, amount of extension, quality and amount of soft tissue surrounding joint, patellar tracking angle, bone density, bone quality subluxation percentage, anatomical landmarks, joint space, pre-operative range of motion, any combinations of the foregoing, etc.

In some implementations, at least seven different modes may be utilized by the statistical shape modeler 72 to characterize the statistical shape model 75. However, a greater or fewer number of modes may be provided within the scope of this disclosure.

In some implementations, the modes 76 may not be predefined. Rather, the statistical shape modeler 72 may be programmed to utilize artificial intelligence (e.g. a neural network) or machine learning to extrapolate the modes that best relate to the bone or joint being modeled within the statistical shape model 75.

As another input, the statistical shape modeler 72 may receive a plurality of predefined standard deviations 78 to be used for analyzing the plurality of sets of image data 74. Each standard deviation 78 may represent anatomical variances (e.g., distances between features, orientation of features, relative features, etc.) contained within each of the plurality of predefined modes 76. The standard deviations 78 may be used to validate a percentile coverage of the representative patient population that is represented within the statistical shape model 75. In some implementations, at least seven different standards of deviation (e.g., −3, −2, −1, 0, 1, 2, and 3) may be utilized by the statistical shape modeler 72 to further characterize all anatomical variances contained within the anatomies described within the statistical shape model 75. However, a greater or fewer number of standard deviations could be utilized within the scope of this disclosure.

The statistical shape modeler 72 may, in response to commands from the processor 42, combine the plurality of standard deviations 78 with the plurality of predefined modes 76 to assign a plurality of anatomical makeup classifications 80N, wherein N is any number, to the bone or joint associated with the statistical shape model 75 in order to categorize the anatomical makeup of the entire patient population represented within the statistical shape model 75. Each anatomical makeup classification 80N may then be saved in the anatomical makeup classification database 70 of the storage system 18.

Figure 5:
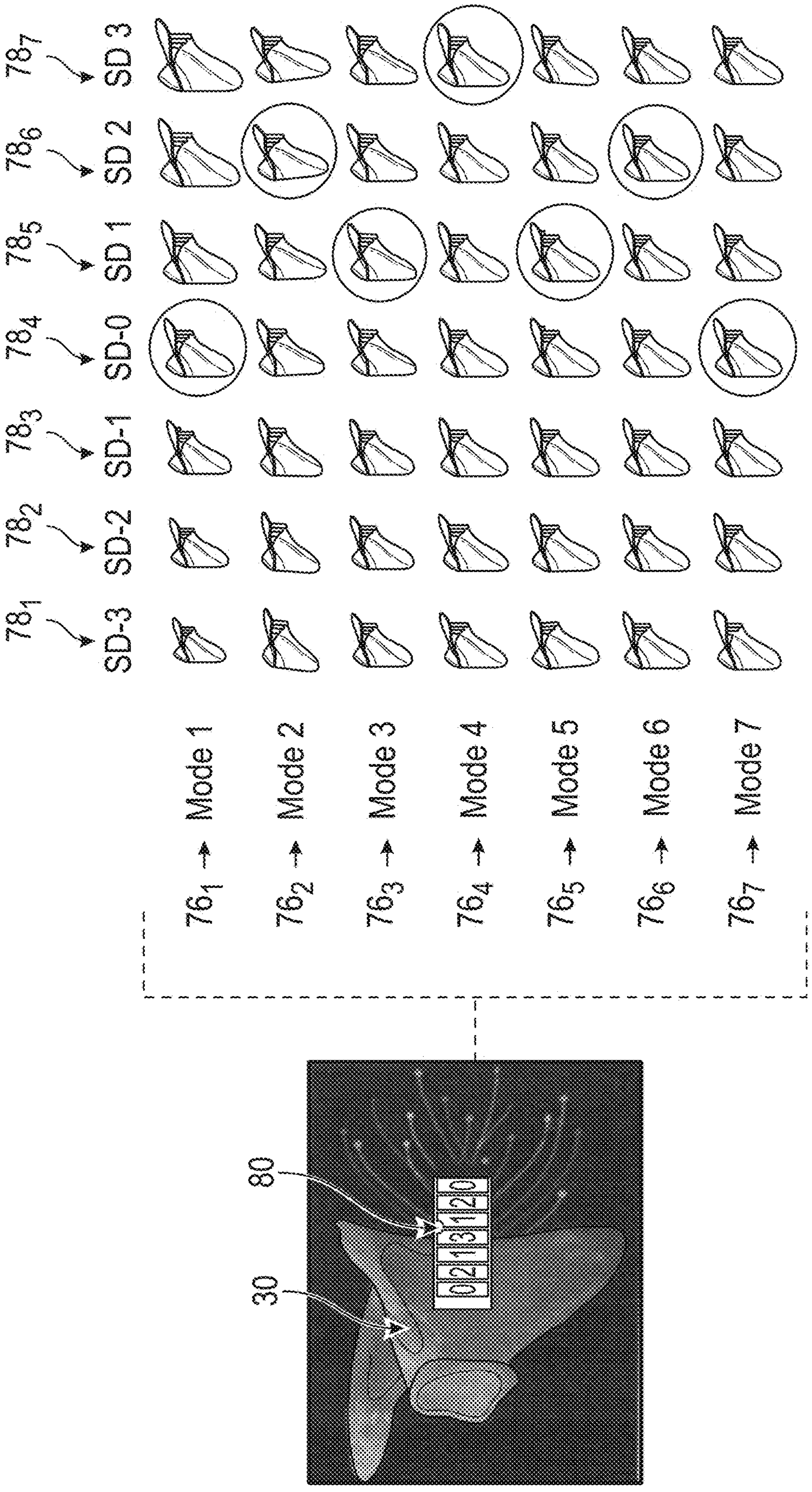
FIG. 5 discloses an anatomical makeup classification that may be assigned by a surgical planning system.

FIG. 5 illustrates an exemplary anatomic makeup classification (AMC) 80 as assigned to a specific bone model 30 derived from the statistical shape model 75. In an embodiment, the bone model 30 is a 3D model of a scapula of a shoulder joint. However, other bones and joints could also be classified in a similar manner.

The statistical shape modeler 72 of FIG. 4 may analyze the bone model 30 in respect to each of a plurality of modes $\mathbf{76}_1$ to $\mathbf{76}_7$, in order to characterize any anatomical differences in the bone model 30 compared to the other similar bones/joints associated with the statistical shape model 75. Of course, a greater or fewer number of modes are possible.

The statistical shape modeler 72 may further characterize any anatomical variances contained within each of the plurality of predefined modes $\mathbf{76}_1$-$\mathbf{76}_7$ by analyzing each of the modes with respect to a plurality of standard deviations $\mathbf{78}_1$-$\mathbf{78}_7$. Of course, a greater or fewer number of standards of deviation are possible.

In the implementation shown in FIG. 5, the bone model 30 is assigned the numerical value 0213120 as its anatomical makeup classification 80. This numerical value represents a standard of deviation of 0 within the first mode $\mathbf{76}_1$, a standard of deviation of 2 within the second mode $\mathbf{76}_2$, a standard of deviation of 1 within the third mode $\mathbf{76}_3$, a standard of deviation of 3 within the fourth mode 764, a standard of deviation of 1 in the fifth mode 765, a standard of deviation of 2 within the sixth mode 766, and a standard of deviation of 0 in the seventh mode $\mathbf{76}_7$. The anatomical makeup classification 80 is a unique numeric identifier for describing the anatomy associated with the bone model 30.

Figure 6:
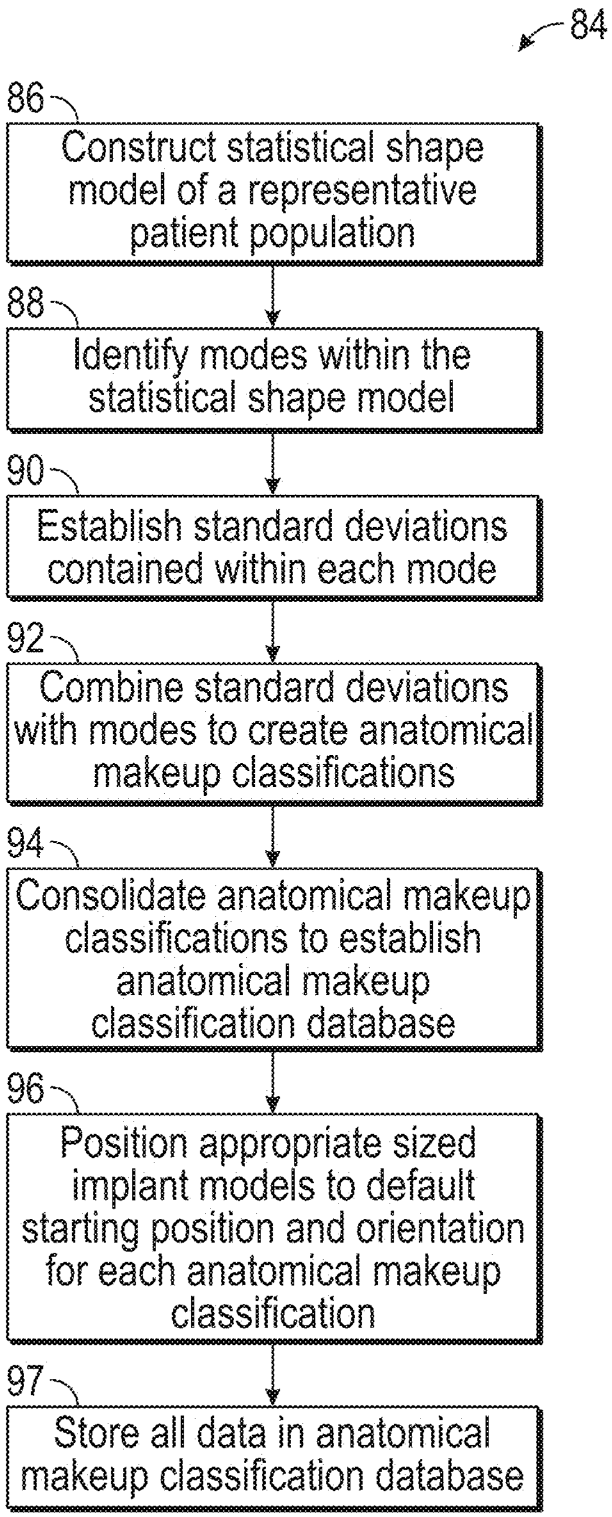
FIG. 6 discloses a method for establishing an anatomical makeup classification database of a surgical planning system.

FIG. 6, with continued reference to FIGS. 1-5, schematically illustrates a method 84 for creating the anatomical makeup classification database 70 described above. The method 84 may be performed as part of a surgical planning procedure. Fewer or additional steps than are recited below could be performed within the scope of this disclosure, and the recited order of steps is not intended to limit this disclosure. The system 10, via any of its associated computing devices and modules, may be configured to execute each of the steps of the method 84. In an exemplary implementation, the computing device 40 of the host computer 12 may be programmed to execute the method 84. However, other implementations are further contemplated within the scope of this disclosure.

A statistical shape model 75 that is representative of a patient population having pathologic anatomies associated with an intended surgery may be constructed at step 86. A plurality of modes 76 may be identified within the statistical shape model 75 at step 88. The modes 76 may characterize anatomical differences within the statistical shape model 75.

Next, at step 90, a plurality of standard deviations 78 of anatomical variances contained within each of the modes 76 may be established. The standard deviations 78 may be used to validate a percentile coverage of the representative patient population associated with the statistical shape model 75.

The standard deviations 78 may be combined with the modes 76 to create a plurality of unique anatomical makeup classifications 80 at step 92. At step 94, the anatomical makeup classifications 80 may be consolidated to form the anatomical makeup classification database 70. The anatomical makeup classification database 70 may therefore represent major variances within the representative patient population which may influence implant function.

As further part of the method 84, an appropriate sized implant model 32 may be selected and positioned to a default starting position and orientation relative to the bone or joint associated with each of the plurality of anatomical makeup classifications 80 at step 96. The default starting positions and orientations of the implant models 32 may therefore also be linked to and stored, at step 97, with the anatomical makeup classifications 80 as part of the anatomical makeup classification database 70.

Once built, the anatomical makeup classification database 70 may enable additional features, processes, and/or capabilities to be implemented within or executed by the system 10 for enhancing surgical planning. Example implementations of such features are detailed below.

Figure 7:
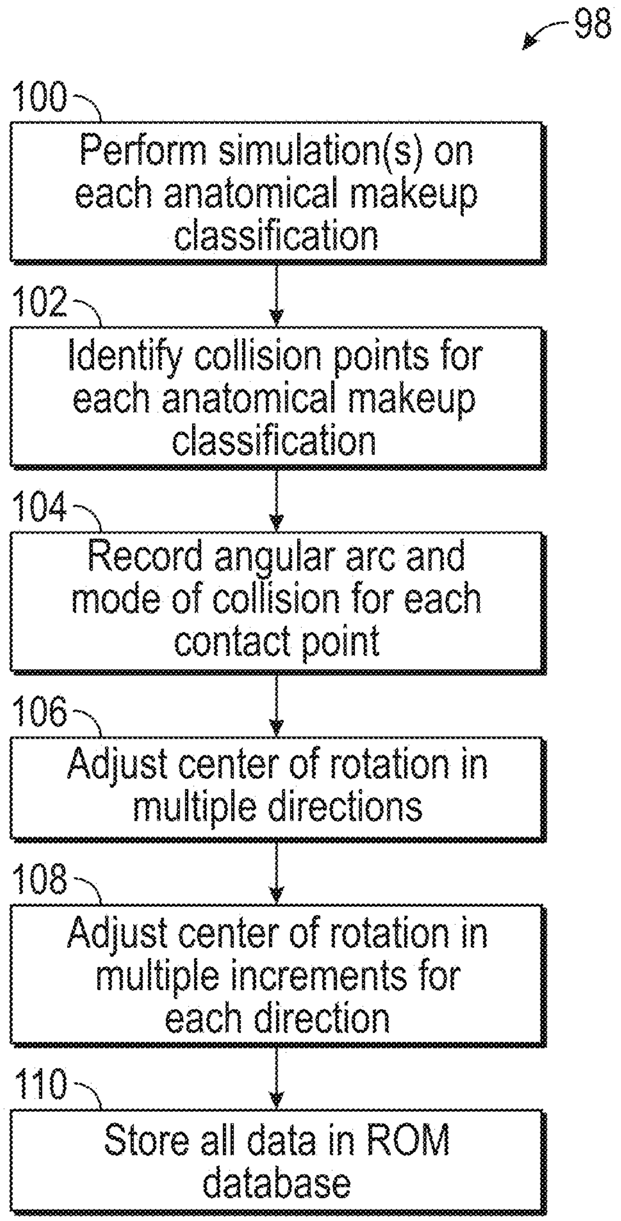
FIG. 7 discloses a method for establishing a range of motion database of a surgical planning system.

FIG. 7, for example, illustrates a method 98 for augmenting the range of motion database 68 with the information contained within the anatomical makeup classification database 70. The method 98 may be performed as part of a surgical planning procedure. Fewer or additional steps than are recited below could be performed within the scope of this disclosure, and the recited order of steps is not intended to limit this disclosure. The system 10, via any of its associated computing devices and modules, may be configured to execute each of the steps of the method 98. In an exemplary implementation, the computing device 40 of the host computer 12 may be programmed to execute the method 98. However, other implementations are further contemplated within the scope of this disclosure.

First, at step 100, one or more motion simulations may be performed on each anatomical makeup classification 80 stored on the anatomical makeup classification database 70. The motion simulations may be performed within a range of motion modeler 101, which may be a software package stored in the memory 44 of the computing device 40 or in the storage system 18 and which may be executed by the processor 42 (see, e.g., FIG. 8). The range of motion modeler 101 may receive each of the anatomical makeup classifications 80 (and each associated bone model 30 and implant model 32, including default implant starting positions and orientations) as inputs from the anatomical makeup classification database 70 when performing the motion simulations.

The range of motion simulations actually performed at step 100 will depend on the type of bone or joint being analyzed, among other criteria. Examples of the types of motions that can be simulated as part of step 100 of the method 98 include but are not limited to abduction/adduction, flexion/extension, internal/external rotation, etc.

Contact or collision points may be identified at step 102 for identifying the range of motion end points for each range of motion simulation performed on each anatomical makeup classification 80. The angular arc and mode of collision (e.g., implant-to-implant, implant-to-bone, bone-to-bone, etc.) for each contact point may be recorded at step 104.

The center of rotation of the implant models 32 positioned within the bone models 30 for each anatomical makeup classification 80 may be adjusted at step 106. In some implementations, this step may include adjusting each implant model 32 in at least three offset directions (e.g., medial, interior, and posterior) relative to the respective bone model 30 to simulation different positions of the implant models 32.

At step 108, the center of rotation of the implant model 32 for each anatomical makeup classification 80 may be adjusted relative to the respective bone model 30 in multiple increments for recording the angular arcs and collision modes associated with the adjusted positions. All range of motion data derived from the simulations performed at steps 100-108 may then be saved within the range of motion database 68 at step 110.

Figure 9:
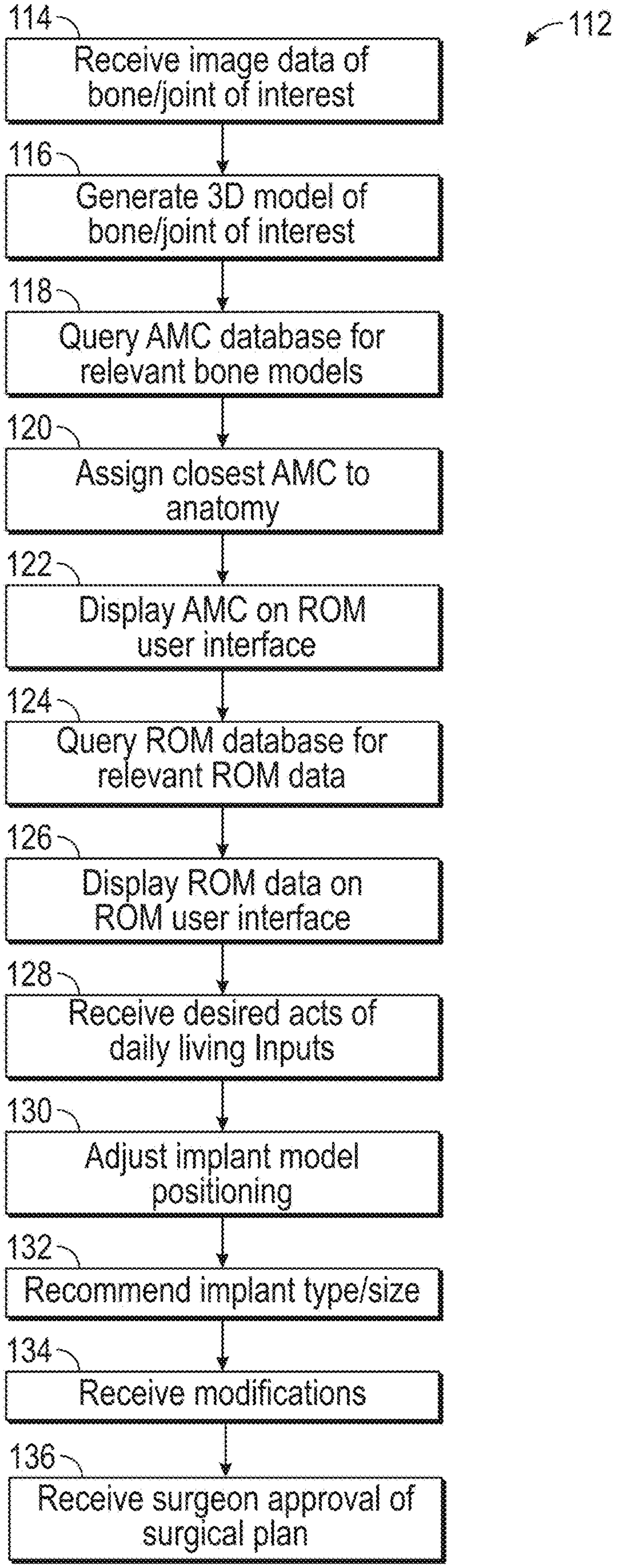
FIG. 9 discloses a method for planning an orthopedic procedure on a respective patient using a surgical planning system.

FIG. 9 schematically illustrates a method 112 for planning an orthopedic procedure for a respective patient using the system 10. The method 112 may be performed as part of a surgical planning procedure for preparing a surgical plan for the patient. Fewer or additional steps than are recited below could be performed within the scope of this disclosure, and the recited order of steps is not intended to limit this disclosure. The system 10, via any of its associated computing devices and modules, may be configured to execute each of the steps of the method 112. In an exemplary implementation, the computing device 40 of one or more of the client computers 14 may be programmed to execute the method 112. However, other implementations are further contemplated within the scope of this disclosure.

Image data of a bone or joint of interest of the patient may be received at step 114. The image data may be received directly from the imaging device 16 or may be acquired by accessing the record or entry associated with the patient from the patient profile database 64.

A 3D model 30 (FIG. 2) of the bone or joint of interest may be generated at step 116. The planning environment 28 of the computing device 40 may incorporate and/or interface with one or more modeling packages, such as a computer aided design (CAD) package, to render the 3D model of the bone or joint of interest.

Next, at step 118, the computing device 40 may query the anatomical makeup classification database 70 to locate bone models stored therein that have similar anatomical makeup classifications. The anatomical makeup classification 80 (FIG. 4) that is closest to the anatomy encompassed by the 3D model 30 (FIG. 2) may then be assigned to the 3D model 30 at step 120 and displayed on a range of motion user interface of the computing device 40 at step 122. As part of displaying the anatomical makeup classification 80, a confidence level indicator may be displayed within the range of motion user interface for visually indicating the similarity between the assigned anatomical makeup classification 80 and the anatomy being analyzed. The confidence level indicator may be displayed as a percentage or any other visual indicator.

The range of motion database 68 may be queried at step 124 to obtain range of motion data that is relevant to the assigned anatomical makeup classification 80. The range of motion data associated with the assigned anatomical makeup classification 80, including information such as the angular arc and the mode of impingement, may be displayed on the range of motion user interface at step 126.

At step 128, the surgeon or other staff user of the system 10 may be queried to select the desired acts of daily living goals of the patient. The positioning of the implant model 32 may be automatically adjusted relative to the bone model based on the selected acts of daily living at step 130. The system 10 may then output a recommended implant size/type and position and orientation for meeting the selected acts of daily living at step 132.

The surgeon may be prompted to modify the recommended implant type, positioning, and/or orientation per his/her clinical judgement at step 134. The method 112 may end at step 136 in response to receiving the surgeon's approval of the surgical plan. As part of this step, a comparison of the simulated range of motion results stored in the ROM database 68 to the range of motion achieved by the surgeon's planned positions and orientations may be presented to the user within a graphical user interface. This step may further include notifying the surgeon within the graphical user interface of any potential impact the proposed changes may have based on past surgical outcome data associated with prior patients having similar anatomical makeup classifications.

Figure 10:
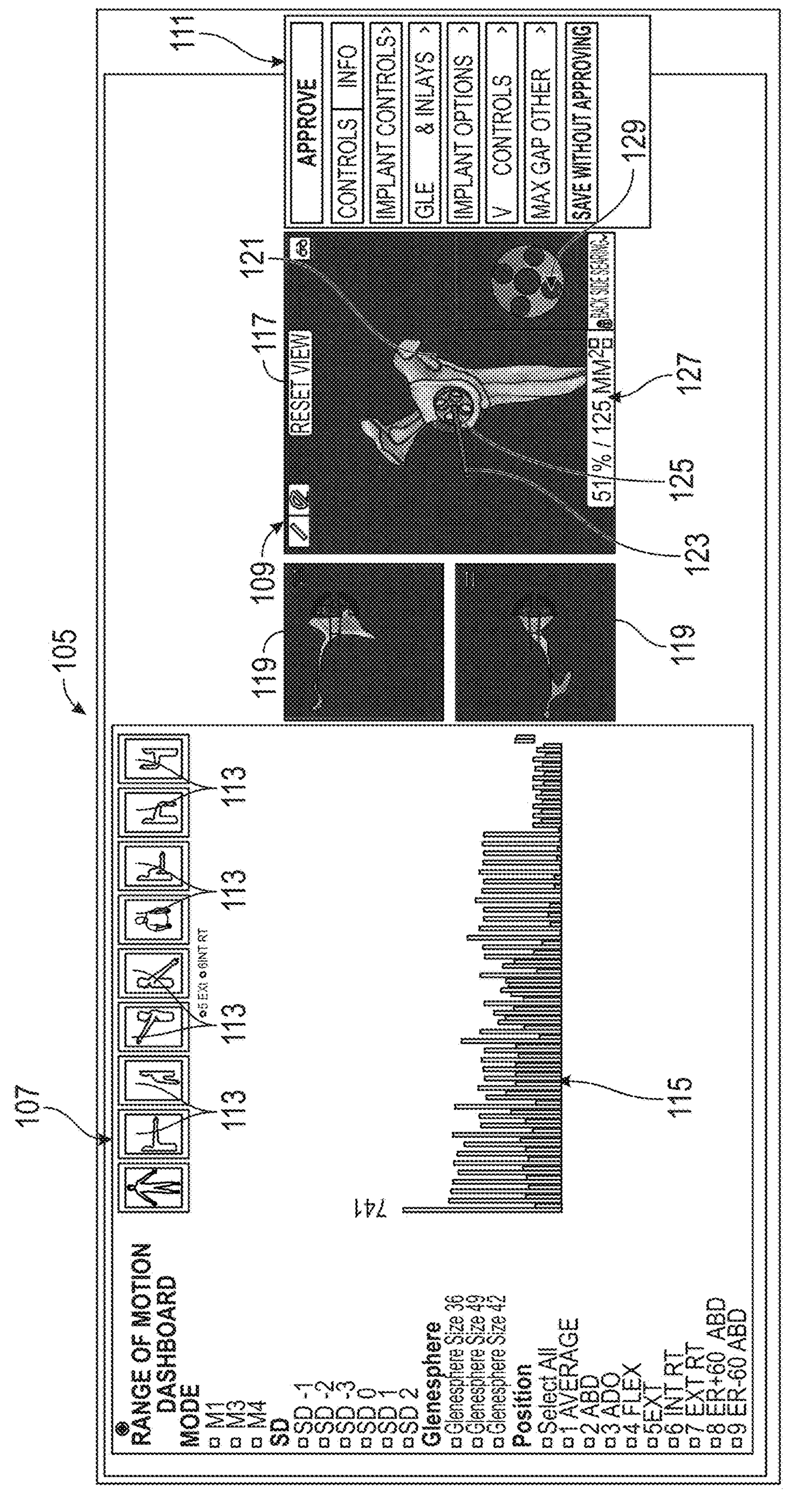
FIG. 10 discloses a user interface of a surgical planning system.

FIG. 10 illustrates an exemplary range of motion user interface 105 that may be provided during the method 112 discussed above. The range of motion user interface 105 may be presented within the planning environment 28, for example.

The range of motion user interface 105 may include a range of motion dashboard 107, a display window 109, and a control panel 111. The range of motion dashboard 107 may present various range of motion data to the user. The range of motion dashboard 107 may include a plurality of selectable buttons 113 related to foundational joint motion expectations for the patient. The foundational joint motion expectations that may be represented by the buttons 113 may include but is not limited to desired post-surgery range of motion for abduction, adduction, external rotation, internal rotation, extension, flexion, external rotation combined with 60° abduction, and internal rotation combined with 60° abduction.

The range of motion dashboard 107 may further include a bar graph 115 for illustrating range of motion data for each of the foundational joint motion expectations. For example, the bar graph 115 may provide a visual display of the range of motion achieved for a selected foundational joint motion expectation for one or more AMCs 80 (FIG. 4) that are closest to the anatomy of the patient that the surgical plan is being created for.

The display window 109 may include a 3D window 117 and multiple 2D windows 119. A virtual bone model 121 of the patient's anatomy may be displayed within the 3D window 117 and the 2D windows 119. A positioning of both a virtual guide pin 123 and a virtual implant 125 that is necessary for achieving the desired joint motion expectations may be displayed relative to the virtual bone model 121 to provide the user with information on how to best approach the surgery being planned.

The display window 109 may be manipulated using the control panel 111. For example, the control panel 111 may include a plurality of toggles, buttons, sliders, etc. that allow the user to modify various settings, such as the positioning of the virtual guide pin 123 and/or the virtual implant 125 relative to the virtual bone model 121. In an embodiment, a backside seating amount 127 and a color-coded backside seating map 129 may be provided on the display window 109 and may automatically update as adjustments are made to the virtual positions of the virtual guide pin 123 and the virtual implant 125 relative to the virtual bone model 121. The information presented in the display window 109 may also automatically update as the user pages through each of the buttons 113.

Figure 11:
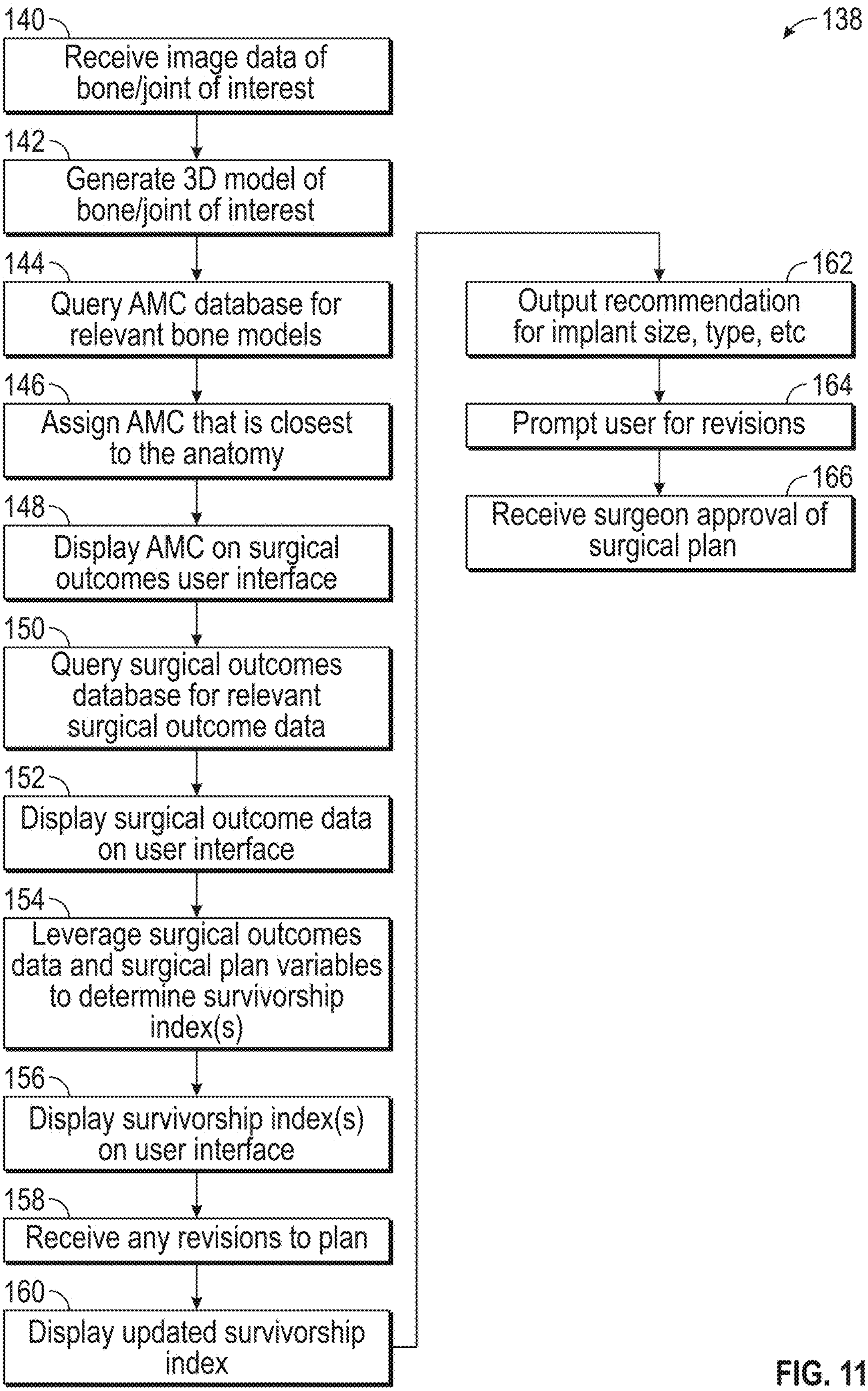
FIG. 11 discloses another method for planning an orthopedic procedure on a respective patient using a surgical planning system.

FIG. 11 schematically illustrates another method 138 for planning an orthopedic procedure for a respective patient using the system 10. The method 138 may be performed as part of a surgical planning procedure for preparing a surgical plan for the patient. Fewer or additional steps than are recited below could be performed within the scope of this disclosure, and the recited order of steps is not intended to limit this disclosure. The system 10, via any of its associated computing devices and modules, may be configured to execute each of the steps of the method 138. In an exemplary implementation, the computing device 40 of one or more of the client computers 14 may be programmed to execute the method 138. However, other implementations are further contemplated within the scope of this disclosure.

Image data of a bone or joint of interest of the patient may be received at step 140. The image data may be received directly from the imaging device 16 or may be acquired by accessing the record or entry associated with the patient from the patient profile database 64.

A 3D model of the bone or joint of interest may be generated at step 142. The planning environment 28 of the computing device 40 may incorporate and/or interface with one or more modeling packages, such as a computer aided design (CAD) package, to render the 3D model of the bone or joint of interest.

Next, at step 144, the computing device 40 may query the anatomical makeup classification database 70 to locate bone models stored therein that have anatomical makeup classifications 80 that are similar to the anatomical makeup classification 80 of the bone or joint of the patient. The anatomical makeup classification 80 that is closest to the anatomy encompassed by the 3D model may then be assigned to the 3D model at step 146 and displayed on a surgical outcomes user interface of the computing device 40 at step 148. As part of displaying the anatomical makeup classification 80, a confidence level indicator may be displayed within the graphical user interface for visually indicating the similarity between the assigned anatomical makeup classification and the anatomy being analyzed. The confidence level indicator may be displayed as a percentage or any other visual indicator.

The surgical outcomes database 66 may be queried at step 150 to obtain surgical outcomes data that is most relevant to the assigned anatomical makeup classification. The surgical outcomes data associated with the assigned anatomical makeup classification 80 may be displayed on the surgical outcomes user interface at step 152. The surgical outcomes data that is displayed to the user may be automatically updated in response to a user prompt, such as when the user changes the planned procedure type, for example.

In an embodiment, the surgical outcomes database 66 may be queried to locate prior surgeries that involved patients having an average bone density that is comparable to an estimated average bone density of a bone associated with the anatomy of the patient. This comparison can be used to recommend a particular surgical implant that is not incompatible with the average bone density of the bone under study, for example.

Next, at step 154, data from the surgical outcomes database 66 for the comparable anatomical makeup classifications 80 and a plurality of variables associated with a surgical plan for operating on the patient may be leveraged in order to determine one or more survivorship predictive indexes. The variables may include factors such as surgical implant type, surgical implant size, surgical implant orientation, a surgical procedure type, a surgical implant backside seating configuration, a fastener orientation, or any combinations thereof. The variables are inputs to the system 10 that may be selected by the surgeon or staff user within the surgical outcomes user interface.

The determined survivorship predictive index may be displayed on the surgical outcomes user interface at step 156. Each survivorship predictive index may be a percentile representation of a confidence level that the surgical plan will result in a successful surgical outcome for at least a predefined amount of time. For example, based on the data of the comparable anatomical makeup classifications 80 and the relevant variables selected/set by the surgeon, the system 10 may determine and display a survivorship predictive index of 40% at three years post-surgery for comparable patients who underwent a standard total shoulder arthroplasty procedure and a survivorship predictive index of 85% at three years post-surgery for comparable patients who underwent a reverse shoulder arthroplasty procedure, thus indicating to the surgeon that a more successful outcome for the patient could likely be obtained by performing a reverse shoulder arthroplasty procedure rather than a standard total shoulder arthroplasty procedure.

After displaying the survivorship predictive index displayed at step 156, the system 10 may prompt the surgeon for making any revisions to the variables associated with the current surgical plan at step 158. If revisions are received as inputs into the system 10, an updated survivorship predictive index may be displayed at step 160.

The system 10 may output a recommended procedure type, implant size/type, and implant position/orientation for best matching the comparable anatomical makeup classifications at step 162. The surgeon may be prompted to modify the recommended implant type, positioning, and/or orientation per his/her clinical judgement at step 164. The method 138 may end after receiving, at step 166, the surgeon's approval of the surgical plan.

Figure 12:
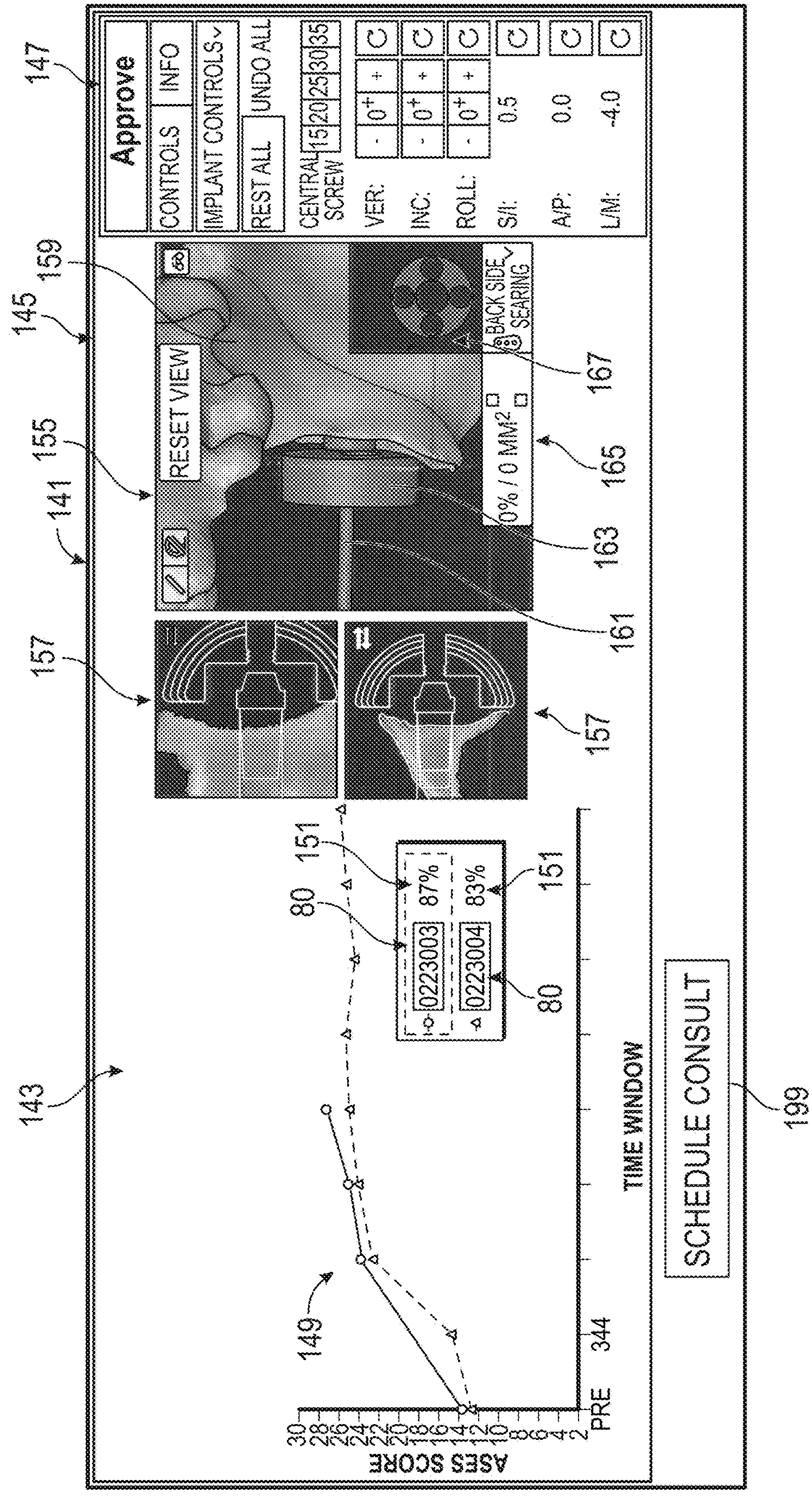
FIG. 12 discloses another user interface of a surgical planning system.

FIG. 12 illustrates an exemplary surgical outcomes user interface 141 that may be provided during the method 138 discussed above. The surgical outcomes user interface 141 may be presented within the planning environment 28, for example.

The surgical outcomes user interface 141 may include a graphical listing 143 for displaying the anatomical makeup classifications 80 most similar to the anatomical makeup classification of the bone or joint of the patient, a display window 145, and a control panel 147.

The graphical listing 143 may include a graph 149 of ASES score versus time for each of the comparable anatomical makeup classifications 80 that are listed. Although two anatomical makeup classifications 80 are shown being listed in FIG. 12, the graphical listing 143 could provide a greater or fewer number of anatomical makeup classifications 80 within the scope of this disclosure.

The graphical listing 143 may further include a confidence level indicator 151 that may be displayed adjacent to each comparable anatomical makeup classification 80. The confidence level indicator 151 may be a percentage or any other visual indicator for visually indicating the similarity between the assigned anatomical makeup classification and the anatomy being analyzed. The user may select the desired comparable anatomical makeup classification 80 using an input selector 153, for example.

The display window 145 may include a 3D window 155 and multiple 2D windows 157. A virtual bone model 159 of the patient's anatomy may be displayed within the 3D window 155 and the 2D windows 157. A virtual guide pin 161 and a virtual implant 163 associated with the selected comparable anatomical makeup classification 80 may be displayed relative to the virtual bone model 159 to provide the user with information on how prior surgeries were conducted for patient's having the comparable anatomical makeup classification 80.

The display window 145 may be manipulated using the control panel 147. For example, the control panel 147 may include a plurality of toggles, buttons, sliders, etc. that allow the user to modify various settings, such as the positioning of the virtual guide pin 161 and/or the virtual implant 163 relative to the virtual bone model 159. In an embodiment, a backside seating amount 165 and a color-coded backside seating map 167 may be displayed on the display window 145 and may automatically update as adjustments are made to the virtual positions of the virtual guide pin 161 and the virtual implant 163 relative to the virtual bone model 159.

The surgical outcomes user interface 141 may further include a consult scheduling button 199. The user may press or otherwise actuate the consult scheduling button 199 in order to arrange a consultation with a surgeon who performed the prior surgery for the comparable anatomical makeup classification 80. Once the consult scheduling button 199 has been actuated, the user and the relevant surgeon may be presented with a series of prompts for coordinating and carrying out the consultation. The consultation may be conducted via chat room, telephone, video conference, etc. If desired, the identities of one or both of the requesting surgeon and the consulting surgeon may be kept confidential during the consultation.

Figure 13A:
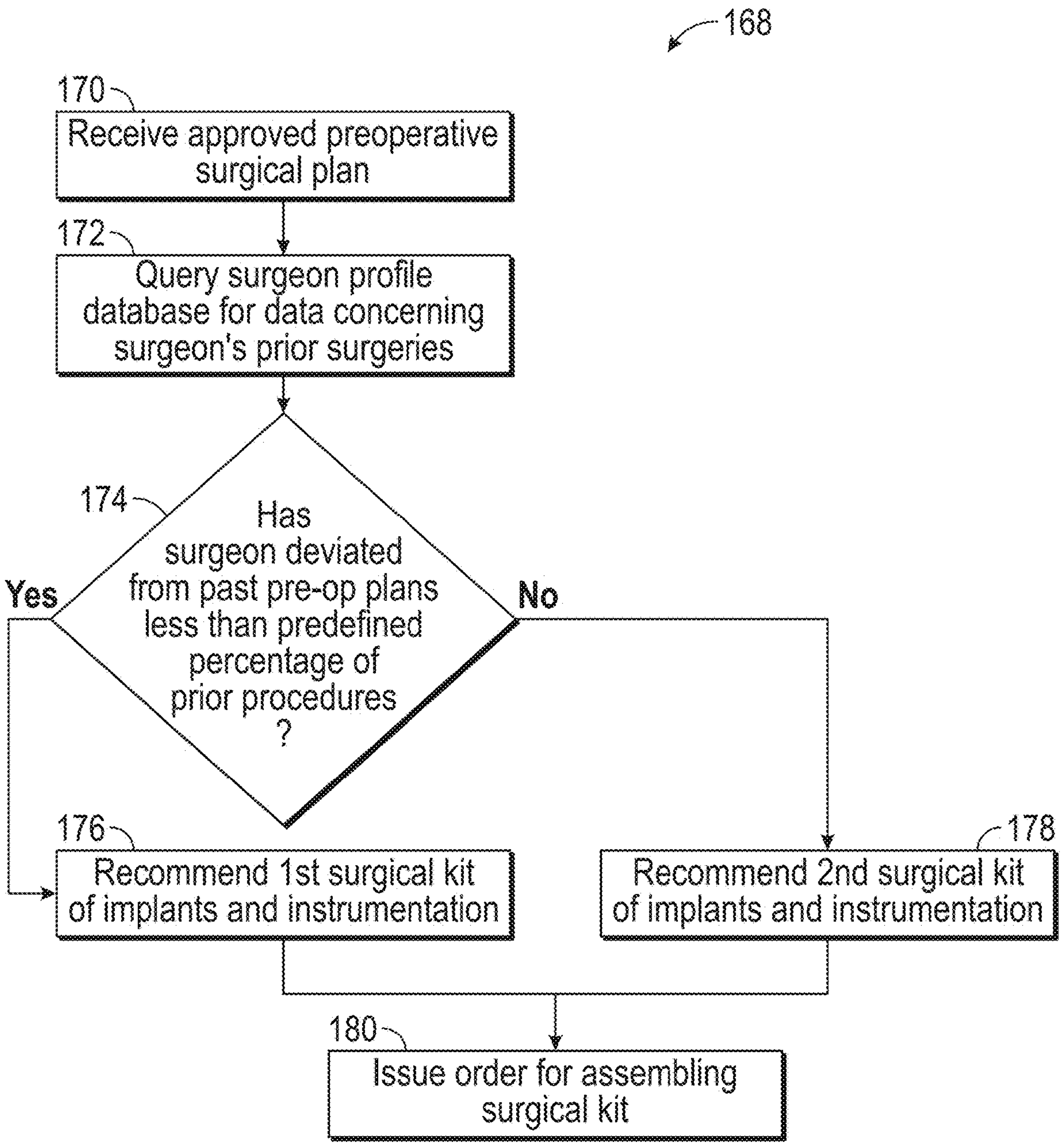
FIG. 13A discloses another method for planning an orthopedic procedure on a respective patient using a surgical planning system.

FIG. 13A schematically illustrates yet another method 168 for planning an orthopedic procedure for a respective patient using the system 10. The method 168 may be performed as part of a surgical planning procedure for preparing a surgical plan for the patient. Fewer or additional steps than are recited below could be performed within the scope of this disclosure, and the recited order of steps is not intended to limit this disclosure. The system 10, via any of its associated computing devices and modules, may be configured to execute each of the steps of the method 168. In an exemplary implementation, the computing device 40 of the host computer 12 may be programmed to execute the method 168. However, other implementations are further contemplated within the scope of this disclosure.

The method 168 may begin at step 170 in response to receiving a preoperative surgical plan that has been approved by a respective surgeon. The surgeon profile database 65 may then be queried at step 172 for data concerning the surgeon's prior surgeries planned using the system 10 for the procedure indicated by the approved preoperative surgical plan. The data analyzed from the surgeon profile database 65 may include the type and amount of implants actually used in the surgeon's prior surgeries, and the type and amount of implants included as part of the preoperative surgical plan for each of the surgeon's relevant prior surgeries.

At step 174, the system 10 may determine, based on a comparison of the pre-operative and post-operative data analyzed at step 172, for example, whether the surgeon has deviated from his/her past preoperative surgical plans in less than a predefined percent of his/her prior surgical procedures. In some implementations, the predefined percent may be defined as 5% of the prior surgical procedures. However, other thresholds may be established within the scope of this disclosure. In an embodiment, a "deviation" is assumed to have taken place when the surgeon changed the pre-planned procedure type, changed the pre-planned implant type, or employed a size deviation of more than one size during the prior surgical procedures.

If a YES flag is returned at step 174, a first surgical kit that includes only those implants and instrumentation necessary for executing the approved preoperative surgical may be recommended at step 176. Alternatively, if a NO flag is returned at step 174, a second surgical kit that includes a greater number of implants and instrumentation than the first surgical kit may be recommended at step 178. An order for assembling the relevant surgical kit may then be issued at step 180.

Figure 13B:
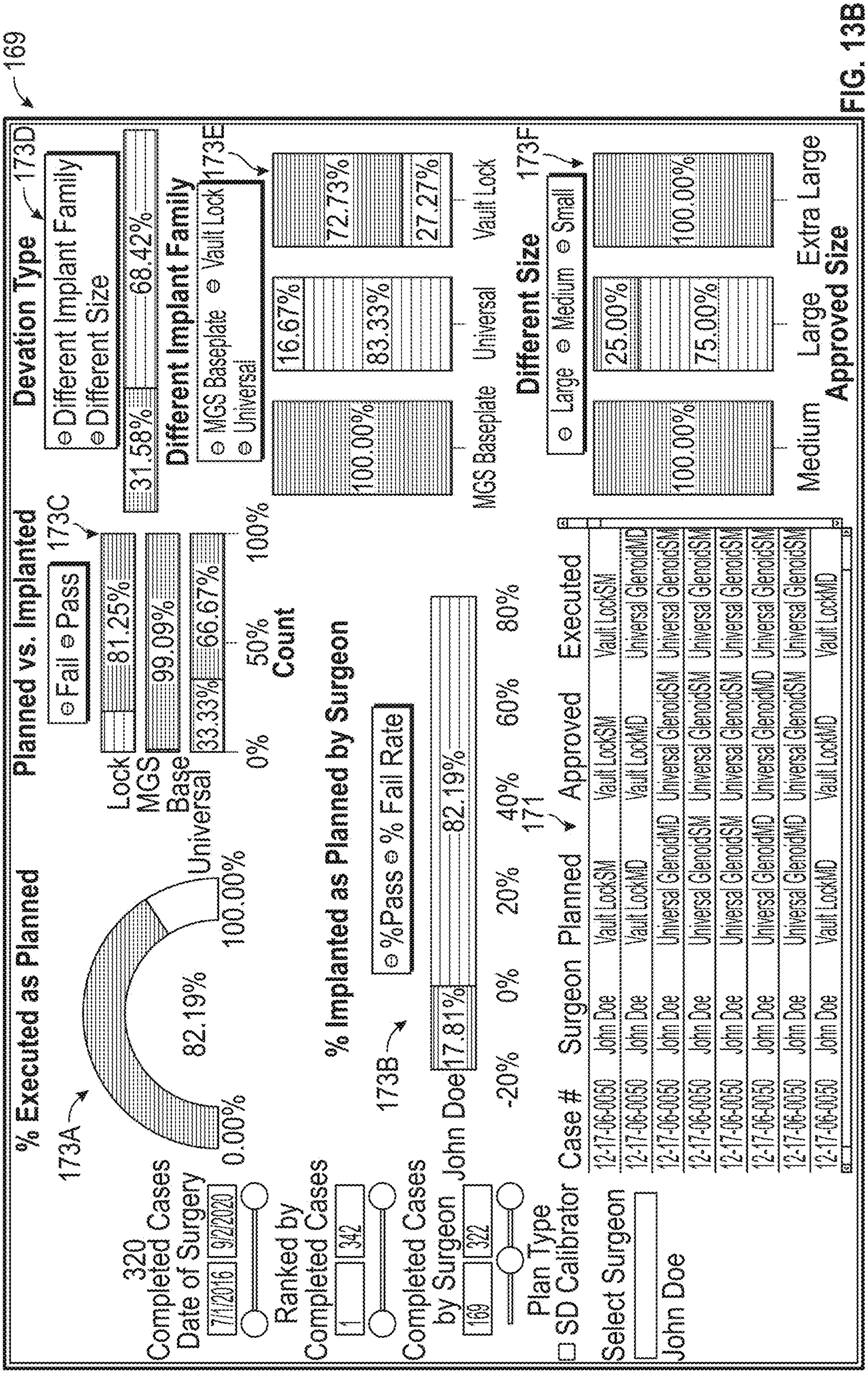
FIG. 13B discloses another user interface of a surgical planning system.

FIG. 13B illustrates an exemplary deviation user interface 169 that may be provided during the method 168 discussed above. The deviation user interface 169 may be presented within the planning environment 28, for example.

The deviation user interface 169 may be configured to present various surgery-related information pertaining to a selected surgeon related to how often the surgeon has deviated from his/her past preoperative surgical plans. The deviation user interface 169 may provide a case listing 171 of the surgeon's prior surgeries and various bar graphs 173A-173F designed for conveying deviation related information to the user. For example, the bar graph 173A may illustrate the percent of prior surgeries executed as planned, the bar graph 173B may illustrate the percent of implants implanted as planned during prior surgeries, the bar graph 173C may illustrate planned versus implanted implants, the bar graph 173D may illustrate deviation type, the bar graph 173E may illustrate different implant families used in the prior surgeries, and the bar graph 173F may illustrate different sizes of implants used during prior surgeries. Other deviation related information could alternatively or additionally be conveyed to the user via the deviation user interface 169.

Figure 14:
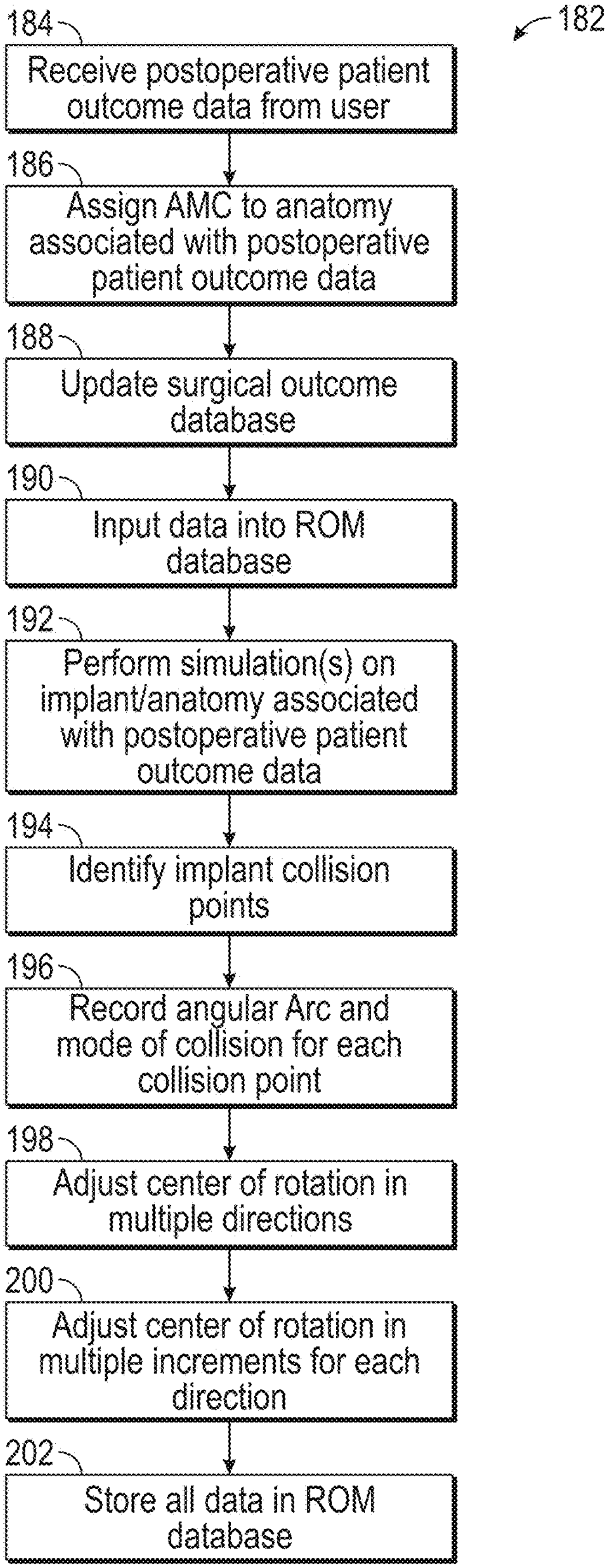
FIG. 14 discloses a method for postoperatively updating one or more databases associated with a surgical planning system.

FIG. 14 schematically illustrates a method 182 for post-operatively updating one or more databases 38 associated with the system 10. The method 182 may be performed subsequent to using the system 10 to prepare a surgical plan for a patient and subsequent to implementing the surgical plan during an actual surgery. Fewer or additional steps than are recited below could be performed within the scope of this disclosure, and the recited order of steps is not intended to limit this disclosure. The system 10, via any of its associated computing devices and modules, may be configured to execute each of the steps of the method 182. In an exemplary implementation, the computing device 40 of the host computer 12 may be programmed to execute the method 182. However, other implementations are further contemplated within the scope of this disclosure.

The system 10 may receive postoperative patient outcome data from a user at step 184. In some implementations, the postoperative patient outcome data may be manually entered by a surgeon or other staff after intraoperatively performing a surgical procedure on the patient according to a preoperative surgical plan previously created within the system 10. In other implementations, the postoperative patient outcome data may be automatically communicated to the system 10 after performing the surgical procedure as part of a closed feedback loop that can be implemented via a neural network, for example. The postoperative outcome data may include information such as the size and types of implants used during the now completed surgical procedure, the positions and orientations of the used implants, implant failure data, data related to the achievement or non-achievement of pre-operative acts of daily living goals, etc.

An anatomic makeup classification 80 may be assigned to each anatomy associated with the postoperative patient outcome data at step 186. This may be achieved, for example, by querying the anatomical makeup classification database 70 to locate bone models stored therein that have anatomical makeup classifications that are similar to the anatomical makeup classification of the anatomy indicated within the postoperative patient outcome data.

At step 188, the surgical outcomes database 66 may be updated with the information contained within the postoperative patient outcome data. For example, the surgical outcomes database 66 may be updated with the size and types of implants used during the now completed surgical procedure, the positions and orientations of the used implants, etc.

The size, type, position, and orientation of the implants indicated within the postoperative patient outcome data may be input into the range of motion database 68 at step 190. Next, at step 192, one or more motion simulations may be performed on the anatomy and implants associated with the postoperative patient outcome data. Contact or collision points may be identified at step 194 for identifying the range of motion end points for each range of motion simulation performed. The angular arc and mode of collision (e.g., implant-to-implant, implant-to-bone, bone-to-bone, etc.) for each contact point may be recorded at step 196.

The center of rotation of the implants associated with the postoperative patient outcome data may be adjusted at step 198. At step 200, the center of rotation of the implants may be adjusted relative to the respective bone model in multiple increments for recording the angular arcs and collision modes associated with the adjusted positions. All range of motion data derived from the simulations performed at steps 190-200 may then be saved within the range of motion database 68 at step 202.

Figure 15:
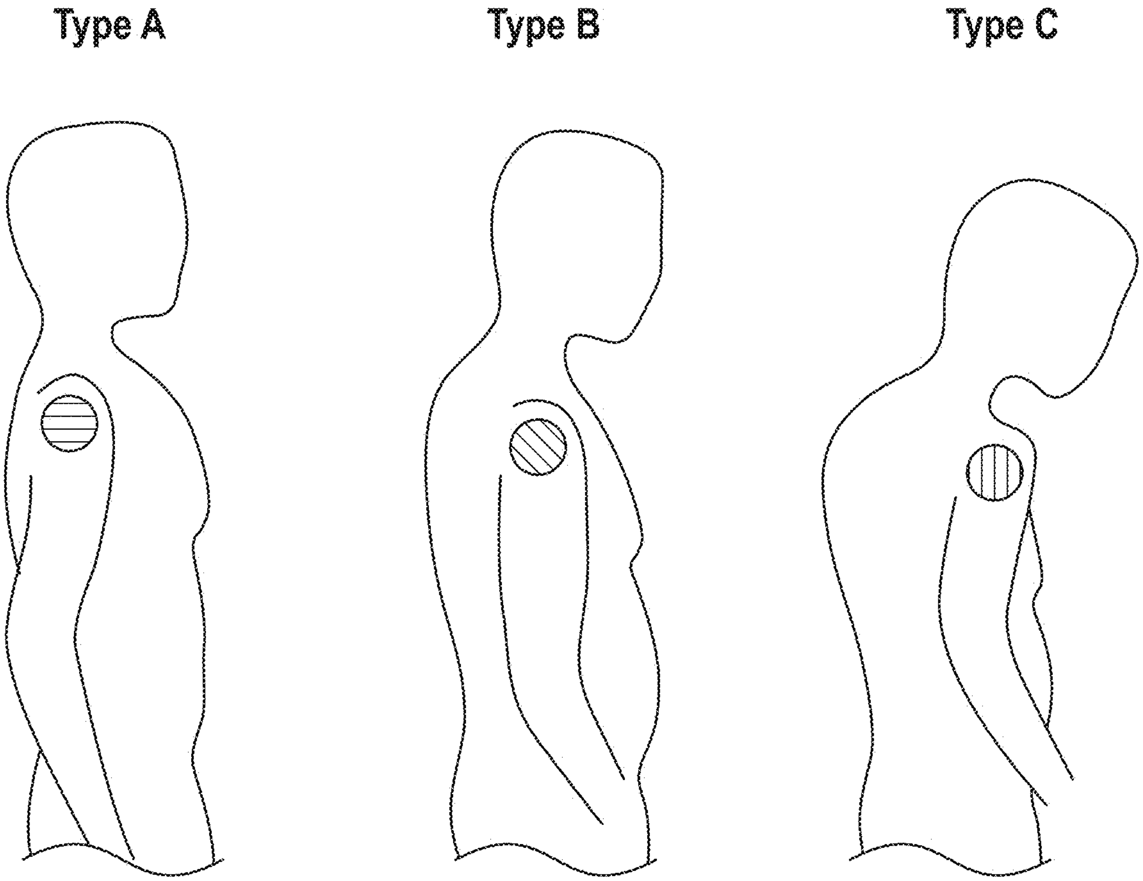
FIG. 15 (Related Art)
FIG. 15 discloses a set of posture types associated with an anatomy.

Referring to FIG. 15, the anatomy of a patient may be associated with a respective posture as disclosed in Moroder, P., et al. (2020). The influence of posture and scapulothoracic orientation on the choice of humeral component retrotorsion in reverse total shoulder arthroplasty. J Shoulder Elbow Surg (2020) 29, 1992-2001. A range of postures may be assigned to a set of posture types of an anatomy (e.g., A, B, C). FIG. 15 discloses a set of posture types (e.g., A, B, C). Posture type A may be representative of a perfect posture. Posture types B and C may deviate from posture type A.

Utilizing the techniques disclosed herein, one or more characteristics associated with a posture of the patient may be determined. Although three posture types are disclosed, it should be understood that fewer or more than three posture types may be utilized according to the teachings disclosed herein. The posture of a patient may affect a relative position between two or more bones and/or joints, including non-adjoining and/or adjoining bones. The posture of a patient may affect a relative position between opposed articular surfaces of adjoining bones. Utilizing the techniques disclosed herein, the position and orientation of one or more implants for treating the patient may be established based on the determined posture characteristics.

Figure 16C:
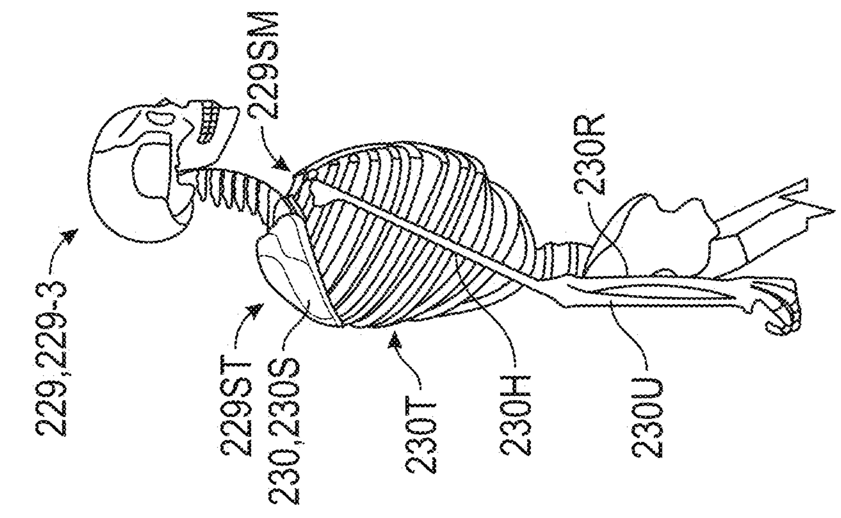
FIGS. 16A-16C disclose anatomical models associated with a set of posture types of an anatomy.
Figure 16B:
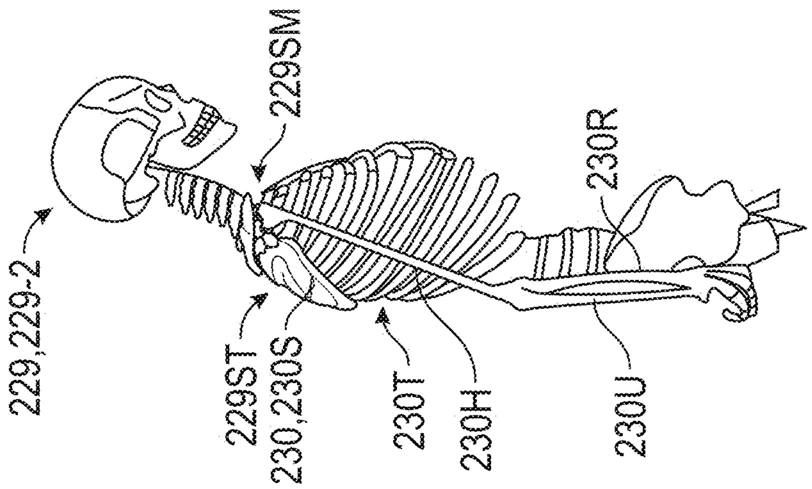
Figure 16A:
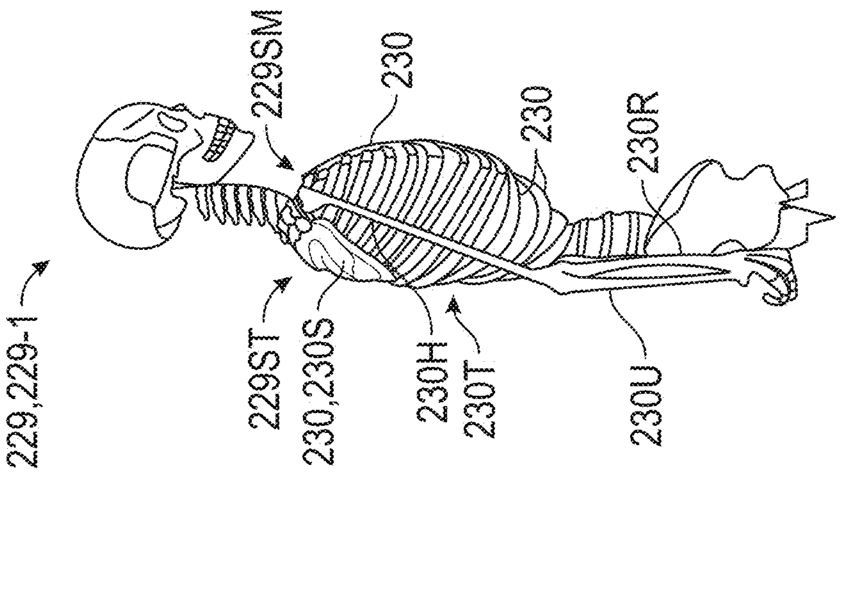

FIGS. 16A-16C disclose anatomical models 229 (indicated as models 229-1, 229-2, 229-3). The memory 44 may be configured to store one or more anatomical models 229 and/or one or more three-dimensional bone models 230 associated with one or more bones. The anatomical models 229-1 to 229-3 may be associated with respective patients. The anatomical models 229 may include one or more bone models 230, which may be associated with any of the bones of the anatomy. The bone models 230 may be representative of bones associated with a shoulder joint, such as a scapula and/or humerus, and one or more bones of an associated limb, such as an ulna and/or radius of a forearm. The bone models 230 may be representative of bones associated with a scapulothoracic joint, such as a scapula and a thorax (e.g., rib cage). The scapula may be associated with a scapula bone model 230S. The humerus may be associated with a humerus bone model 230H. The humerus model 330H and the scapula model 330S may be associated with a shoulder joint model 229SM. The ulna and radius may be associated with an ulna bone model 230U and radius bone model 230R. The thorax may be associated with a thorax bone model 230T. The scapula model 330S and the thorax model 330T may be associated with a scapulothoracic joint model 229ST. The thorax bone model 230T may include a set of bone models 230 representative of various bones of the thorax, including a sternum, one or more thoracic vertebrae, and/or one or more ribs. One or more of the ribs may cooperate with the scapula to establish the scapulothoracic joint. The anatomical models 229 and/or associated bone models 230 may be established and arranged utilizing any of the techniques disclosed herein.

Figure 17A:
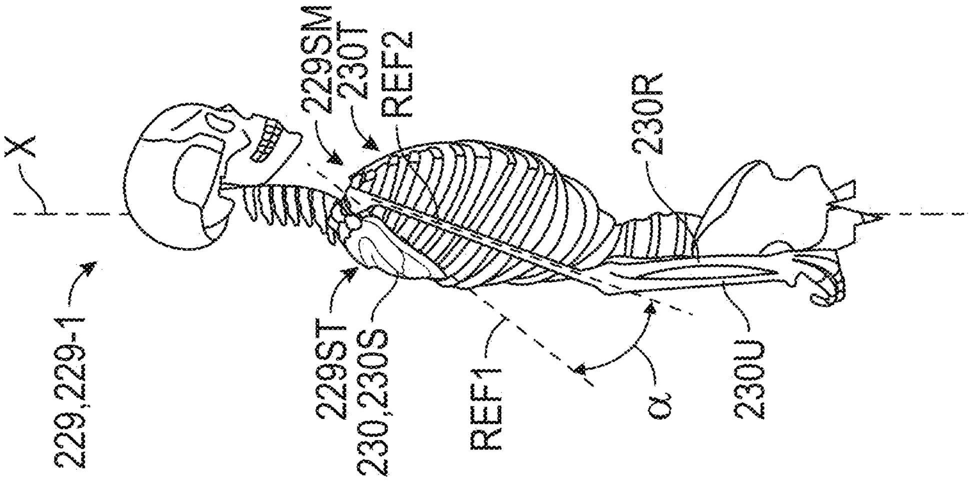
FIGS. 17A-17C disclose scapular angles associated with the respective posture types of FIGS. 16A-16C.
Figure 17B:
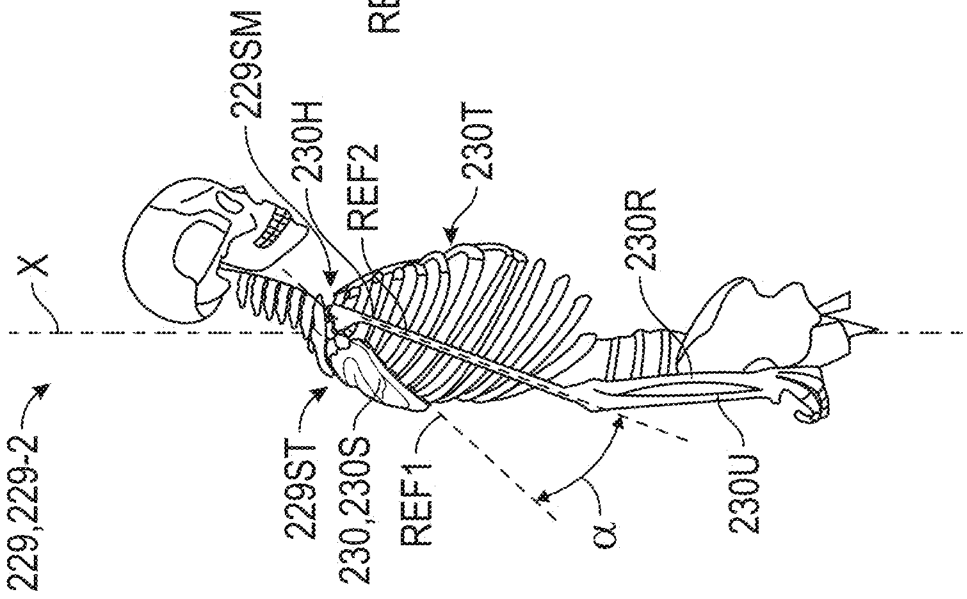
Figure 17C:
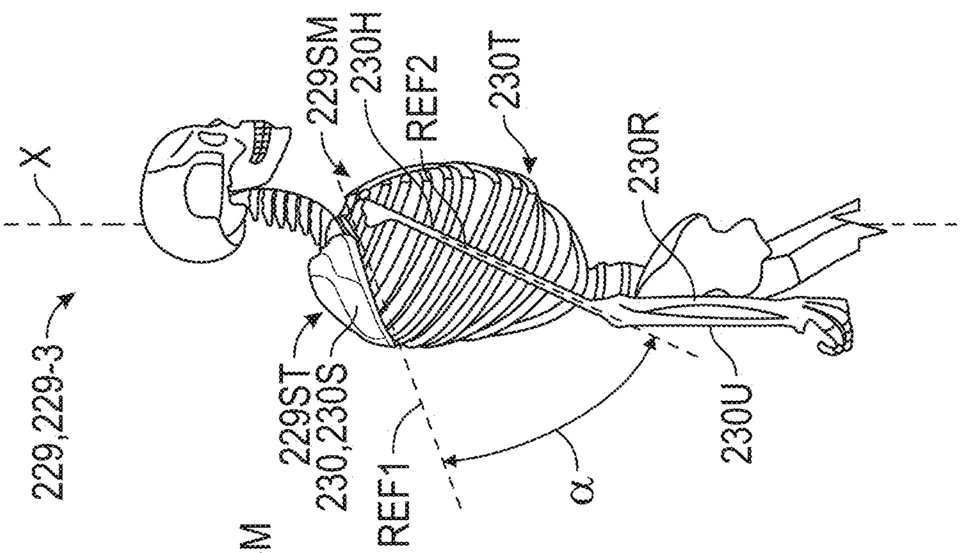

Referring to FIGS. 17A-17C, with continuing reference to FIGS. 15 and 16A-16C, anatomical models 229-1 to 229-3 may be associated with postures of respective patients. Various techniques may be utilized to characterize a posture of the patient. The planning system 10 (FIGS. 1-2) may be configured to determine one or more characteristics associated with a posture of the patient based on an orientation of one or more of the bone models 230 of the anatomical model 229. Bone models 230 of the humerus 230H, ulna 230U and/or radius 230R may be situated at a resting (e.g., starting) angle relative to the scapula model 230S and/or thorax model 230T, including during image acquisition.

The anatomical models 229-1 to 229-3 may establish one or more angles α that may be associated with a posture of the patient anatomy. Various techniques may be utilized to define the angle α. A first bone model 230 associated with a first bone of the patient may extend along a first reference plane REF1. A second bone model 230 associated with a second bone of the patient may extend along a second reference plane REF2. The first and second reference planes REF1, REF2 may intersect to establish the angle α. In implementations, the angle α may be established relative to the first reference plane REF1 and axis X of the patient. The angle α may be associated with a posture of the patient.

A scapular angle associated with the scapula of the patient may be established. The scapular angle can include one or more components relative to an anatomy of the patient (e.g., a set of angles). In implementations, the scapular angle may be defined based on scapular internal rotation, scapular upward rotation and/or scapular interior tilt. The scapular angle may be determined when the patient is standing or situated in a resting (e.g., horizontal) position. In implementations, the first bone model 230 may be a scapula bone model 230S associated with the scapula of the patient. The second bone model 230 may be a humerus bone model 230H associated with the humerus of the patient. The angle α may be defined as an angle between a spine of the scapula and an axis of the humeral diaphysis with respect to a medial plane of the patient. A spine of the scapula model 230S may extend along the first reference plane REF1. A diaphysis of the humeral model 230H may extend along the second reference plane REF2. The spatial module 50 and/or another portion of the planning system 10 may be configured to determine the first and/or second reference planes REF1, REF2 and associated angle α. In implementations, the surgeon or clinical user may interact with the user interface 56 to specify the first and/or second reference planes REF1, REF2.

The anatomical models 229 may include one or more bone models 230 arranged relative to the axis X. The axis X may be a vertical axis associated with a patient in an upright (e.g., standing) position and may be normalized relative to a coordinate system. The anatomical model 229 may include two or more bone models 230 arranged relative to each other to establish the scapular angle. The axis X may extend along one or more of the bone models 230. The axis X may be established along an intersection between the (e.g., sagittal and coronal) kinematic planes of the patient. The first reference plane REF1 may extend along another one of the bone models 230, such as along the spine of the scapula bone model 230S. The first reference plane REF1 may intersect the axis X of the patient to establish the scapular angle. An orientation of the first reference plane REF1 may be established based on an internal rotation, an upward rotation and/or an anterior tilt of the scapula. In implementations, the scapular angle may be a set of values defined relative to the scapula internal rotation, scapula upward rotation and/or scapula anterior tilt. For the purposes of this disclosure, the terms "about," "substantially" and "approximately" mean±10 percent of the stated value or relationship unless otherwise indicated. The humerus bone model 230H, ulna bone model 230U and/or radius bone model 230R may be substantially vertical or may be transverse to the axis X of the patient. In the implementation of FIGS. 17A-17C, the ulna bone model 230U and radius bone model 230R may be substantially parallel to the axis X.

The scapular angles of the anatomical models 229-1 to 229-3 may be the same or may differ from each other. The postures of the respective anatomical models 229-1 to 229-3 may be characterized by a set of posture types (e.g., A, B, C). Each posture type may be assigned a range of values for one or more posture parameters (e.g., characteristics), such as the scapular angle. In implementations, posture type A may be associated with a scapular internal rotation of approximately 32±6 degrees, a scapular upward rotation of approximately −3±6 degrees, and a scapular interior (e.g., anterior) tilt of approximately 23±11 degrees. Posture type B may be associated with a scapular internal rotation of approximately 42±3 degrees, a scapular upward rotation of approximately −12±7 degrees, and a scapular interior tilt of approximately 24±8 degrees. Posture type C may be associated with a scapular internal rotation of approximately 53±5 degrees, a scapular upward rotation of approximately −15±13 degrees, and a scapular interior tilt of approximately 33±7 degrees.

The scapular angles of FIGS. 17A-17C may be associated with the posture types of FIGS. 15 and/or 16A-16C. The anatomical model 229-1 of FIG. 17A may be associated with posture type A of FIGS. 15 and 16A. The anatomical model 229-2 of FIG. 17B may be associated with posture type B of FIGS. 15 and 16B. The anatomical model 229-3 of FIG. 17C may be associated with posture type C of FIGS. 15 and 16C. In implementations, the anatomical model 229-1 may be associated with posture type A and/or a scapular angle having any of the value(s) within the disclosed range(s) associated with posture type A. The anatomical model 229-2 may be associated with posture type B and/or a scapular angle having any of the value(s) within the disclosed range (s) associated with posture type B. The anatomical model 229-3 may be associated with posture type C and/or a scapular angle having any of the value(s) within the disclosed range(s) associated with posture type C.

Figure 18A:
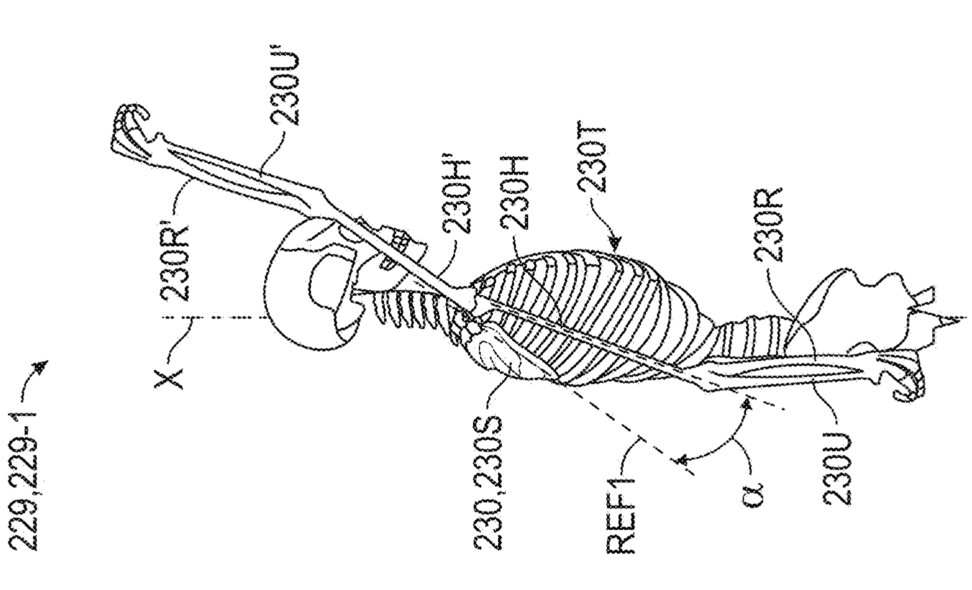
FIGS. 18A-18C disclose the scapular angles associated with the respective posture types of FIGS. 17A-17C with respective models of a humerus and forearm in an elevated position.
Figure 18B:
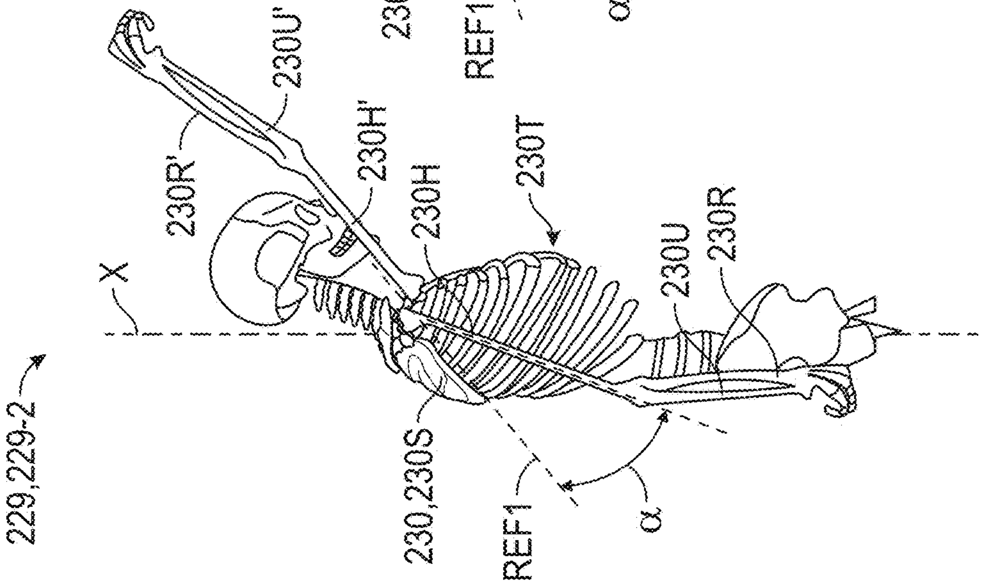
Figure 18C:
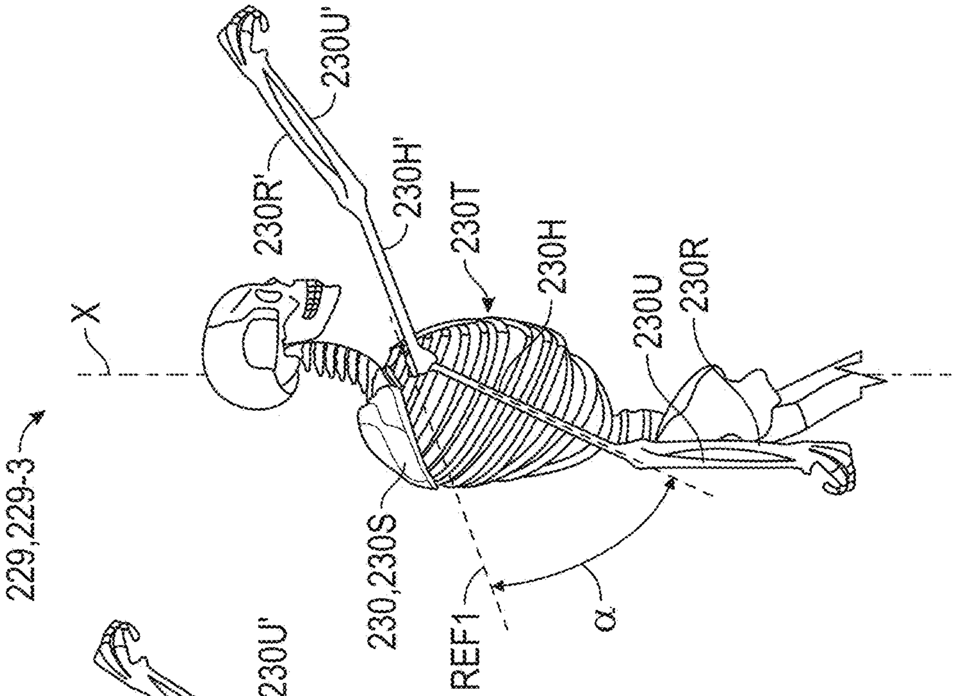

Referring to FIGS. 18A-18C, with continuing reference to FIGS. 17A-17C, the posture of a patient may limit a range of motion of the limb such as the humerus and associated forearm. The anatomical models 229-1 to 229-3 may be associated with instances of the humerus bone model 230H', ulna bone model 230U' and radius bone model 230R' in an elevated position. Range of motion may be characterized by a reference (e.g., scapular) plane REF1 and/or associated scapular angle. Movement of the humerus in an upward direction may generally be limited at approximately the reference plane REF1.

Figure 16D:
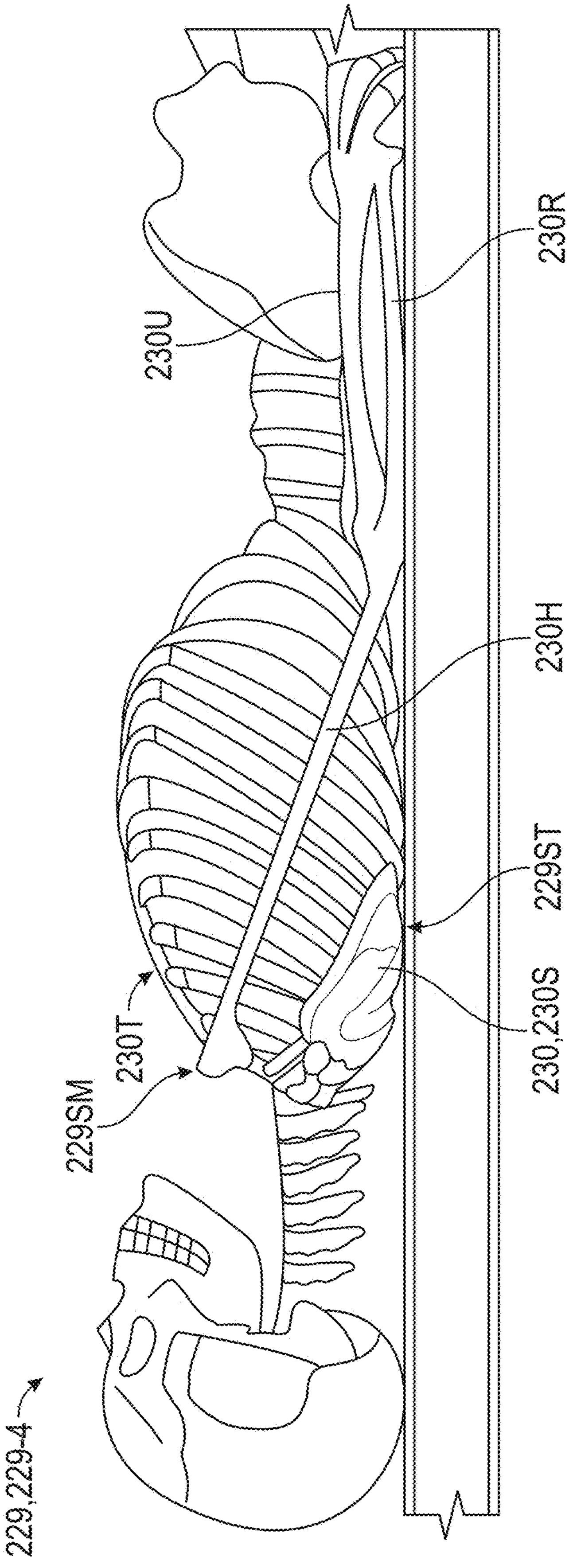
FIG. 16D discloses an anatomical model in a laying position.

Image data associated with the anatomical and bone models 229, 230 may be captured in an acquisition orientation associated with one or more imaging devices 16 (FIGS. 1-2). Each imaging device 16 may be associated with an acquisition reference system. The acquisition reference systems of two or more imaging devices 16 may be the same or may differ from each other. The patient may be positioned relative to a reference point of the acquisition reference system, which may differ between patients based on anatomical makeup, posture, morbidity, etc. The bone models 230 may be in a resting (e.g., starting) position of the patient during acquisition. The resting position may be associated with an upright (e.g., vertical) position or a laying (e.g., horizontal or supine) position of the patient during acquisition of the associated image data. FIG. 16D discloses an anatomical model 229-4. The anatomical model 229-4 may include one or more bone models 230, which may be associated with any of the bones of the anatomy. The anatomical model 229-4 may be associated with a laying (e.g., horizontal) position of the patient (e.g., on a bed of the imaging device) during acquisition of the associated image data. The anatomical model 229-4 may be associated with the same patient as one of the anatomical models 229-1 to 229-3, such as the anatomical model 229-2. An orientation of one or more bones of the patient in an upright position, such as the scapula, humerus and/or thorax, may be determined based on a transformation associated with a laying position of the patient. In implementations, the orientation of the scapula model 230S, humerus model 230H and/or thorax model 230T of the anatomical model 229-2 (FIG. 16B) may be established based on a transformation applied to the orientation of the scapula model 230S, humerus model 230H and/or thorax model 230T of the anatomical model 229-4 (FIG. 16D). An orientation of the scapula may be non-perpendicular to the axes of the acquisition reference system.

The scapula orientation in the acquisition reference system may be characterized by a posture of the patient. A transformation may account for effects on the patient anatomy in the laying position, such as relaxation of the musculature, etc. In implementations, the transformation may include one or more predefined transformation angles. The predefined transformation angles may include three angles of rotation relative to the axes of the reference system. Predefined transformation angles may be established for one or more acquisition positions, such as the laying position and/or upright position. A set of predefined transformation angles may be established for each respective bone of the anatomy. The spatial module 50 may be configured to apply the transformation to the respective bone model(s) 330 to transform the bone model(s) 330 from the laying position to the upright position, or vice versa.

Information relating to the posture of a patient may be incorporated into the systems and methods disclosed herein, such as the system 10 (FIGS. 1-2), to establish a surgical (e.g., preoperative) plan and/or determine and/or validate aspects of range of motion (ROM) associated with the patient utilizing any of the techniques disclosed herein. The system 10 may establish a preoperative plan 36 based on one or more determined posture characteristics (e.g., parameters) associated with the posture of a patient. A position and/or orientation of one or more implants specified in the preoperative plan 36 may be determined based on the determined posture characteristic(s). By incorporating posture information into the systems and methods disclosed herein, the surgeon or clinical user may plan the placement of one or more implants with consideration to the resting (e.g., starting) angle of the shoulder blade ("scapular"). The implant may be assigned a default starting position and/or orientation relative to an adjacent bone. The system 10 may determine a correction value to adjust the default starting position and/or orientation of the implant based on the determined posture characteristic(s). The posture information may be utilized for determining range of motion, including with respect to acts of daily living.

The system 10 may be configured to determine one or more posture parameters associated with a posture of a patient. The system 10 may be configured to adjust an implant plan based on the one or more posture parameters. The implant plan may include any of the parameters disclosed herein, such as implant type, implant dimension and implant position.

Figure 19:
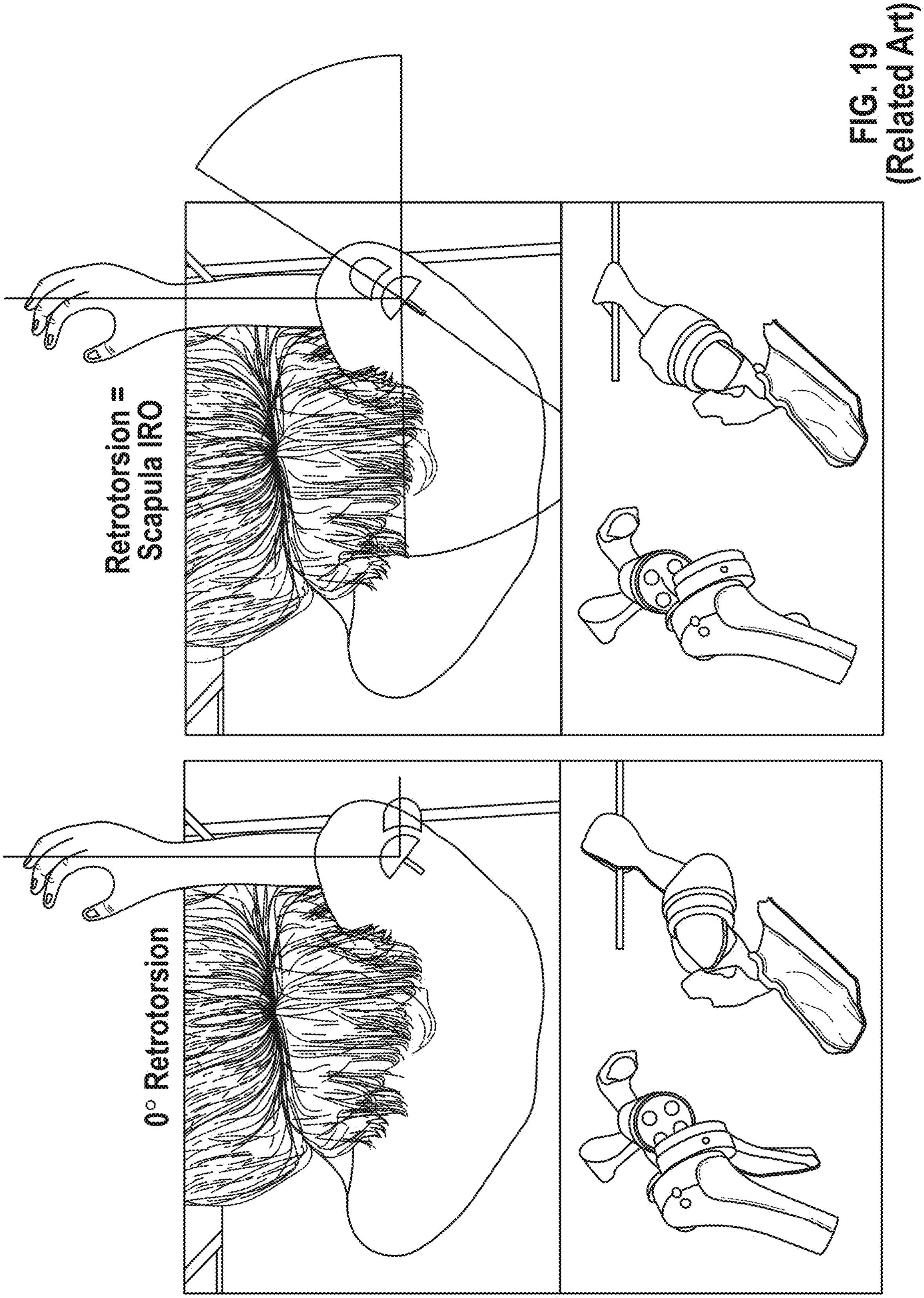
FIG. 19 (Related Art)
FIGS. 19-20 disclose a clinical example utilizing the techniques disclosed herein.
Figure 20:
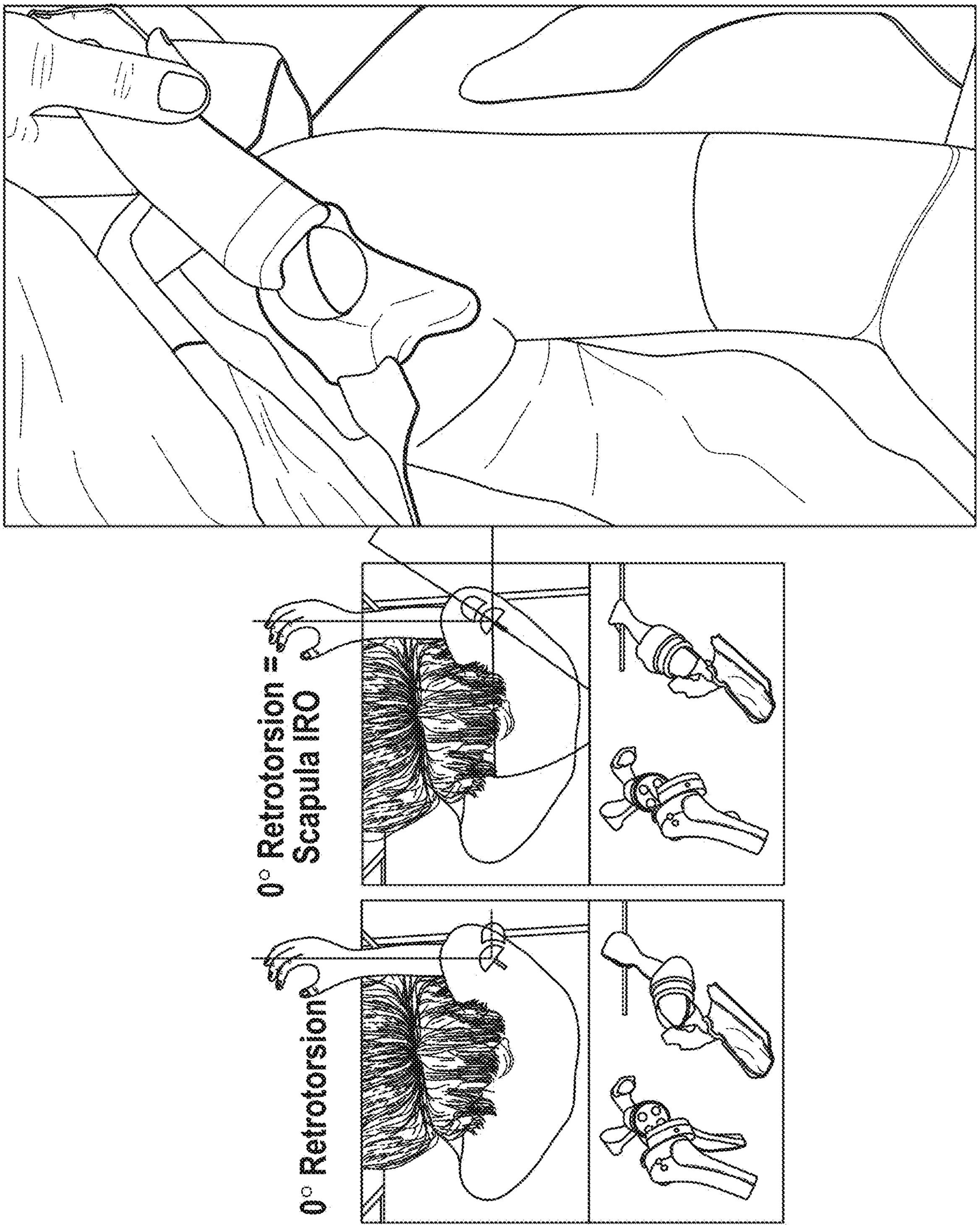
FIG. 20 (Related Art)

Referring to FIGS. 19-20, the posture of a patient may affect retrotorsion as disclosed in Moroder, P., et al. (2022). Patient Posture Affects Simulated ROM in Reverse Total Shoulder Arthroplasty: A Modeling Study Using Preoperative Planning Software. Clin Ortop Relat Res (2022) 480: 619-631. FIGS. 19-20 disclose a clinical example of a shoulder arthroplasty for a patient. An orientation of an implant associated with a humerus may be adjusted to vary retrotorsion from 0 degrees to a value equal to an internal rotation of the scapula (IRO). Setting the orientation of the implant to the internal rotation of the scapula (IRO) may achieve a relatively greater range of motion and/or reduce a likelihood of impingement of the implant.

In implementations, a posture transformation may be established. The posture transformation may be based on a posture classification and/or one or more measured posture parameters, including any of the posture parameters disclosed herein. Posture parameters may include one or more landmarks of the scapula, a distance or relative position between two or more landmarks, a scapular angle, and/or a dimension of one or more bones of the anatomy (e.g., length of humerus). In implementations, the posture transformation may be utilized to adjust or otherwise set a planned implant position and/or orientation to treat the patient, which may improve range of motion and acts of daily living.

One or more range of motion parameters may be utilized to establish the posture transformation. In implementations, the parameters may be associated with one or more acts of daily living and/or lifestyle goals (e.g., desired post-surgery range of motion for abduction, adduction, external rotation, internal rotation, upward rotation, extension, flexion, external rotation combined with 60° abduction, internal rotation with 60° abduction, etc.). Defined values of the one or more acts of daily living and/or lifestyle goals may be utilized as criteria for establishing the posture transformation.

The system 10 may be configured to perform a range of motion simulation based on one or more parameters associated with a posture of a patient. A storage system 18 may be configured to store range of motion data derived from the range of motion simulation. The parameters may include a scapular angle associated with a scapula of the patient.

Methods may include performing a range of motion simulation based on one or more parameters associated with a posture of a patient. A method may include storing range of motion data derived from the range of motion simulation within a storage system 18 of the surgical planning system 10. The parameters may include a scapular angle associated with a scapula of the patient. In implementations, the parameters may include a humeroscapular contribution and/or a scapulothoracic contribution to the range of motion of the humerus.

In implementations, the planning environment 28 may be operable to receive image data associated with the patient. The planning environment 28 may be operable to generate the scapula, thorax and humerus models based on the image data. The planning environment 28 may be operable to position at least one implant model relative to a shoulder joint model. The planning environment 28 may be operable to determine an overall range of motion of a humerus model relative to one or more kinematic planes based on the position of the at least one implant model. The overall range of motion may be based on a humeroscapular contribution of humeroscapular movement between the humerus model and the scapula model and a scapulothoracic contribution of scapulothoracic movement between the scapula model and the thorax model. The planning environment 28 may be operable to determine a numerical relationship between the humeroscapular contribution and the scapulothoracic contribution for at least one position relative to the overall range of motion. The planning environment 28 may be operable to establish a surgical plan associated with the overall range of motion based on the numerical relationship. The planning environment 28 may be operable to display the numerical relationship in a user interface. The numerical relationship may be established utilizing any of the techniques disclosed herein.

Referring to FIGS. 21-26, with continuing reference to FIG. 2, the planning system 10 may be configured to display a selected anatomical model 329 in one or more display windows 360 of a graphical user interface 356. The anatomical model 329 may include one or bone models 330, which may be associated with respective joint(s). The display module 48 may be configured to display the anatomical model 329 in the display window(s) 360. The spatial module 50 may be configured to adjust a position of one or more bone models 330 relative to each other, another portion of the anatomical model 329, and/or a reference system.

Figure 24:
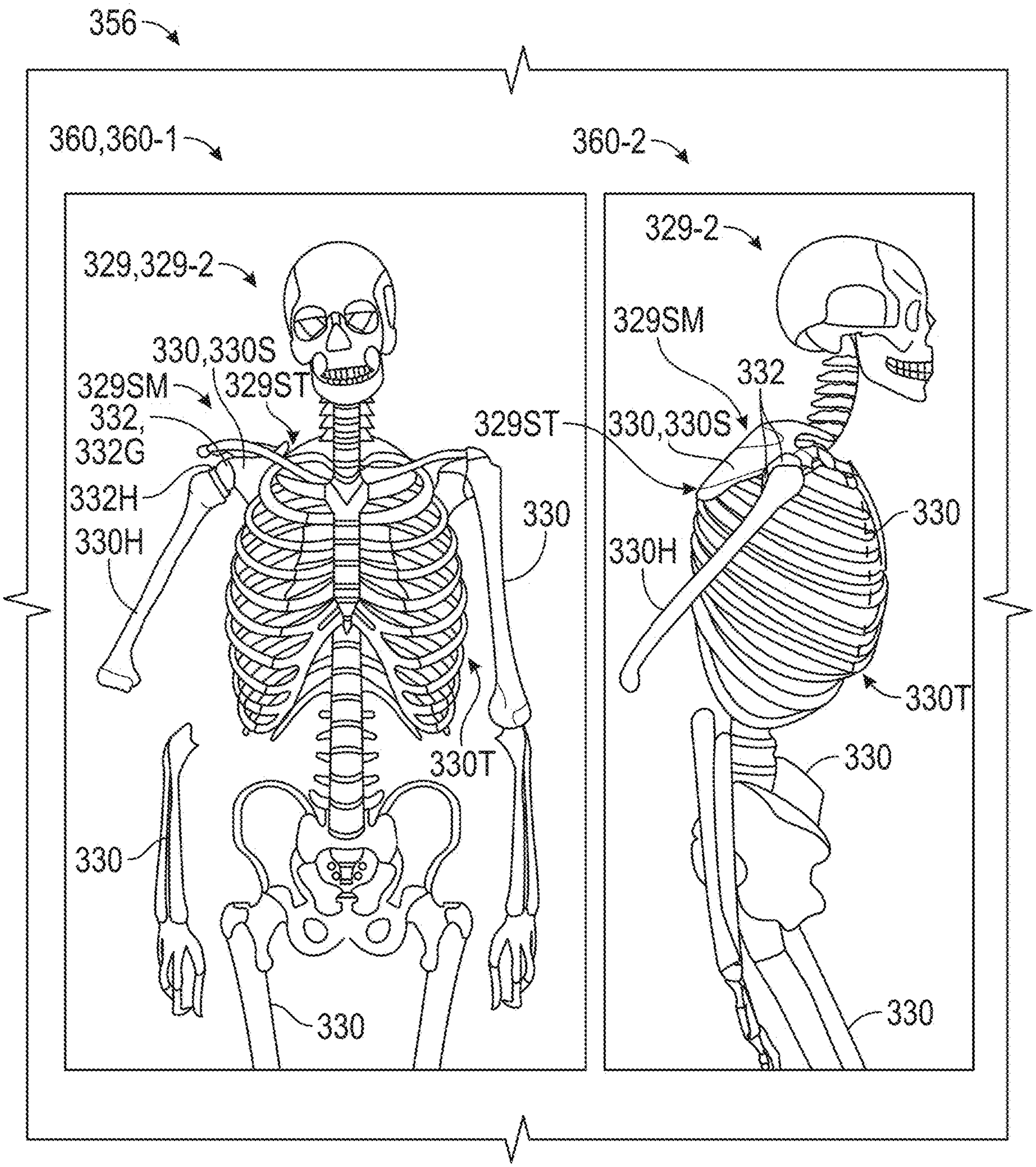
FIGS. 24-26 disclose another anatomical model of a patient.
Figure 25:
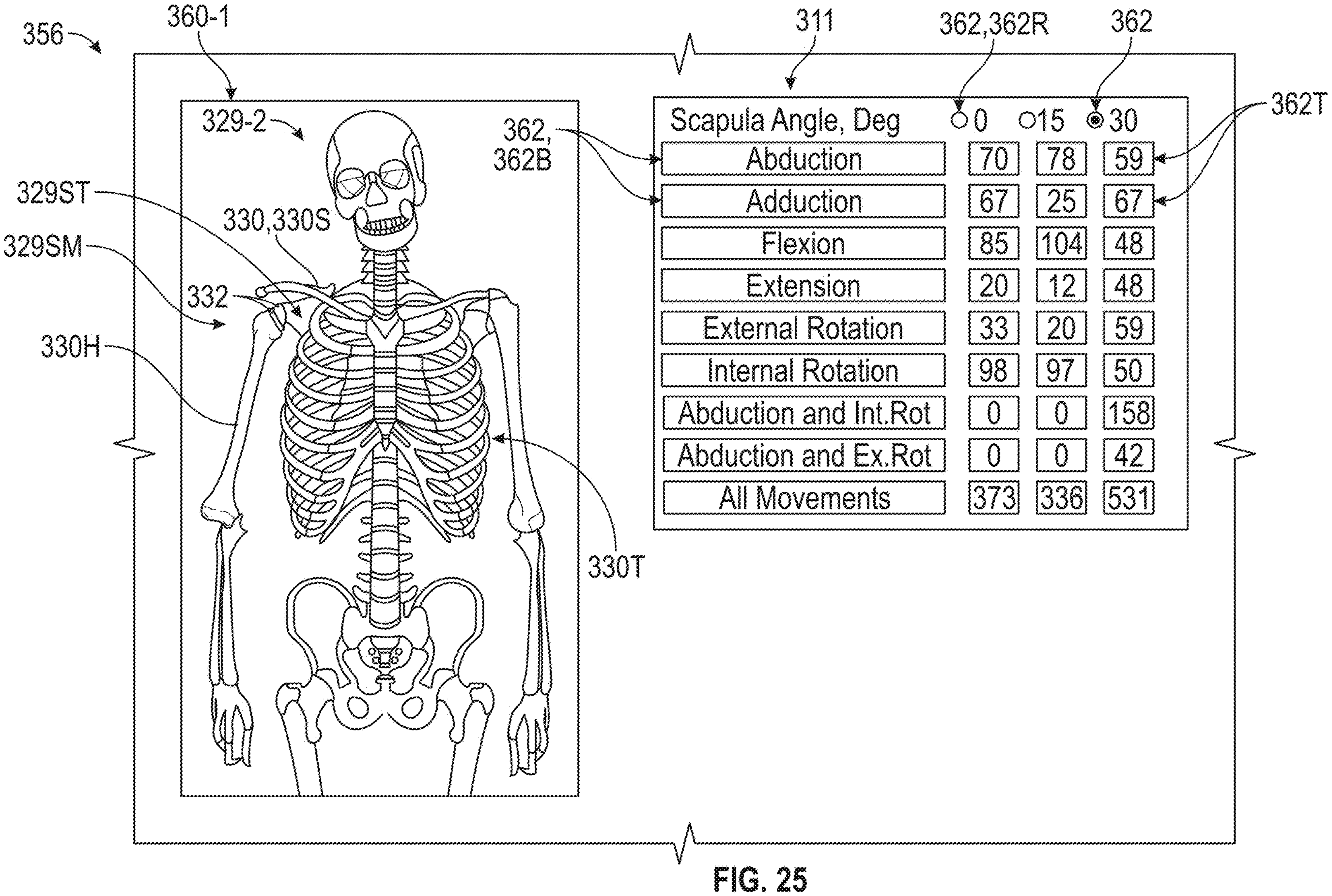
Figure 26:
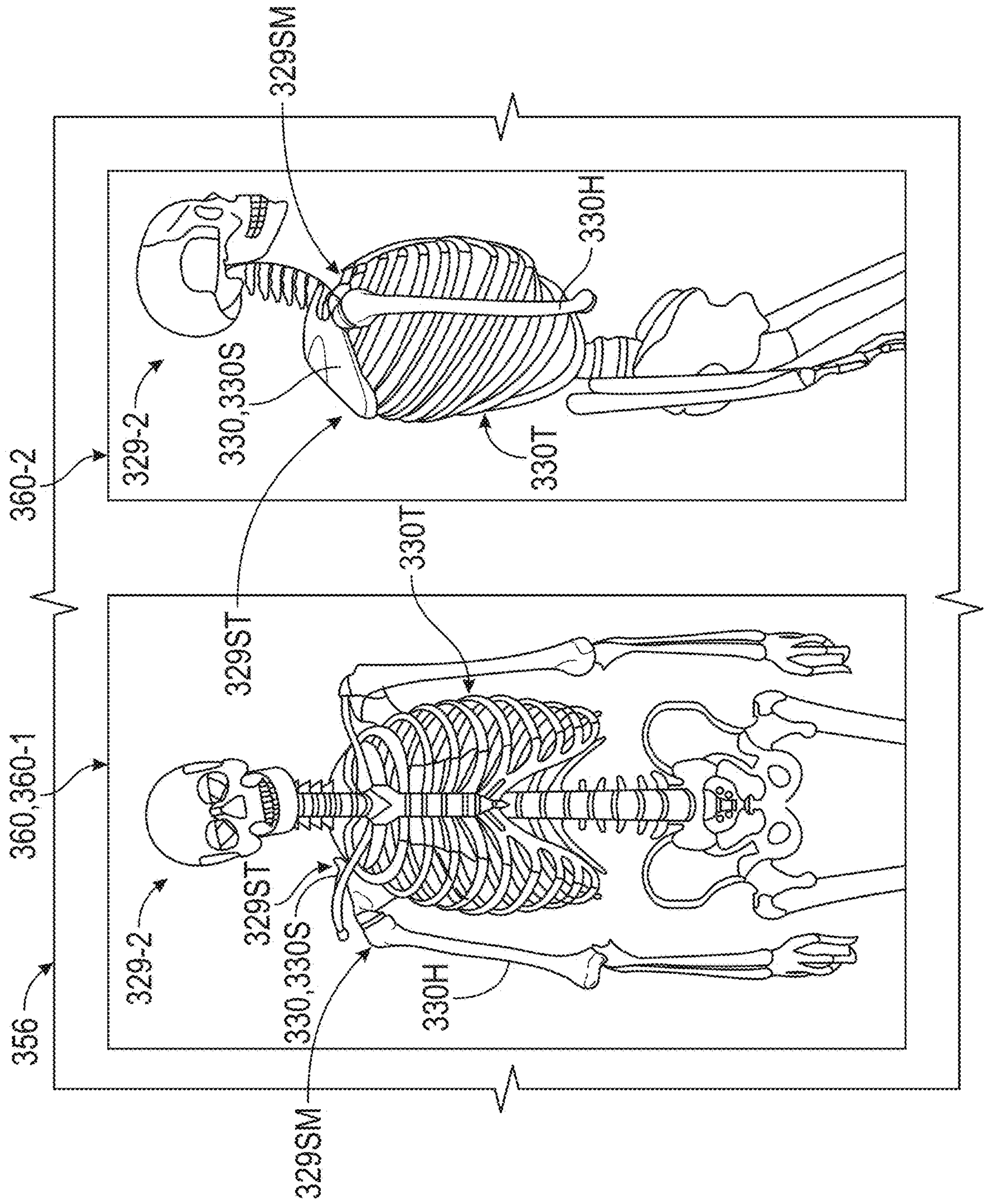

The anatomical models 329 may be associated with one or more patients. The anatomical models 329 may include a first anatomical model 329-1 (FIGS. 21-23) and/or a second anatomical model 329-2 (FIGS. 24-26). The anatomical model 329 may include a shoulder joint model 329SM and one or more implant models 332 associated with various postures and scapular angles of the anatomy. The shoulder model 329SM may include a scapula bone model 330S and a humeral bone model 330H. The anatomical model 329 may include a scapulothoracic joint model 329ST associated with a scapulothoracic joint. The scapulothoracic model 329ST may include the scapula bone model 330S and a thorax bone model 330T. The thorax model 330T may include a single bone model 330 or a set of bone models 330 representative of various bones of the thorax, including a sternum, one or more thoracic vertebrae, and/or one or more ribs.

The spatial module 50 may be configured to arrange one or more implant models 332 relative to each other and/or the anatomical model 329. The implant models 332 may include a first (e.g., glenoid) implant model 332G and a second (e.g., humeral) implant model 332H. The implant models 332G, 332H may mate with each other. The scapula model 330S, anatomical model 329, glenoid implant model 332G and/or humeral implant model 332H may be associated with various postures and scapular angles. Various parameters may be associated with the scapular angle, such as abduction, adduction, flexion, extension, external rotation, internal rotation, upward rotation, abduction and internal rotation and abduction and external rotation. Values may be assigned to each of the parameters and may be displayed to the user. A summation of the values may be displayed to the surgeon or clinical user in the user interface 356 (e.g., FIGS. 22 and 25). A posture transformation may be applied to adjust a default starting position and/or orientation of the implant model(s) 332 based on the determined parameters.

The user interface 356 may include a first display window 360-1 and a second display window 360-2. The display module 48 may be configured to cause the user interface 356 to display different anatomical views in the display windows 360-1, 360-2. In implementations, the display module 48 may be configured to cause the first display window 360-1 to display an anterior (or posterior) view of the anatomical model 329-1. The display module 48 may be configured to cause the second display window 360-2 to display a lateral view of the anatomical model 329-1. The spatial module 50 may be configured to set a position of the bone models 330 relative to each other and/or a reference system based on a determined posture of the patient. The surgeon or clinical user may interact with the display windows 360 and/or another portion of the user interface 356 to select one or more of the bone models 330. The display module 48 may be configured to establish a visual contrast between the selected bone model(s) 330 and any remaining bone models 330 and/or other portions of the anatomical model 329.

Figure 21:
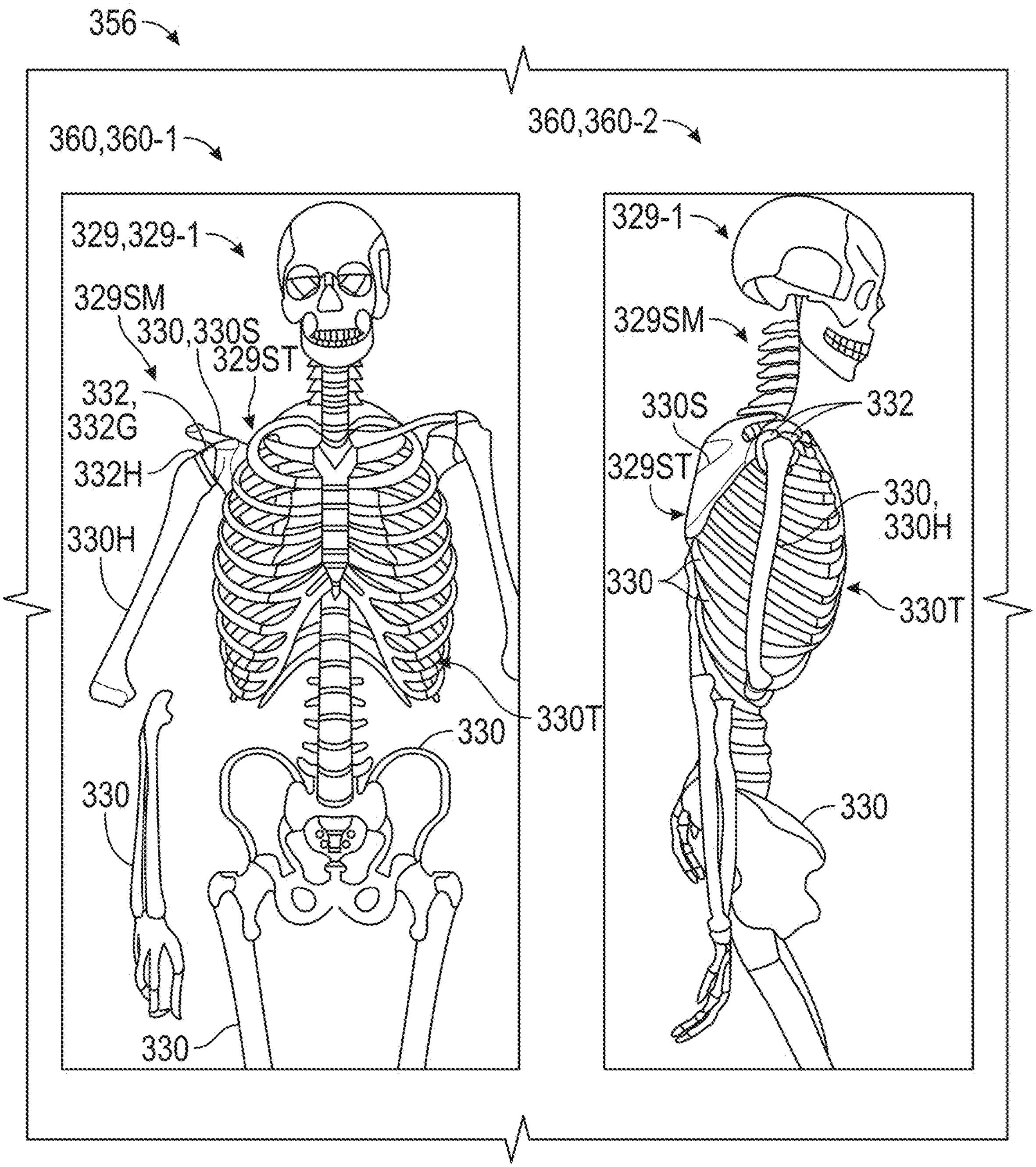
FIGS. 21-23 discloses an anatomical model of a patient.
Figure 22:
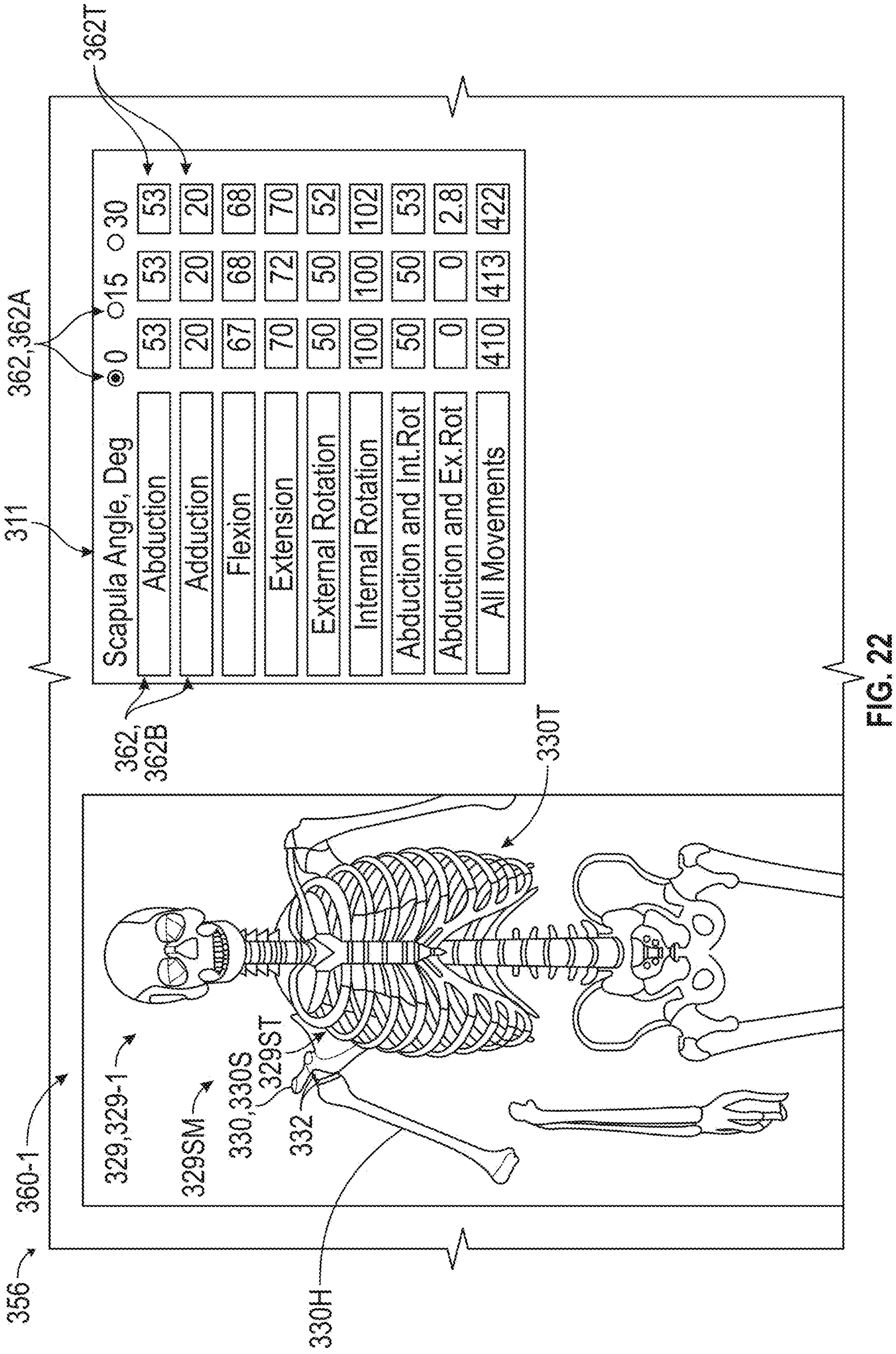

Referring to FIG. 22, with continuing reference to FIGS. 2 and 21, the spatial module 50 may be configured to adjust a position of the selected bone model(s) 330 relative to each other and/or another portion of the anatomical model 329-1. The user interface 356 may include one or more (e.g., interactive) objects 362. The objects 362 may be arranged in a control panel 311. The objects 362 may include buttons 362B, radial buttons 362R and/or text boxes 362T. The text boxes 362T may be configured to display one or more values associated with the anatomical model 329-1. The surgeon or clinical user may adjust one or more of the values displayed in the text boxes 362T in response to selecting the respective text box 362T, button 362B and/or radial button 362R. The buttons 362B, 362R may be associated with various characteristics (e.g., angular relationships) of the selected bone model 330, including any of the characteristics disclosed herein. In implementations, the characteristics may include abduction, adduction, flexion, extension, external rotation, internal rotation, upward rotation, abduction and internal rotation, abduction and external rotation, and/or all movements. The text boxes 362T associated with all movements may be configured to display summations of values for text boxes 362T in the respective columns. The surgeon or clinical user may specify values in one or more of the text boxes 362T to adjust a position and/or orientation of one or more of the selected bone models 330. The surgeon or clinical user may interact with the display window 360 to adjust a position and/or orientation of one or more selected bone models 330 and any associated values in the control panel 311. The display windows 360 and control panel 311 may be dynamically linked such that changes to one may cause respective changes to the other, including values specified in the text boxes 362T.

Figure 23:
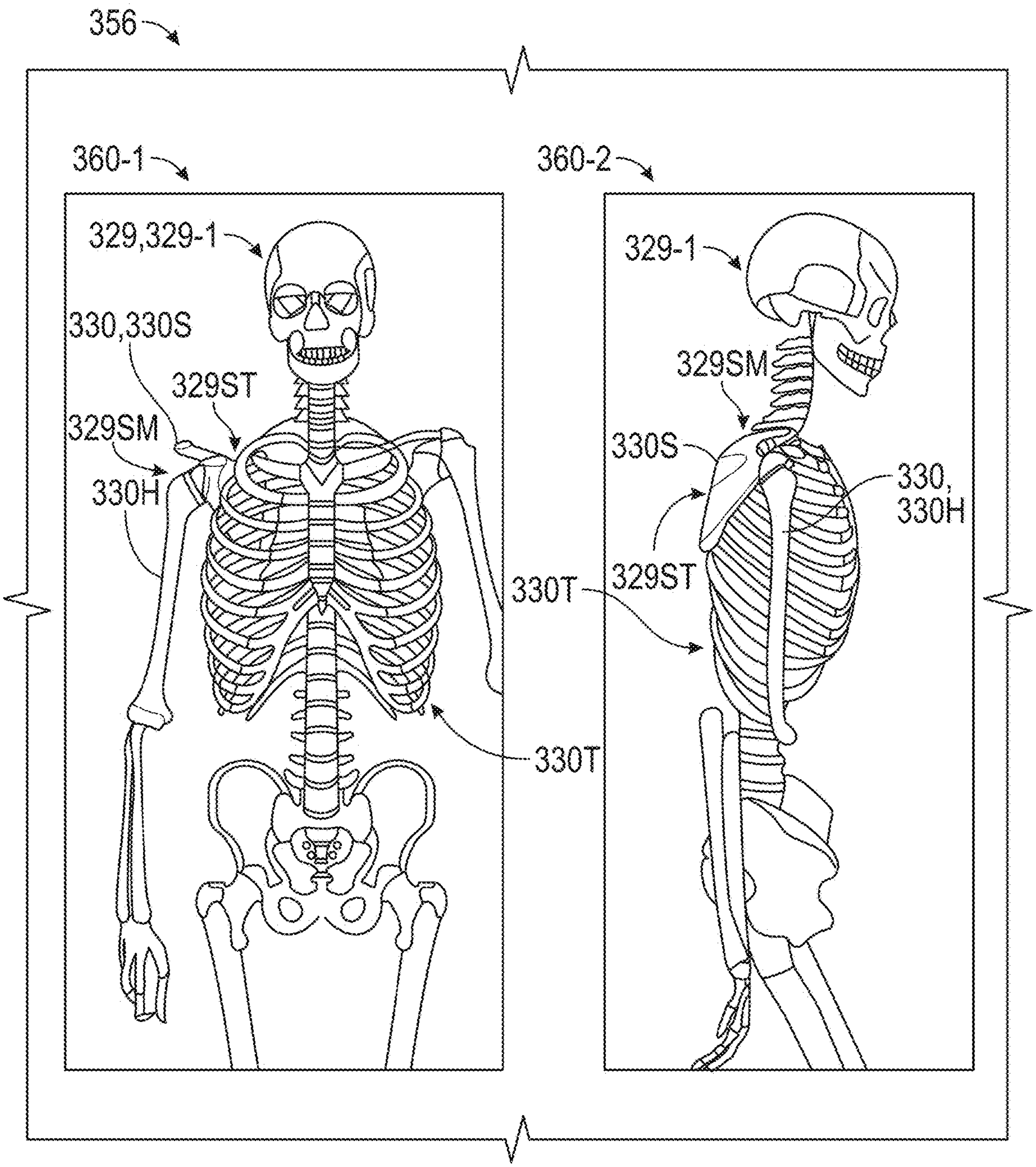

In the implementation of FIGS. 21-23, the anatomical model 329-1 may be associated with a scapular angle (e.g., interior tilt) of 0 degrees. The spatial module 50 may be configured to assign default values for each of the characteristics associated with the objects 362 of the control panel 311 based on a determined and/or selected scapular angle. The spatial module 50 may be configured to arrange the selected bone model(s) 330 relative to each other based on the assigned values. A posture associated with the scapular angle and anatomical model 329-1 of FIG. 21 may be assigned a posture type (e.g., type A).

Referring to FIG. 23, with continuing reference to FIG. 22, the surgeon or clinical user may interact with one or more of the objects 362 to adjust a position of the selected bone model(s) 330, such as the humeral model 330H. The surgeon or clinical user may interact with one or more of the objects 362 to adjust an adduction of the humeral model 330H from a first position (e.g., FIG. 22) to a second position (e.g., FIG. 23). The spatial module 50 may be configured such that unselected bone model(s) 330 may remain in a fixed position during adjustment of the selected bone model(s) 330, which may provide flexibility in determining one or more parameters of a preoperative plan, such as a position and/or orientation of implant(s) associated with respective implant model(s) 332. The surgeon or clinical user may interact with the user interface 356 to observe the effect of the various characteristics with respect to range of motion and one or more acts of daily living and/or lifestyle goals, including any of those disclosed herein.

FIGS. 24-26 disclose an implementation of a second anatomical model 329-2 in the display windows 360 of the graphical user interface 356. A posture associated with the second anatomical model 329-2 may differ from a posture associated with the first anatomical model 329-1. The anatomical model 329-2 may be associated with a scapular angle (e.g., interior tilt) of approximately 30 degrees. A posture associated with the scapular angle and anatomical model 329-2 of FIG. 24 may be assigned a posture type (e.g., type C).

The planning environment 28 may be configured to establish surgical plans 36 based on the determined postures and/or scapular angles of respective patients. The planning environment 28 may be configured to determine posture and/or scapular angle based on an acquisition position of the patient (e.g., upright or laying position). The planning environment 28 may be configured to apply a transformation to the acquisition position of the patient to predict or otherwise determine the posture and/or scapular angle of the patient in an upright (e.g., standing) position. The surgeon or clinical user may interact with the planning system 10 to establish a surgical plan 36 based on the determined posture and/or scapular angle to achieve one or more acts of daily living and/or lifestyle goals and/or evaluate range of motion with respect to planned implant positioning, which can improve mobility of the patient.

Figure 27:
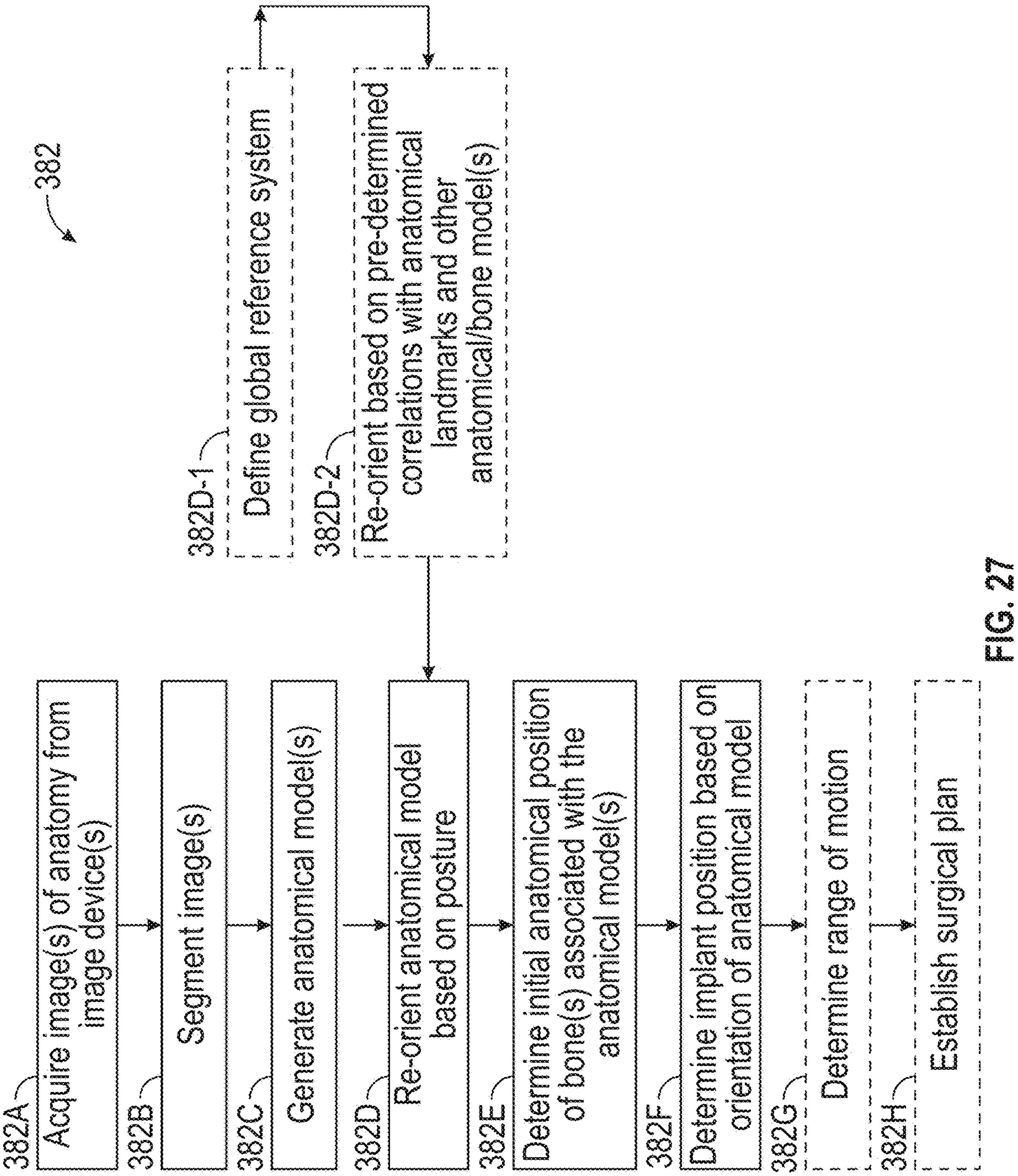
FIG. 27 discloses a method for planning a surgical procedure on a respective patient using a surgical planning system.

FIG. 27 discloses a method for a surgical procedure in a flowchart 382. The method 382 may be utilized to pre-operatively plan, implement, evaluate and/or validate aspects of various surgical procedures, such as an arthroplasty for restoring functionality to shoulders, ankles, knees, hips and other joints. The method 382 may be utilized with any of the planning systems and methods, virtual anatomical models and/or bone models disclosed herein, such as the planning system 10. The method 382 may be utilized to determine a posture of the patient. The method 382 may be utilized to establish a position and/or orientation of one or more implants based on an orientation of the anatomy, such as an orientation of the scapula and/or thorax. The orientation of the anatomy may be associated with a posture of a patient.

The planning method 382 may be utilized to predict or otherwise determine a position, alignment and/or angle of a bone based on a geometry of one or more other bones, including adjoining bone(s) and/or non-adjoining bones of the patient. The method 382 may be utilized to predict or otherwise determine the position, alignment and/or angle of the bone based on a relationship of the bone to a (e.g., global) reference system and/or one or more kinematic planes and/or axes of the patient. The method 382 may be utilized to determine a range of motion of one or more bones of the anatomy, such as the humerus. Fewer or additional steps than are recited below could be performed within the scope of this disclosure, and the recited order of steps is not intended to limit this disclosure. The system 10 and any of the associated modules may be configured to implement the features of any of the methods disclosed herein, including method 382. Reference is made to the system 10.

Referring to FIGS. 2 and 27, at step 382A digital imagery of anatomy of a patient may be captured or otherwise obtained by an imaging device 16 (FIGS. 1-2), including any of the imaging devices disclosed herein such as a computed tomography (CT) or magnetic resonance imaging (MRI) device. The digital imagery may include image data which may be captured or otherwise obtained to establish one or more images 26 of the anatomy, such as with the imaging device 16. The data module 46 may be configured to receive the image data directly from the imaging device 16 or may acquire the image data by accessing the record or entry associated with the patient from the database 38 (FIG. 2) and/or the patient profile database 64 (FIG. 3). The digital imagery may include any of the anatomy disclosed herein, such as anatomy represented by the bone models 330 and/or anatomical models 329 of FIGS. 21-23. The imaging device 16 may be associated with an acquisition reference system. The acquisition reference system may be associated with axes and a set of coordinate values. The images 26 may be associated with the acquisition reference system of the respective imaging device 16.

Figure 28:
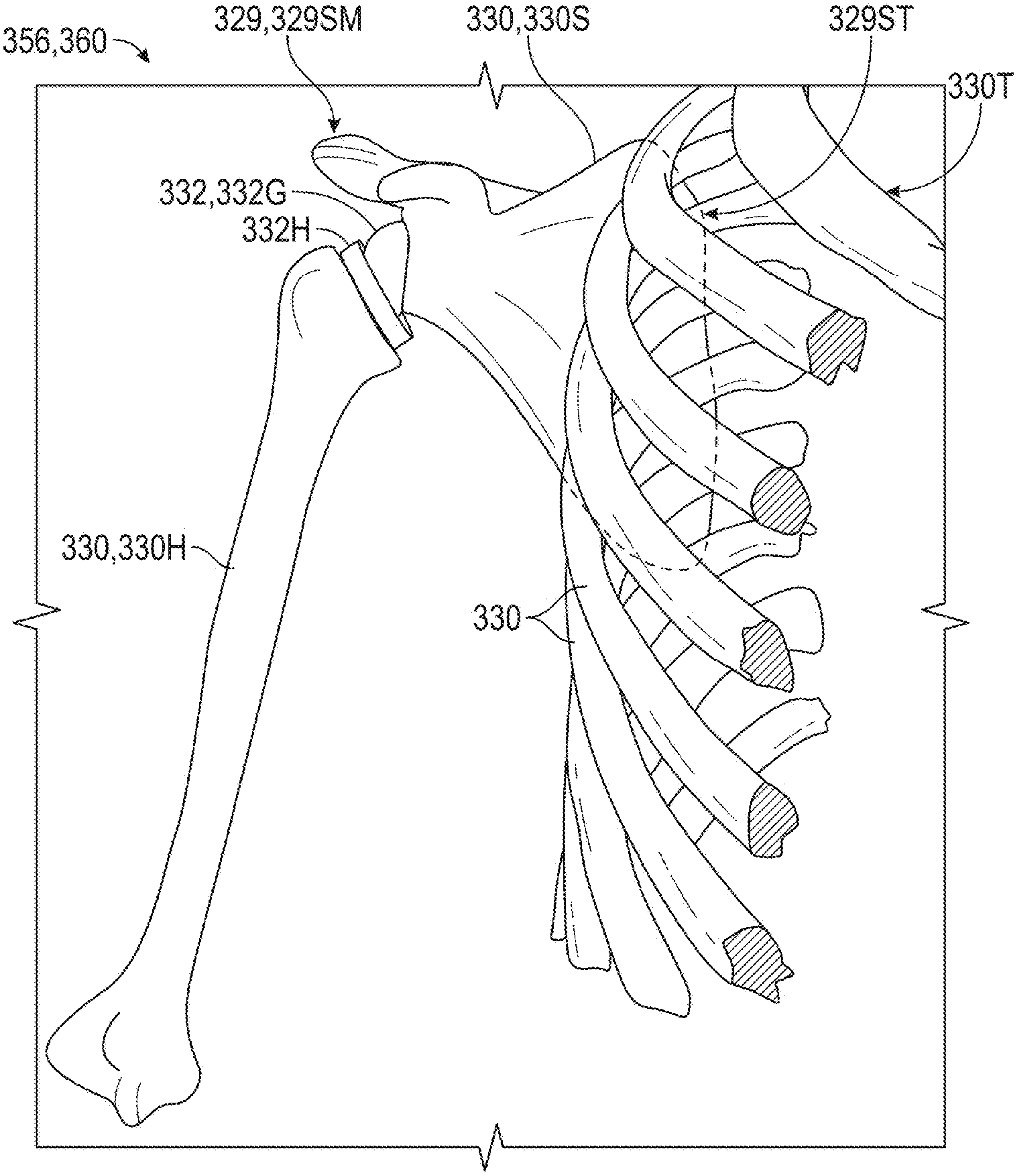
FIGS. 28-32 discloses an anatomical model of a patient associated with a shoulder joint and/or a scapulothoracic joint.

Referring to FIG. 28, with continuing reference to FIGS. 2 and 27, the images 26 may be associated with an anatomical model 329 and/or bone model(s) 330. The spatial module 50 may be configured to associate the anatomical model 329 with the acquisition reference system. Although FIG. 28 discloses the anatomical model 329 relative to a set of implant models 332, the implant models 332 may be positioned relative to the anatomical model 329 subsequent to establishing a modified instance of the anatomical model 329 associated with a surgical plan 36. The data module 46 may be configured to store an instance of one or more anatomical and bone models and associated coordinate values in the memory 44, such as the anatomical model 329 and/or bone models 330.

The digital imagery may be captured relative to various acquisition positions of a patient with respect to the imaging device 16. The acquisition position of the patient may be generally horizontal. In implementations, the acquisition of the patient may be substantially vertical. Imagery of the patient may be captured while the patient is standing. A posture of the patient in the standing position may deviate from a perfect posture. The imagery may be captured by a standing imaging device.

At step 382B, the digital image(s) 26 may be segmented utilizing various techniques, such as by applying automatic, semi-automatic or manual segmentation to the images 26. The system 10 may be configured to segment the images 26.

At step 382C, one or more anatomical and/or bone models may be generated. The system 10 may be configured to generate one or more anatomical models 29, such as the anatomical model 329. The anatomical model 329 may include one or more bone models 330. The anatomical model 329 may include coordinates and/or information specifying an arrangement of the bone models 330 relative to each other.

The anatomical model 329 may include a shoulder model 329SM and/or a scapulothoracic model 329ST. The shoulder model 329SM and/or scapulothoracic model 329ST may be associated with the first anatomical model 329-1 of FIGS. 21-23. The bone models 330 may include a scapula bone model 330S associated with a scapula of a patient and a humeral bone model 330H associated with a humerus of the patient. The shoulder model 329SM may include the scapula bone model 330S and the humeral bone model 330H. The bone models 330 may include a thorax bone model 330T associated with a thorax. The thorax model 330T may include a single bone model 330 or may include two or more bone models 330 associated with various bones of the thorax arranged relative to each other, including any of the bones disclosed herein. The scapulothoracic model 329ST may include the scapula bone model 330S and thorax bone model 330T, which may be associated with a scapulothoracic joint.

In implementations, 3D meshes of a scapula, humerus and/or thorax may be reconstructed to establish the scapula bone model 330S, humerus bone model 330H and/or thorax bone model 330T. The scapula model 330S may be established with respect to a local (e.g., scapula) reference system. The local reference system may be associated with a set of coordinate values. The spatial module 50 may be configured to associate the scapula reference system with a scanned (e.g., acquisition) position of the scapula relative to the imaging device 16.

Various techniques for orienting the anatomy, including the scapula and/or thorax, may be utilized. The anatomy including the scapula and/or thorax may remain in a local (e.g., acquisition) orientation for planning. The acquisition orientation may be associated with the acquisition reference system of the imaging device 16. In implementations, the Z-axis of the acquisition reference system may be horizontal for imaging device 16 and other acquisition systems that may acquire image data of a patient in a horizontal (e.g., laying) position. The Z-axis of the acquisition reference system may be vertical for acquisition systems that may acquire image data of a patient in an upright (e.g., vertical or standing) position. Posture characteristics of the patient may differ between the horizonal and upright positions, such as scapula angle and/or a curvature of vertebrae associated with the thorax.

At step 382D, an orientation and/or position of one or more (e.g., first) bones of the patient may be determined, such as a scapula and/or thorax. The bone(s) may be associated with an anatomical model(s), such as the anatomical model 329. The bone(s) may be associated with a respective bone model, such as the scapula bone model 330S and/or thorax bone model 330T. Various techniques for determining scapular and/or thoracic orientation may be utilized, including any of the techniques disclosed herein.

Step 382D may include re-orienting (e.g., registering) the anatomical model and/or bone model(s) from a first reference system to a second, different reference system. In implementations, the anatomical models and/or bone models may be re-oriented based on a posture of the patient and associated posture characteristics. Although the techniques disclosed herein relating to posture refer to a scapula and/or thorax of a patient, the teachings herein may be utilized to determine range of motion and/or establish or adjust a preoperative plan for other bones and joints. Re-orienting the anatomical models and/or bone models of the patient based on posture may improve implant planning to achieve range of motion and acts of daily living and/or lifestyle goals. The acquisition position of the patient anatomy including the scapula and/or thorax may be determined directly from the digital imagery. The disclosed systems and methods may normalize and/or realign the scapula to a scapular plane in a three dimensional (3D) computer-aided design (CAD) model. One or more measurements and/or other information associated with the patient may be captured preoperatively to manually and/or optically determine the preoperative posture of the patient. In other implementations, re-orienting (e.g., registering) the anatomical model(s) and/or bone model(s) from the first reference system to the second reference system at step 382D may occur without determining the posture of the patient.

The spatial module 50 or another portion of the planning system 10 may be configured to re-orient (e.g., register) at least one or more of the anatomical models and/or bone models from the first reference system to the second reference system. The first reference system may be a local or acquisition reference system. The second reference system may be any of the reference systems disclosed herein, such as a global reference system. The spatial module 50 may be configured to re-orient the bone model 330 in the global reference system based on a selected representative bone model 30, which may be associated with a different patient. The spatial module 50 may be configured to register one or more of the bone models 330 of the patient from the first reference system to the second reference system in response to adjusting one or more coordinate values associated with the respective bone model(s) 330 based on a posture of the patient, including any of the posture parameters disclosed herein. The comparison module 52 may be configured to determine the posture parameter(s) associated with the posture of the patient. The spatial module 50 may be configured to register the bone model 330 of the patient in the global reference system based on the determined posture parameter(s).

The planning system 10 may be configured to normalize one or more data sets in the global reference system, including any of the anatomical models, bone models, implant models and/or databases disclosed herein. Step 382D may include re-orienting the scapula model 330S and/or thorax model 330T from its acquisition orientation in the acquisition reference system to the global reference system. The scapula model 330S and/or thorax model 330T may be re-oriented utilizing any of the techniques disclosed herein. An orientation of the scapula model 330S and/or thorax model 330T in the global reference system may be associated with an anatomical position of the scapula and/or thorax when the patient may be standing, which may be influenced by the posture of the patient.

Various techniques may be utilized to re-orient the anatomical models and/or bone models. The spatial module 50 and/or another portion of the system 10 may be configured to register the bone model(s) from the first (e.g., local or acquisition) reference system to the second (e.g., global) reference system based on one or more posture parameters associated with the posture of the patient. The posture parameters may be utilized to establish a transformation between the first reference system and the second reference system. The posture parameters may include a scapular angle associated with a scapula and/or a curvature of the vertebrae (e.g., FIGS. 17A-17C). Various techniques may be utilized to establish the transformation, such as one or more parametric equations and/or matrices.

Figure 30:
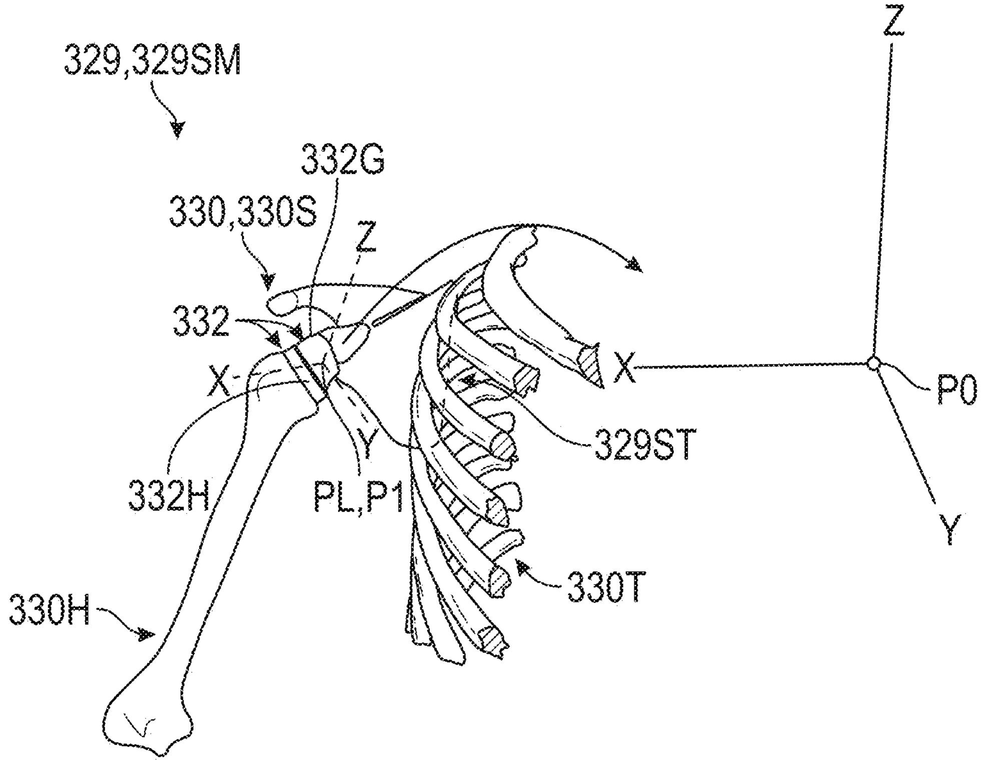

At step 382D-1, a global (e.g., common) reference system may be defined (e.g., FIG. 30). The planning system 10 may define the global reference system utilizing any of the techniques disclosed herein. The global reference system may be associated with a set of coordinate values. The global reference system may be representative of an anatomical position of the patient, which may differ from an acquisition position associated with the image data acquired by the imaging device 16. The anatomical position may correspond to a posture of the patient in an upright (e.g., standing) position. The global reference system may be established with respect to Z (0, 0, 1), Y (0, 1, 0) and X (1, 0, 0) axes. The Z axis of the global reference system may correspond to a vertical direction. The X and Y axes of the global reference system may extend in respective horizontal directions along a horizontal plane. The global reference system may be associated with an upright position of the patient. In implementations, the global reference system may be established with respect to one or more kinematic planes of a patient, including any of the kinematic planes disclosed herein. The X, Y and Z axes may be established along respective kinematic planes of the patient. Utilizing the techniques disclosed herein, acts of daily living and/or lifestyle goals may be established and/or evaluated based on a posture of the patient. The planning system 10 may be configured to establish and/or evaluate implant position and orientation, range of motion and/or acts of daily living/lifestyle goals of a patient relative to the global reference system. In implementations, the range of motion modeler 101 (FIG. 8) may determine range of motion relative to the global reference system. The various databases disclosed herein may be normalized to the global reference system, including the surgical outcomes database 66, range of motion database 68 and/or AMC database 70 (FIG. 3).

The spatial module 50 may be configured to register the scapula reference system associated with the scapula model 330S to the global reference system, which may include translating and/or rotating the scapula model 330S. The scapula reference system may be established relative to a set of landmarks of the scapula model 330S associated with the scapula, such as three or more landmarks.

Figure 29:
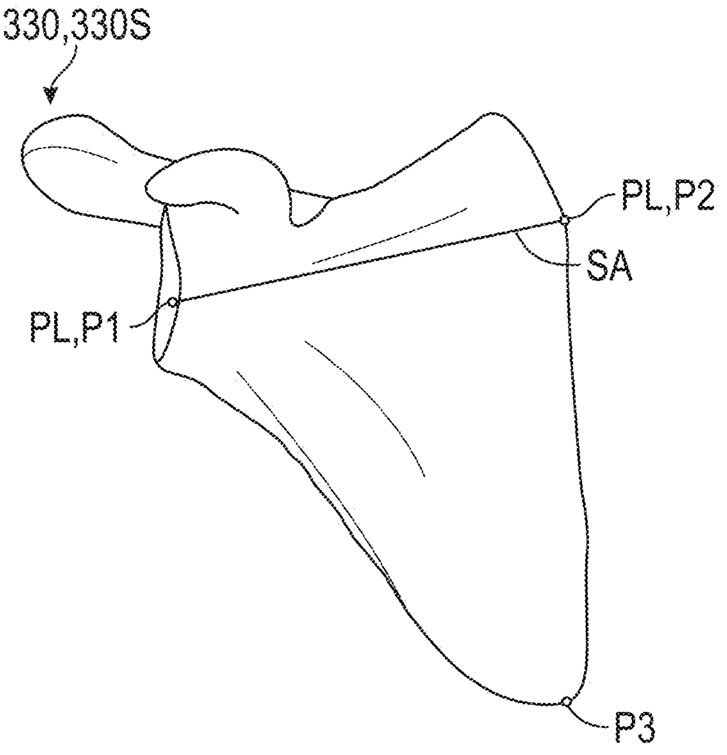

Referring to FIG. 29, with continuing reference to FIGS. 2 and 27-28, a scapula axis SA may be established. The scapula axis SA may extend through a reference point along an articular surface of the scapula model 330S. The articular surface may be associated with a glenoid of the scapula. The scapula axis SA may extend between a first point P1 (e.g., center of the glenoid fossa) and a second point P2 (e.g., trigonum scapulae) of the scapula model 330S.

Figure 31:
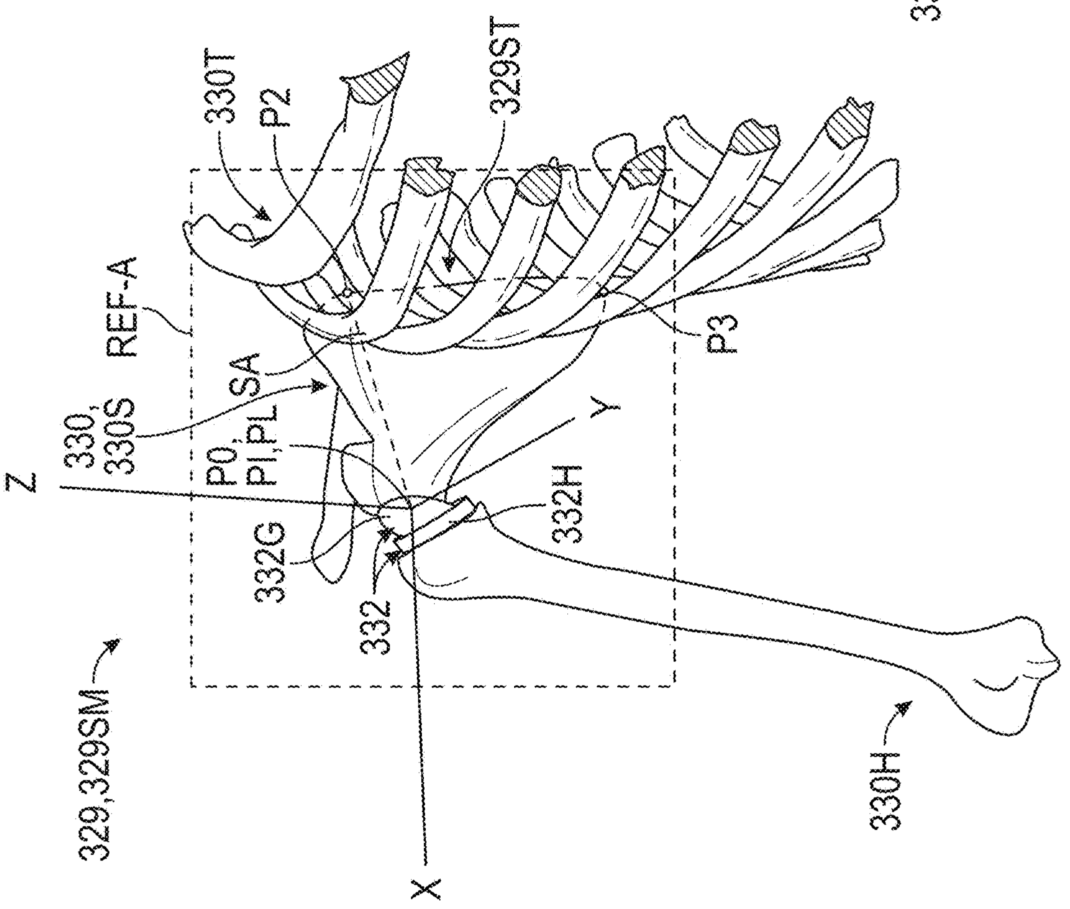

Referring to FIG. 31, with continuing reference to FIGS. 2 and 27-28, an anatomical (e.g., scapular) plane REF-A may be established. The scapular plane REF-A may be fit through the scapula model 330S. The scapular plane REF-A may be determined by landmarks or may be a best fit scapular plane. The scapular plane REF-A may be established along the scapula axis SA and may extend between the first point P1 at the center of the glenoid fossa and the second point P2 at the trigonum scapulae. The scapular plane REF-A may extend through a third point P3. The third point P3 may be established at an inferior angle of the scapula. The spatial module 50 may be configured to determine the scapula axis SA and/or one or more anatomical landmarks along the scapula model 330S, including the first, second and/or third points P1, P2, P3. The spatial module 50 may be configured to determine the scapular plane REF-A such that the scapular plane REF-A may extend along the scapula axis SA.

Referring to FIG. 30, with continuing reference to FIGS. 2 and 27-29, the scapula model 330S may be associated with a first (e.g., local, scapula or acquisition) reference system. The scapula reference system may have an origin PL. The spatial module 50 may be configured to apply a predefined transformation to the scapula model 330S to re-orient the scapula model 330S from the first reference system to a second, different reference system. The first reference system may be the local reference system. The second reference system may be the global reference system established at step 382D-1. The system 10 may establish a surgical plan 36 associated with the bone model(s) 330 with respect to the global reference system. The surgical plan 36 may include an implant plan associated with an implant. The implant plan may include an implant type, an implant dimension, and/or an implant position and/or orientation associated with an implant model 32.

Referring again to FIG. 31, with continuing reference to FIGS. 2 and 27-30, registering the scapula bone model 330S at step 382D may include adjusting an orientation of the scapula bone model 330S. In implementations, the spatial module 50 may be configured to apply the predefined transformation such that the scapula model 330S may be translated and/or rotated, which may cause the scapula reference system of the scapula model 330S to be aligned (e.g., registered) with the global reference system. The origin PL of the scapula reference system may be established at the first point P1 at the center of the glenoid fossa of the scapula model 330S. The alignment may occur such that the first point P1 at the center of the glenoid fossa may be positioned at an origin P0 of the global reference system. The system 10 may be configured to execute a predefined transformation of the humeral bone model 330H from a local (e.g., humeral) reference system to the global reference system utilizing any of the techniques disclosed herein regarding the scapula model 330S. The system 10 may be configured to execute a predefined transformation of the thorax bone model 330T from a local (e.g., thoracic) reference system to the global reference system utilizing any of the techniques disclosed herein regarding the scapula model 330S and/or humerus model 330H. In implementations, the spatial module 50 may be configured to apply the same predefined transformation associated with the glenoid bone model 330G to the humeral bone model 330H such that a relative position between the glenoid bone model 330G and humeral bone model 330H may remain the same between the reference systems. The spatial module 50 may be configured to apply the same predefined transformation associated with the scapula model 330S to the thorax bone model 330T such that a relative position between the scapula model 330S and thorax bone model 330T may remain the same between the reference systems. An orientation of the scapula model 330S, humeral model 330H and/or thorax model 330T relative to the global reference system may be representative of a posture of the patient in the anatomical position.

The system 10 may be configured to register one or more implant models 32 in the global reference system according to any of the techniques disclosed herein. In the implementation of FIG. 30, the system 10 may be configured to register the position of one or more implant models 332 in the global reference system. The implant models 332 may be arranged along the glenoid and/or humeral head of the associated bone models 330S, 330H. The implant models 332 may be registered concurrently with the registration of the scapula model 330S and/or humeral model 330H. In other implementations, the implant models 332 may be positioned relative to the scapula and humeral models 330S, 330H subsequent to registration of the scapula and/or humeral bone models 330S, 330H in the global reference system.

Still other techniques may be utilized to re-orient the anatomical and/or bone model(s) from one reference system to another reference system. The planning system 10 may configured to determine the position of the bone associated with a respective bone model based on a geometry of one or more other bones and associated bone model(s) and/or anatomical model(s), including adjoining bone(s) and/or non-adjoining bones of the patient. In implementations, the planning system 10 may configured to determine the position, alignment and/or angle of the bone associated with a respective bone model based on a geometry of one or more other bones and associated bone model(s) and/or anatomical model(s), including adjoining bone(s) and/or non-adjoining bones of the patient. In implementations, the planning system 10 may configured to determine the position, alignment and/or angle of the bone associated with the respective bone model based on a relationship of the bone to a (e.g., global) reference system and/or one or more kinematic planes and/or axes of the patient.

At step 382D-2, the anatomical and/or bone model(s) may be re-oriented from a first reference system to a second reference system based on one or more predetermined correlations with anatomical landmarks and/or the anatomy of one or more other patients (e.g., of a representative patient population). The planning system 10 may be configured to establish the surgical plan 36 in response to comparing the anatomical and/or bone model(s) 29, 30 of the patient and the anatomical and/or bone model(s) 29, 30 of one or more other patient(s) and/or patient population(s). The patient population may exclude the patient.

The system 10 may be configured to re-orient the bone model(s) 330 and/or anatomical model(s) 329, such as the scapula model 330S and/or thorax model 330T, based on a relationship between two or more adjoining and/or non-adjoining bones of the anatomy. The spatial module 50 may be configured to determine the position of the bone associated with the bone model 330 based on a geometry of another bone relative to the scapula, including adjoining bone(s) such as the humerus and/or non-adjoining bones such as the clavicle. In implementations, the system 10 may be configured to determine the position of the scapula associated with the scapula model 330S based on a geometry of adjoining and/or non-adjoining bone(s) of the thorax, including one or more ribs associated with the scapulothoracic joint and/or one or more non-adjoining bones such as the sternum, one or more thoracic vertebrae, and/or one or more (e.g., small) ribs of the patient.

Step 382D-2 may include re-orienting (X, Y, Z) the scapular plane REF-A (e.g., FIG. 31) of the scapula model 330S based on one or more pre-determined correlations. The predetermined correlations may be established with respect to anatomical landmarks and/or SSM/numerical makeup classification. The SSM/numerical makeup classifications may be established utilizing any of the techniques disclosed herein, such as with the statistical shape modeler 72. The planning system 10 may be configured to establish a transformation and associated parameters of the transformation for each AMC 80 based on the predetermined correlations, which may be utilized to register the associated bone model(s) and/or anatomical models(s) from one reference system to another reference system, including the scapula model 330S, humerus model 330H and/or thorax model 330T.

The scapula model 330S may be registered to the global reference system utilizing one or more defined landmarks, including any of the anatomical landmarks disclosed herein. The system 10 may be configured to determine a position of one or more landmarks along the scapula and/or other portions of the anatomy. The landmarks may be utilized to define a transformation from the scapula reference system to the global coordinate system (e.g., FIG. 30). An orientation of the scapula model 330S, humeral model 330H and/or thorax model 330T relative to the global reference system may be representative of an anatomical position of the patient. Landmarks along the scapula may include the center of the glenoid fossa (e.g., point P1 of FIG. 29), the inferior angle of the scapula (e.g., point P3 of FIGS. 29 and 31), and/or the trigonum scapulae (e.g., point P2 of FIG. 29).

Various techniques may be utilized to determine the landmarks, including any of the techniques disclosed herein. The surgeon or clinical user may interact with the display window 360 and/or another portion of the user interface 356 (e.g., FIGS. 21-23) to specify the landmarks relative to the respective bone model 330, including the scapula model 330S and/or thorax model 330T. In implementations, the spatial module 50 may be configured to determine the landmarks along the scapula model 330S and/or other bone models 330 of the anatomical model 329, such as the thorax model 330T.

Referring to FIGS. 2, 4 and 28, with continuing reference to FIGS. 27, the scapula model 330S, humerus model 330H and/or thorax model 330T may be registered in the global reference system based on a statistical shape model (SSM) 75 and assigned anatomical (e.g., numerical) makeup classification (AMC) 80. One or more respective SSMs 75 may be established for the scapula, humerus, thorax and/or other bones of the anatomy. The statistical shape modeler 72 may be configured to utilize the SSM 75 to assign an AMC 80 to the anatomical and/or bone model(s) based on one or more bones of the anatomy, such as the scapula, humerus and/or thorax. In implementations, each AMC 80 may be established for a single bone of the anatomy, such as the scapula or humerus. AMCs 80 may be established for one or more respective bones of the thorax, including the sternum, vertebrae and/or ribs of the patient. In implementations, an anatomical (e.g., multi-bone) SSM 75 may be established for two or more bones of the anatomy, including non-adjoining and/or adjoining bones such as the scapula, humerus and/or thorax. The SSM 75 may include one or more bones of the thorax, including any of the bones disclosed herein. Anatomical (e.g., multi-bone) AMCs 80 may be established for two or more bones of the anatomy based on the anatomical SSM 75, including adjoining bones of a joint such as the scapula and humerus, the scapula and thorax, and/or non-adjoining bones. AMCs 80 may be established for adjoining bones associated with the scapulothoracic joint, including the scapula and one or more ribs of the thorax, and/or non-adjoining bones such as the scapula and various bones of the thorax, including the sternum, one or more (e.g., small) rib(s) and/or one or more thoracic vertebrae. The statistical shape modeler 72 may be configured to analyze sets of image data 74 for constructing the respective SSM 75. The statistical shape modeler 72 may be configured to determine the position of each landmark within the SSM 75 that may be utilized to transform the bone model(s) 30 from a local reference system to the global reference system. In implementations, the statistical shape modeler 72 may assign an AMC 80 to one or more of the bone models 330, including the scapula model 330S, humerus model 330H and/or thorax model 330T (e.g., FIG. 28).

The statistical shape modeler 72 may query the AMC database 70 to locate bone models 30 stored therein that have similar AMCs 80. The coordinate information of bone models 30 associated with the AMC database 70 may be normalized to the global reference system. In implementations, normalizing the coordinate information may include applying a transformation to the associated bone model(s) 30 from the acquisition reference system to the global reference system utilizing any of the techniques disclosed herein.

The comparison module 52 and/or statistical shape modeler 72 may be configured to select a representative bone model 30 from a set of representative bone models 30 associated with the SSM 75. The SSM 75 and bone model 330 of the patient may be associated with common bone(s) of an anatomy, such as the scapula, humerus and/or thorax. The comparison module 52 and/or statistical shape modeler 72 may be configured to assign the AMC 80 of the selected representative bone model 30 to the bone model 330 of the patient. Each representative bone model 30 within a set of representative bone models 30 may be assigned a respective AMC 80 based on the SSM 75. The comparison module 52 and/or statistical shape modeler 72 may be configured to assign the AMC 80 of the selected representative bone model 30 to the bone model 330. The AMC 80 may be associated with any of the parameters and/or respective values disclosed herein, such as a posture of the patient and/or humeroscapular and/or scapulothoracic contributions to a range of motion.

The statistical shape modeler 72 may be configured to assign to the bone model 330 an AMC 80 associated with another patient that is closest to the anatomy encompassed by the bone model 330. The AMC database 70 may include stored information specifying one or more landmarks of the bone model 30 associated with the assigned AMC 80. The bone model(s) 30 associated with the assigned AMC 80 may be registered in the global reference system.

In implementations, establishing a surgical plan 36 for the patient may include selecting a representative bone model 30 from the set of representative bone models 30 associated with the respective SSM 75. The SSM 75 and the representative bone models 30 may be associated with common bone(s) of an anatomy. Establishing the surgical plan 36 may include comparing the bone model 330 of the patient and the selected representative bone model 30 associated with the SSM 75. The surgical plan 36 may be established based on the bone model 330 in the global reference system.

The landmarks of the bone model 330 may be paired with associated landmarks of the bone model 30 of the assigned AMC 80. The bone model 330 of the patient may be re-oriented such that the pairs of landmarks of the representative and patient bone models 30, 330 may be substantially aligned in the global reference system. Various characteristics of the patient anatomy may be determined based on the landmark positions of the representative bone model 30, such as posture and/or humeroscapular and/or scapulothoracic contributions to a range of motion.

In implementations, an instance of the bone model(s) 30 of the assigned AMC 80 in the global reference system may be substantially aligned with the bone model(s) 330 of the patient in the local reference system to determine values for one or more correction angles. The correction angles may include three angles of rotation relative to the axes of the reference system. A transformation may be established based on determined values of the correction angles. The spatial module 50 may be configured to apply the transformation to the respective bone model(s) 330 of the patient to register the bone model(s) 330 in the global reference system. In other implementations, the patient bone model(s) 330 may be registered in the global reference system by substantially aligning the patient bone model(s) 330 with the selected bone model(s) 30 of another patient in the global reference system.

In implementations, the statistical shape modeler 72 may be configured to determine the position of the bone (e.g., scapula) associated with bone model 30 based on a geometry of another (e.g., adjoining) bone relative to the scapula, including adjacent bone(s) such as the humerus and/or ribs(s) of the thorax and/or non-adjoining bones such as the clavicle, sternum, one or more thoracic vertebrae and/or (e.g., small) rib(s) of the patient. In implementations, the system 10 may be configured to determine an angle of the respective rib(s) relative to a reference, such as the Z axis of the reference system. The angles associated with the respective ribs may be same or may differ from each other. The system 10 may be configured to determine the posture based on the determined rib angle(s), including one or more ribs associated with the scapulothoracic joint. The statistical shape modeler 72 may be configured to determine a position of the bone relative to the skeletal anatomy based on one or more characteristics of the bone and associated landmarks.

A posture of the patient may be utilized to establish the plurality of AMCs 80$_N$. A posture of the patient may be defined with respect to one or more parameters, including any of the parameters disclosed herein such as the scapular angle (e.g., angle of FIGS. 17A-17C). The relative position and/or orientation of one or more bone models 330 of the thorax model 330T relative to each other and/or the scapula model 330S may be utilized to determine a posture of the patient, including any of the bones disclosed herein. The statistical shape modeler 72 may be configured to establish the AMCs 80 based on one or more predefined modes (e.g., modes of variation) 76. The parameter(s) associated with posture may establish one or more of the predefined modes 76, including any of the posture parameters disclosed herein such as scapular angle. Predefined modes 76 associated with posture may include a relationship between two or more adjoining and/or non-adjoining bones. The statistical shape modeler 72 may be configured to receive the predefined mode(s) 76 associated with posture as an input. The statistical shape modeler 72 may be configured to assign an AMC 80 to the respective anatomy and associated bone models 30 based on the predefined mode(s) 76 associated with posture. In other implementations, the predefined modes 76 may omit a posture of the patient.

An AMC 80 may be selected based on a (e.g., best) fit between the bone model(s) 30 associated with the AMC 80 and the bone model(s) 330 of the patient. The landmarks of the bone model(s) 30 associated with the selected AMC 80 may be utilized to determine a posture of the patient. In implementations, the landmarks associated with the selected AMC 80 may be utilized to determine various posture characteristics, such as a scapula angle relative to the global reference system. The bone model(s) 330 of the patient may be reoriented from the acquisition orientation to the global reference system by applying a transformation based on the determined posture.

The disclosed systems and methods may be utilized to position and/or orient a model of the scapula and/or thorax to substantially match the preoperative posture of the patient, which may be utilized to determine and/or validate range of motion of an associated bone such as the humerus. The disclosed techniques may be utilized to position and/or orient models of respective bones of the thorax relative to each other based on the posture of the patient, include the sternum, thoracic vertebrae and/or ribs of the patient. Various implementations may be utilized in accordance with the teachings disclosed herein, including determining range of motion based on posture information and/or scapulothoracic and/or humeroscapular contributions.

Figure 33:
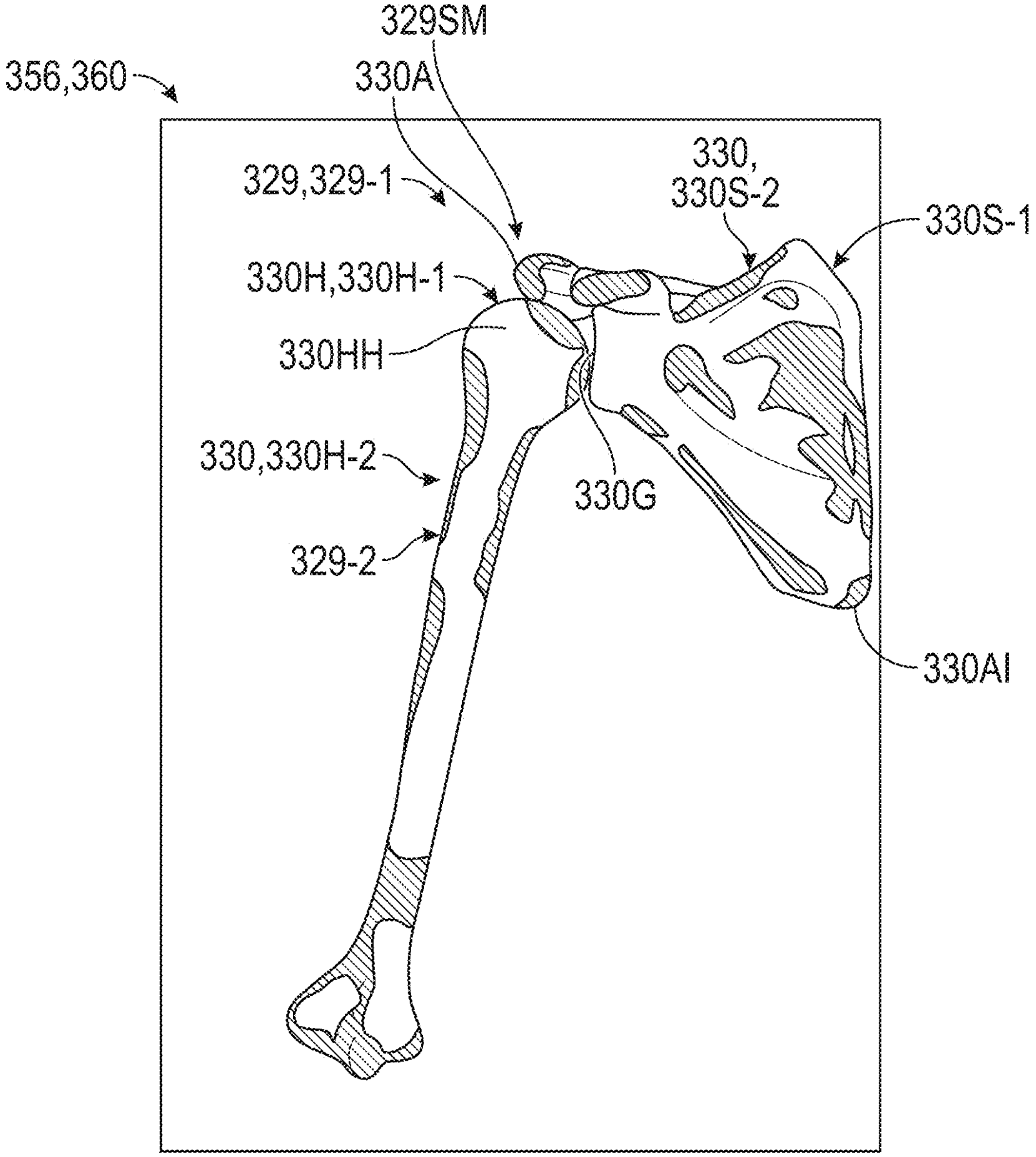
FIG. 33 disclose a shoulder model of a patient.
Figure 35:
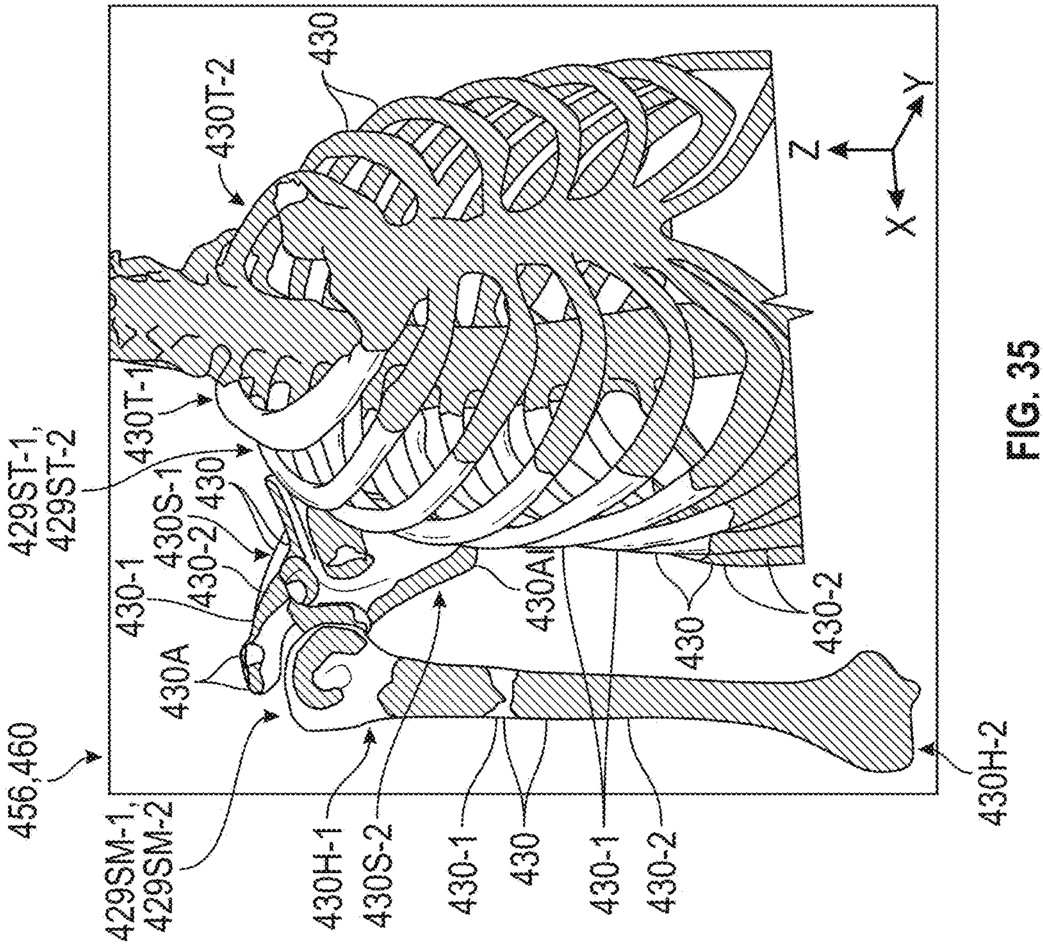
FIGS. 34-35 disclose a scapulothoracic model of a patient.
Figure 34:
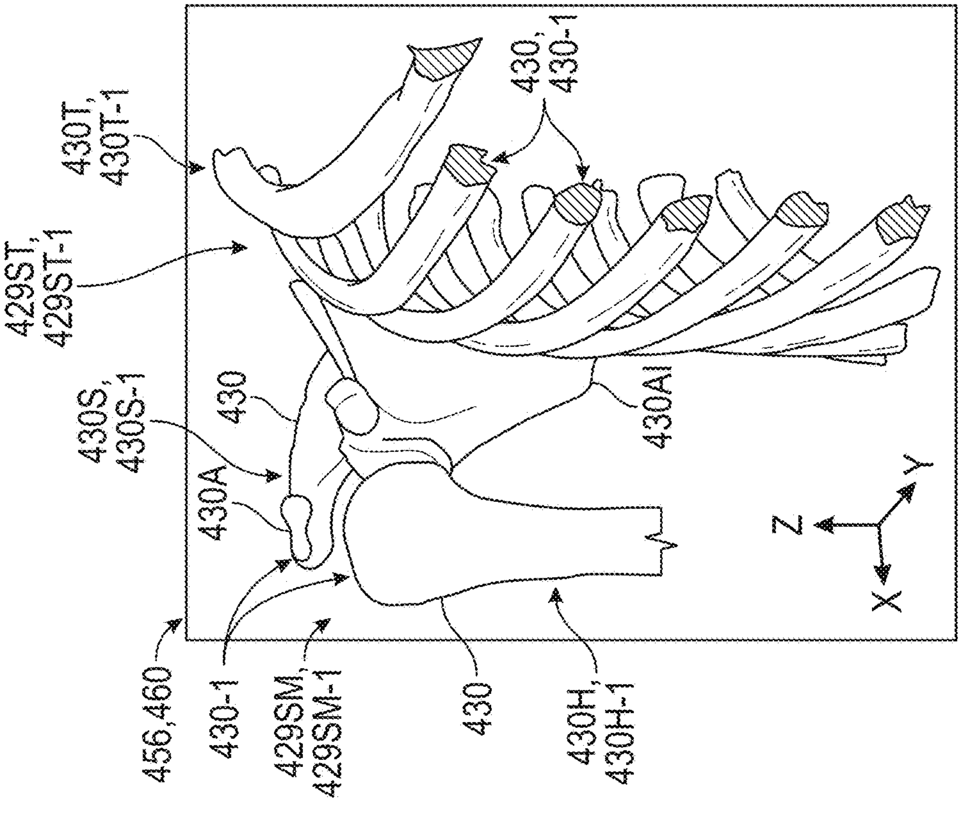

Referring to FIG. 33, with continuing reference to FIGS. 2, 4 and 27, the statistical shape modeler 72 and/or another portion of the planning environment 28 may be configured to overlay representative bone model(s) 30 corresponding to the assigned AMC 80 onto the respective bone model(s) 330 of the patient, which may be associated with the humerus, scapula and/or thorax (e.g., bone models 330S-1/330S-2 and 330H-1/330H-2 of FIG. 33, and bone models 430H-1/430H-2, 430S-1/430S-2 and 430T-1/430T-2 of FIG. 35). The surgeon or clinical user may interact with the user interface 356 to toggle (e.g., on and off) visibility of the overlaid bone model(s) 30 associated with the SSM 75. The overlaid bone model(s) 30 associated with the SSM 75 may provide a pre-morbid representation of the patient anatomy, which the surgeon may evaluate to establish, edit and/or approve a surgical plan 36.

Step 382D may include substituting the bone model 330 of the patient with another bone model 30 corresponding to the AMC 80 assigned to the bone model 330 of the patient. The AMC database 70 may include coordinate information associated with a position and/or orientation of the substitute bone model 30 in the global reference system. The substitute bone model 30 may serve as a pre-morbid representation of the patient anatomy. The pre-morbid representation may omit osteophytes and/or other surface irregularities which may otherwise impede a range of motion of the associated bone. The surgeon may remove the osteophyte and/or otherwise treat the surface irregularities during the surgical procedure. Analyzing range of motion utilizing the substitute bone model 30, including in the global reference system, may provide a relatively more accurate predication of the post-operative range of motion with the surface irregularities removed or otherwise treated.

At step 382E, an initial anatomical position of one or more bones associated with the anatomical model 329 may be determined. Step 382E may include setting an initial anatomical position of the humerus bone model 330H in the global coordinate system based on the posture of the patient. Step 382E may include determining (e.g., setting) the initial anatomical position of the humerus model 330H subsequent to registering the anatomical model 329 in the global reference system.

The method 382 may include predicting or otherwise determining the position, alignment and/or angle of a bone (e.g., humerus) associated with a respective bone model based on a geometry of one or more other bones (e.g., scapula and/or thorax) and associated bone model(s) and/or anatomical model(s), including adjoining bone(s) and/or non-adjoining bones of the patient. Step 382E may include determining an initial anatomical position of another (e.g., second) bone of the anatomy associated with the anatomical model 329, such as a humerus associated with the humerus bone model 330H. Various techniques may be utilized for determining the anatomical initial humerus position, including any of the techniques disclosed herein such as the techniques associated with step 382D. The initial anatomical position of the other bone (e.g., humerus) may be determined based on the determined posture at step 382D. In implementations, the anatomical initial humerus position may be based on a relationship of the bone to a (e.g., global) reference system and/or one or more kinematic planes and/or axes of the patient, and determining a posture of the patient may be omitted. Although the techniques of step 382E primarily refer to the humerus relative to the scapula, it should be understood that the techniques may be utilized for any two adjoining and/or non-adjoining bones of the anatomy. In implementations, step 382D may be utilized to determine an orientation of the humerus, and step 382E may be utilized to determine an orientation of the scapula. The planning environment 28 may be configured to determine the humeroscapular contribution to a range of motion based on the starting position of the patient humerus model. The planning environment 28 may be configured to determine the scapulothoracic contribution to the range of motion based on the starting position of the patient scapula model.

Referring to FIGS. 2 and 4, the storage system 18 may be configured to store two-dimensional and/or three-dimensional bone models 30 associated with one or more bones and/or one or more joints of the representative patient population. The bone models 30 may include a first set of bone models 30 and a second set of bone models 30. The first set of bone models 30 may be associated with a first bone of the anatomy. The second set of bone models 30 may be associated with a second bone of the anatomy. Bone models 30 within the first and second sets may be associated with a common anatomical model 29 of a respective patient.

The bone models 30 and associated bones of the representative patient population may be associated with one or more SSMs 75. In implementations, two or more adjoining and/or non-adjoining bones associated with the bone models 30 may be associated with the same SSM 75. The planning environment 28 may configured to determine the position, alignment and/or angle of the bone associated with a respective bone model 30 based on a geometry of one or more other bones and associated bone model(s) 30 and/or anatomical model(s) 29, including adjoining bone(s) and/or non-adjoining bones of the patient. Step 382E may include analyzing the representative patient population within the SSM 75. The statistical shape modeler 72 may be configured to analyze the representative patient population within the associated SSM 75. The SSM 75 may be established based on a statistically significant number of prior cases to characterize variation of the associated bone(s) of the anatomy. In implementations, the SSM 75 may be established based on at least 100 to 1,000 prior cases, or more narrowly at least 10,000 to 20,000 prior cases. The statistical shape modeler 72 may be configured to create a plurality of AMCs 80 based on a plurality of predefined modes (e.g., modes of variation) 76 within the SSM 75. The statistical shape modeler 72 may be configured to receive as an input one or more predefined modes 76. The predefined modes 76 may characterize anatomical differences within the representative patient population and standard deviations 78 of anatomical variances contained within each of the predefined modes 76. The statistical shape modeler 72 may be configured to assign the AMCs 80 to the bone models 30. The storage system 18 may be configured to store the AMCs 80. Step 382E may include identifying the predefined modes 76 within the SSM 75 of the representative patient population.

Predefined modes 76 that may be provided to the statistical shape modeler 72 may include, but are not limited to, any of the predefined modes, factors and other patient characteristics disclosed herein, including size of the bone(s) and/or portion of the bone(s) (e.g., scapula, glenoid, humerus, humeral head, diaphysis, thorax, etc.), amount of inclination, amount of version, amount of retrotorsion (e.g., of humerus), projected amount of glenoid and sagittal neck length, angle of glenoid relative to scapular neck, critical shoulder angle, projection of acromion and/or coracoid, and varus/valgus of humeral head, relative position and/or orientation between the scapula and thorax, relative position and/or orientation of various bones of the thorax, anatomical landmarks, joint space, soft tissue attachment points and/or other characteristics, pre-operative range of motion, any combinations of the foregoing, etc. In implementations, the predefined modes 76 associated with the scapula, humerus and thorax may be the same or may differ. The number of predefined modes 76 may be selected based on an amount of variation associated with individual modes and/or a combination of the modes. An amount of variation of the mode(s) may differ based on the selected anatomy. The predefined modes 76 may include a posture mode associated with a posture of a patient. The posture mode may be established based on two or more adjoining and/or non-adjoining bones of the anatomy. In implementations, the predefined modes 76 may omit a posture of the patient.

Referring to FIG. 35, with continuing reference to FIGS. 2, 4, 27 and 34, the anatomical model 429 may be a first anatomical model 429-1 associated with the patient. Step 382E may include determining the anatomical initial position of other bone model(s) 430, such as the humerus bone model 430H-1, based on an anatomical SSM 75 associated with two or more bones of the anatomical (e.g., scapula, humerus and/or thorax). Step 382E may include determining the anatomical initial position of the humerus bone model 430H-1 relative to a selected bone model 30 associated with an AMC 80 assigned to the scapula bone model 430S-1 and/or thorax bone model 430T-1. The selected bone model 30 may be associated with a second (e.g., representative) anatomical model 429-2. The bone model 430H-2 assigned to the humerus bone model 430H-1 may be associated with the same patient as the bone model(s) 430S-2, 430T-2 assigned to the bone model(s) 430S-1, 430T-1. The initial anatomical position may be determined based on a relative position between the respective bone models 430. An AMC 80 associated with the anatomical model 429-2 may be assigned to the patient anatomical model 429-1.

The humerus model 430H-1 may be associated with the same patient as the scapula model 430S-1 and/or thorax bone model 430T-1. The representative humerus model 430H-2 may be associated with a different patient, including a real patient associated with a prior case or a hypothetical patient. The statistical shape modeler 72 may be configured to assign the AMC 80 associated with the representative bone model 430-1 to the respective patient bone model 430-2. The humerus bone model 430H-2 may be assigned based on the SSM 75 utilizing any of the techniques disclosed herein. The planning environment 28 may be configured to determine one or more landmarks associated with the bone based on the assigned bone model 430H-2 associated with the SSM 75.

One or more portions of a bone may be omitted from image data associated with the image(s) 26. The image(s) 26 may omit portions of the anatomy to reduce radiation exposure to the patient. The image data 26 may omit portions of the humerus and/or thorax, which may be depicted by the respective humerus model 430H-1 and/or thorax bone model 430T-1 associated with the patient (e.g., FIG. 34). The omitted portions may include a distal (or proximal) portion of the humerus model 430H-1. Portion(s) of the thorax may be omitted from the image data 26 and/or the thorax bone model 430T-1, such as medial portions of the ribs, the sternum, vertebrae and/or ribs on an opposite side of the thorax. The image data 26 may be insufficient to determine a position of the scapula relative to the thorax of the patient.

The planning environment 28 may be configured to determine an initial anatomical position of another adjoining and/or non-adjoining bone (e.g., humerus, scapula and/or thorax) in the anatomical model 429 based on a completeness of the acquisition information. Determining an initial anatomical position of other bone(s) such as the humerus at step 382E may include determining a geometry and/or orientation of the omitted portion(s) of the bone. A geometry and/or orientation of the omitted portion(s) may be determined based on a SSM 75 associated with the respective bone(s). The planning environment 28 may be configured to predict or compute the omitted portion(s) of the bone model(s) 430 based on the SSM 75. The SSM 75 may be associated with two or more adjoining and/or non-adjoining bones of the anatomy, such as the scapula, humerus and/or thorax. A scapula bone model 430S-2, humerus model 430H-2 and/or thorax bone model 430T-2 may be associated with the anatomy of another patient (FIG. 35). The bone model(s) 430-2 of another patient may be used to represent the omitted portion(s) and/or an entirety of the bone model(s) 430-1 of the patient. The other patient may be a patient of a representative patient population.

A representation of the omitted portion(s) of the bone(s) may be established by selected bone model(s) 30 associated with the SSM 75, such as the humerus bone model 430H-2 and/or thorax bone model 430T-2. The SSM 75 may be utilized to select a representative bone model 430-2 associated with the AMC database 70 that may be closest to the anatomy associated with the (e.g., partial) bone model 430-1 of the patient. The planning environment 28 may be configured to substitute the (e.g., partial) bone model 430-1 of the patient with the bone model 430-2 corresponding to the assigned AMC 80.

The planning environment 28 may be configured to associate the anatomical model 429-1 of the patient with two or more instances of a bone model 430 associated with the same bone of the anatomy to establish the representation of the omitted portion(s) of the bone, such as the patient and representative bone model(s) 430-1, 430-2 (e.g., 430H-1/430S-1/430T-1, 430H-2/430S-2/430T-2). The planning environment 28 may be configured to determine the geometry of the omitted portions and/or an orientation of the bone utilizing any of the techniques disclosed herein. The geometry and/or orientation of the omitted (e.g., distal) portion of the humerus may be determined based on the representative humerus bone model 430H-2. The geometry and/or orientation of the omitted (e.g., medial, anterior and/or posterior) portion(s) of the thorax may be determined based on the representative thorax bone model 430T-2.

The spatial module 50 may be configured to orient (e.g., align) the bone models 430-1, 430-2 relative to each other utilizing any of the techniques disclosed herein. The spatial module 50 may be configured to re-orient or otherwise move the bone models 430-1, 430-2 together relative to other bone model(s) 430-1, 430-2 and/or a reference point (e.g., origin) of the reference system to determine the initial anatomical position of the associated bone. The spatial module 50 may be configured to apply a predetermined transformation to re-orient or otherwise move the bone models 430-1 and/or 430-2. In implementations, the spatial module 50 may be configured to re-orient or otherwise move the representative bone model 430-2, but not the patient bone model 430-1, or vice versa, to determine the initial anatomical position of the associated bone(s), such as the scapula, humerus and/or thorax. In implementations, the spatial module 50 may be configured to determine one or more landmarks associated with the bone(s) of the patient, including any omitted portion(s), based on the assigned representative bone model 430-2 associated with the SSM 75.

Multi-bone prediction techniques may be utilized to determine a spatial relationship between the bone models 30 associated with an anatomical model 29 of the patient and/or omitted portion(s) of the bone model(s) 30 based on the spatial relationship. The planning system 10 may be configured to determine a geometry and/or orientation of the bone associated with omitted or incomplete bone information based on a relationship to another adjoining and/or non-adjoining bone. The predicted geometry and/or orientation of the omitted portion(s) of the bone may be utilized to determine a pre-morbid anatomy of the patient. The predicted geometry and/or orientation information may be utilized to establish an implant plan associated with the patient bone, including adjusting a default starting position and/or orientation of an implant.

Multi-bone prediction techniques may be utilized to determine a relative position between the scapula, humerus and/or thorax. The memory 44 may be operable to store three-dimensional bone models 30 associated with respective bones of a representative patient population. The bone models 30 may include a first set associated with a scapula, a second set associated with a thorax, and a third set associated with a humerus. A SSM 75 may be established for one or more bones of the anatomy, including adjoining and/or non-adjoining bones such as the humerus, scapula, thorax, etc.

The planning environment 28 may be configured to select a representative scapula model from the first set of the bone models in response to comparing the representative scapula model to a patient scapula model associated with the scapula of a patient. The representative scapula model may be associated with a representative thorax model of the second set of the bone models. The patient scapula model and a patient thorax model may establish a first spatial relationship. The representative scapula and thorax models may establish a second spatial relationship. The planning environment 28 may be configured to determine a range of motion of a patient humerus model associated with a humerus of the patient model relative to one or more kinematic planes in response to comparing the first and second spatial relationships. The range of motion may be an overall range of motion of the patient humerus model relative to the more kinematic plane(s).

The planning environment 28 may be configured to predict or otherwise determine scapulothoracic and/or humeroscapular movement of the patient anatomy based on a relationship between two or more bones of the patient anatomy and those of another patient (e.g., size, orientation, geometry, etc.). The planning environment 28 may be operable to determine the amount of expected scapulothoracic movement (e.g., contribution) for the overall range of motion and/or in one or more kinematic planes based on the determined relationship between the scapula and thorax. The bone model(s) 430-1 associated with the patient anatomy may be assigned an AMC 80 associated with the anatomy of another patient that may be the closest to the patient anatomy. The planning environment 28 may be operable to assign scapulothoracic movement value(s) and/or numerical relationship(s) (e.g., ratios, percentages, etc.) to the bone model(s) 430 associated with the patient anatomy based on the assigned AMC 80, which may be utilized to determine (e.g., estimate) the range of motion for the bone model(s) 430-1, such as the humerus model 430H-1 of the patient.

The statistical shape modeler 72 may be configured to select a first representative (e.g., scapula) three-dimensional bone model 430S-2 and/or a second representative (e.g., humerus or thorax) three-dimensional bone model 430H-2/430T-2 associated with a representative anatomical model 429-2/529-2 in response to varying one or more of the predefined modes 76 within the SSM 75. Selecting the anatomical model 429-2 may occur in response to varying one or more of the predefined modes 76 within the SSM 75.

The statistical shape modeler 72 may be configured to select a first representative model 430S-2 from a first set of the bone models 30 in response to comparing the first representative bone model 430S-2 to the first patient bone model 430S-1 associated with a first bone of the patient, such as the scapula. The first representative model 430S-2 may be associated with a second representative model 430H-2/430T-2 of the second set of the bone models 30. The first patient model 430S-1 and second patient model 430H-1/430T-1 may establish a first spatial relationship relative to each other. The second patient model 430H-1/430T-1 may be associated with a second bone of the patient, such as the humerus or thorax. The first and second representative bone models 430S-2, 430H-2/430T-2 may establish a second spatial relationship. The first bone and the second bone may be adjoining or non-adjoining bones, including any of the bones disclosed herein such as the scapula, humerus and/or one or more bones of the thorax. The first and second spatial relationships may be based on one or more landmarks associated with the first bone and/or the second bone, including any of the landmarks disclosed herein.

The comparison module 52 may be configured to determine at least one or more patient characteristics associated with the first bone and/or the second bone of the patient in response to comparing the first and second spatial relationships. The patient characteristics may be associated with a posture of the patient and/or humeroscapular and/or scapulothoracic contributions to the range of motion. The bone models 30 may include one or more 3D bone models 30 associated with one or more bones of a representative patient population. The planning environment 28 may be operable to determine the scapulothoracic movement in response to comparing the scapula model 430S-1 and the thorax model 430H-1 of the patient to a representative scapula model 430S-2 and a representative thorax model 430T-2 of another patient of the representative patient population. The planning environment 28 may be operable to select the representative scapula model 430S-2 in response to analyzing the representative patient population within a SSM 75. The statistical shape modeler 72 may be configured to select the representative bone model(s) 430H-2, 430S-2 and/or 430T-2 in response to varying one or more predefined modes 76 of the SSM 75. The comparison module 52 may be configured to establish an implant plan based on the patient characteristic(s). The spatial module 50 and/or statistical shape modeler 72 may be configured to determine a (e.g., spatial) deviation between the first spatial relationship established by the bone models 430S-1, 430H-1/430T-1 of the patient and the second spatial relationship established by the representative bone models 430S-2, 430H-2/430T-2 associated with another patient of the representative patient population. The comparison module 52 may be configured to determine the patient characteristic(s) based on the spatial deviation.

The comparison module 52 may be configured to compare the first representative bone model 430S-2 to the patient bone model 430S-1 in response to causing the spatial module 50 to at least partially or substantially fit a volume of the first representative bone model 430S-2 and a volume of the patient bone model 430S-1 to each other. The comparison module 52 may be configured to compare the second representative bone model 430H-2/430T-2 to the patient bone model 430H-1/430T-1 in response to causing the spatial module 50 to at least partially or substantially fit a volume of the representative bone model 430H-2/430T-2 and a volume of the patient bone model 430H-1/430T-1 to each other.

A transformation may be applied to the selected bone model 30. The spatial module 50 may be configured to apply the transformation. The transformation may be established by re-orienting (e.g., adjusting) the selected bone model 430S-2 to substantially align with the scapula bone model 430S-1 of the patient. Once completed, the orientation of patient scapula of the associated scapula bone model 430S-1 may be computed based on the applied transformation to the assigned bone model 30. In implementations, the spatial module 50 may be configured to adjust a position of the patient bone model 430S-1 and/or a position of the patient bone model 430H-1/430T-1 based on the determined patient characteristic(s).

The spatial module 50 may be configured to register the first patient bone model 430S-1 and/or the second patient bone model 430H-1/430T-1 from a local reference system to a global reference system based on the determined patient characteristic(s). The planning environment 28 may be configured to establish a surgical plan associated with the patient scapula bone model 430S-1, humerus bone model 430H-1 and/or thorax bone model 430T-1 in the global reference system.

Selecting the anatomical model 429-2 may occur in response to at least partially fitting the bone models 430S-2, 430H-2, and/or 430T-2 of the anatomical model 429-2 to the respective patient bone models 430S-1, 430H-1 and/or 430T-1 of the anatomical model 429-1 in the same reference system. The scapulothoracic and/or humeroscapular movements and/or contributions associated with the anatomical model 429-1 of the patient may be determined based on the anatomical model 429-2 and/or the associated AMC 80.

The planning environment 28 may be operable to determine the overall range of motion based on a humeroscapular contribution of humeroscapular movement between the patient humerus model 430H-1 and the patient scapula model 430S-1 and a scapulothoracic contribution of scapulothoracic movement between the patient scapula model 430S-1 and the patient thorax model 430T-1. The planning environment 28 may be operable to determine a numerical relationship between the humeroscapular contribution and the scapulothoracic contribution for at least one position, a set of positions, and/or all positions relative to the overall range of motion. The display module 48 may be configured to display one or more values and/or graphical indicators associated with the numerical relationship(s) in the user interface 456.

The display module 48 may be configured to display a representation of the omitted portion(s) in the display windows 460 of the user interface 456. The display module 48 may be configured to display the bone models 430-1, 430-2 overlaid with each other in the display window 460. In implementations, the surgeon or clinical user may interact with the user interface 456 to selectively view the first and/or second bone models 430-1, 430-2 in the display window 460.

The planning environment 28 may be configured to automatically generate a preoperative surgical plan 36 (FIG. 2) based on the anatomical scapula pose and/or anatomical humerus position. The preoperative plan 36 may specify various parameters (e.g., implant type, size and orientation). The surgical plan 36 may include an implant plan associated with one or more implants to treat a patient.

Figure 32:
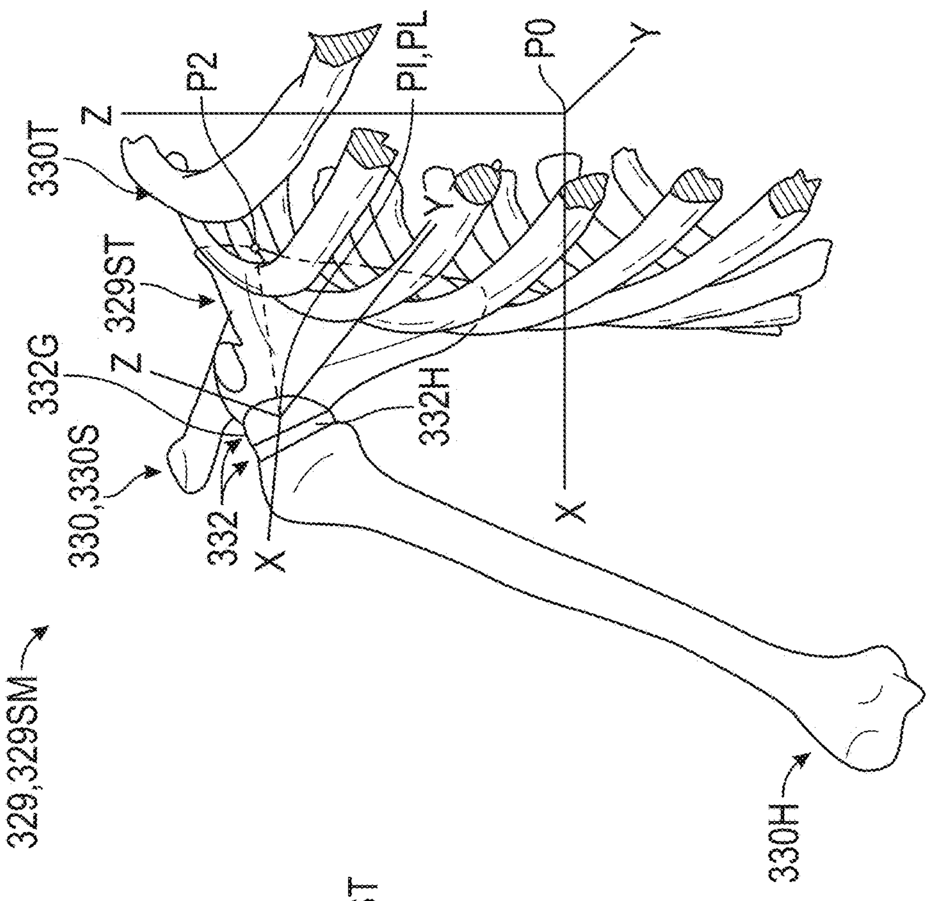

Referring back to FIG. 32, with continuing reference to FIGS. 2, 4, 8 and 27, at step 382F a position and/or orientation of one or more implant models 332 may be determined based on an orientation of the associated bone model(s) 330, such as the scapula model 330S and/or humerus model 330H. The planning environment 28 may be operable to position at least one implant model 332 relative to the scapula model 330S and/or humerus model 330H of the patient. The planning environment 28 may be configured to determine a position of one or more implants and associated implant models 332 based on an orientation of the anatomical model 329 and/or bone models 330, including the scapula model 330S, humerus model 330H and/or thorax model 330T, in the respective reference system including any of the reference systems disclosed herein. The implant models 332 may include a first (e.g., glenoid) implant model 332G and/or a second (e.g., humerus) implant model 332H. The implant models 332G, 332H may be configured to articulate or otherwise mate with each other.

The planning environment 28 may be configured to determine an optimal implant position based on a determined (e.g., predicted) posture characteristic(s) of the patient and/or scapulothoracic and/or humeroscapular contributions to the range of motion. Determining the implant position may be based on a relationship between the scapula and humerus associated with a shoulder joint and/or a relationship between the scapula and the thorax associated with a scapulothoracic joint, which may be utilized to determine the contribution(s) to the range of motion. The planning environment 28 may be configured to establish an implant plan based on one or more posture parameters, which may be determined utilizing any of the techniques disclosed herein. The planning environment 28 may be configured to apply a correction factor to a default implant position and/or orientation based on the determined posture characteristic(s) and/or contribution(s) to the range of motion. The correction factor may be established based on a specific posture value (e.g., scapula angle). Determining the implant position may be based on a relationship between two or more adjoining and/or non-adjoining bones that may be determined utilizing any of the techniques disclosed herein, which may occur additionally or alternatively to determining a posture of the patient. The adjoining bones may be associated with a scapulothoracic joint. The correction factor may be established based on the determined scapulothoracic and/or humeroscapular contribution(s) to the range of motion, any of the factors, and/or other patient characteristics disclosed herein, alone and/or in combination.

The spatial module 50 may be configured to position the implant model(s) 332 and bone model(s) 330 relative to each other in the global reference system based on the implant position specified in the surgical plan 36. The planning environment 28 may be configured to determine an optimal implant position based on a predicted posture of the patient and/or determined scapulothoracic and/or humeroscapular contribution(s) to the range of motion. In implementations, a retrotorsion of the humeral implant model 332H may be adjusted to improve clinical range of motion. The position and orientation of each implant model 332 relative to the respective bone model 330 may be established in the global reference system according to the assigned AMC 80. The AMC database 70 may include coordinate information associated with a position of each bone model 30 in the global reference system and/or respective acquisition reference system. The surgeon or clinical user may adjust the assigned position and/or orientation of the implant model(s) 332 prior to approving the surgical plan 36. The spatial module 50 and/or another portion of the planning environment 28 may be operable to adjust a position of the implant model(s) 332 relative to the shoulder joint model 329SM based on a previously determined iteration of the overall range of motion.

At step 382G, a range of motion associated with one or more bone models 330 and/or respective implant model(s) 332 of the anatomy may be determined. The planning environment 28 may be operable to determine a range of motion of the humerus model 330H based on the position of the implant model(s) 332. The range of motion modeler 101 and/or another portion of the planning environment 28 may be configured to performing a range of motion simulation based on one or more landmark characteristics and/or other patient characteristics that may be determined utilizing any of the techniques disclosed herein. Based on various patient characteristics, such as posture, anatomical initial humerus position, selected implant(s) (e.g., type, size and orientation), and/or scapulothoracic and/or humeroscapular contribution(s) to the range of motion, the planning environment 28 may be configured to predict or compute range of motion outcomes for the current patient associated with the anatomical model 329 of the patient. The range of motion may be based on the position and/or orientation of the implant model(s) 332 determined at step 382F. The bone model(s) 330 may be associated with a scapula, humerus and/or thorax of the patient. The ROM modeler 101 may be configured determine the range of motion in response to performing a range of motion simulation for the assigned AMC(s) 80 assigned to the bone model(s) 330 and/or associated anatomical model 329. The ROM modeler 101 may be configured to determine range of motion based on the AMC 80 assigned to the bone model(s) 330, including scapula, humeral and/or thorax models 330S, 330H, 330T associated with the scapula, humerus and/or thorax, utilizing any of techniques disclosed herein. The range of motion modeler 101 may be configured to perform a range of motion simulation of the bone model 330 in the global reference system based on the determined patient characteristic(s) and/or the assigned AMC 80 of the respective bone(s). Step 382G may include storing range of motion data derived from the range of motion simulation within a storage system 18 of the system 10. The data module 46 may be configured to store the range of motion data within the storage system 18.

At step 382H, a preoperative surgical plan 36 may be established for the patient. The planning environment 28 may be configured to automatically generate the surgical plan 36 based on the determined patient characteristic(s). The surgical plan 36 may specify various parameters (e.g., implant type, size and orientation). The surgical plan 36 may include an implant plan associated with one or more implants to treat a patient. The surgical plan 36 may be established based on the implant position(s) determined at step 382F.

Referring to FIGS. 36A-36E, with continuing reference to FIGS. 2 and 4, the surgeon or clinical user may evaluate humeroscapular (e.g., glenohumeral) motion to evaluate a range of motion for the arm of a patient, in which the humerus may move relative to a (e.g., fixed or static) scapula. The humerus may be moved in one or more kinematic planes to determine the range of motion. However, scapulothoracic movement may contribute to the range of motion of the humerus. The scapulothoracic joint may be associated with an articulation between the thorax (e.g., rib cage) and the scapula relative to one or more kinematic planes. Scapulothoracic rotation may include internal/external rotation (e.g., about the Z axis of FIG. 36A), upward/downward rotation (e.g., about the Y axis of FIG. 36A) and/or posterior/anterior tilting (e.g., about the X axis of FIG. 36A). Scapulothoracic motion may begin to occur when, or prior to, the humeroscapular motion reaching a limit. An amount of the scapulothoracic motion relative to the overall (e.g., humerothoracic) range of motion may increase as abduction of the arm increases.

FIGS. 36A-36E disclose an anatomical model 529 including bone models 530 at various positions. FIGS. 36A-36E may be associated with abduction of the arm. The anatomical model 529 may include a shoulder model 529SM and associated scapulothoracic model 529ST. Movement of the shoulder model 529SM and/or scapulothoracic model 529ST may be established relative to one or more kinematic planes REF-K. The planning environment 28 may be operable to determine movement of the scapula model 530S, humerus model 530H and/or thorax model 530T in the kinematic plane(s) REF-K. In the implementation of FIGS. 36A-36E, the kinematic plane REF-K may be associated with abduction of the humerus model 530H.

The comparison module 52 and/or another portion of the planning environment 28 may be configured to determine the position and/or orientation of the implant model(s) 532 that may achieve a desired (e.g., maximum) range of motion of the humerus model 530H relative to one or more, or each, of the kinematic planes REF-K of the patient. The comparison module 52 may be configured to set the position and/or orientation of the implant model(s) 532 based on the posture of the patient. The comparison module 52 may be configured to adjust or otherwise set the position and/or orientation of the implant model(s) 532 based on a determined range of motion of the associated bone model 532, such as the humerus model 530H, in one or more of the kinematic planes REF-K. The comparison module 52 may be configured to set the position and/or orientation of the implant model(s) 532 based on the determined (e.g., assigned or predicted) scapulothoracic movement of the scapula model 530S associated with the range of motion.

The desired range of motion in the kinematic plane(s) REF-K may be associated with one or more acts of daily living and/or lifestyle goals. Utilizing the techniques disclosed herein, range of motion and mobility of the patient based on determined posture and/or scapulothoracic contribution may be improved relative to the kinematic plane(s) REF-K of the patient.

The planning environment 28 may be operable to determine (e.g., assign or predict) a humeroscapular contribution and/or scapulothoracic contribution to the range of motion of the humerus model 530H. Utilizing the techniques disclosed herein, acts of daily living and/or lifestyle goals may be established and/or evaluated based the determined humeroscapular and/or scapulothoracic contributions. The humeroscapular contribution may be associated with an angle between an axis HA of the humerus model 530H and an axis SA of the scapula model 530S. The axis SA may follow a spine of the scapula model 530S adjacent to the scapulothoracic joint. The axis SA may be associated with the reference plane REF1 of FIGS. 17A-17C. The axis HA of the humerus model 530H may be associated with a diaphysis axis of the humerus. The scapulothoracic contribution may be associated with an angle between the axis SA of the scapula model 530S and an axis PA of the patient. The axis PA may be associated with the vertebrae of the patient. The axis PA may be collinear with or may otherwise be substantially parallel to the Z axis. In other implementations, the scapulothoracic contribution may be associated with an angle between a first (e.g., initial or starting) position and a second (e.g., final or stopping) position of the axis SA associated with the range of motion in the respective kinematic plane REF-K.

Figure 36A:
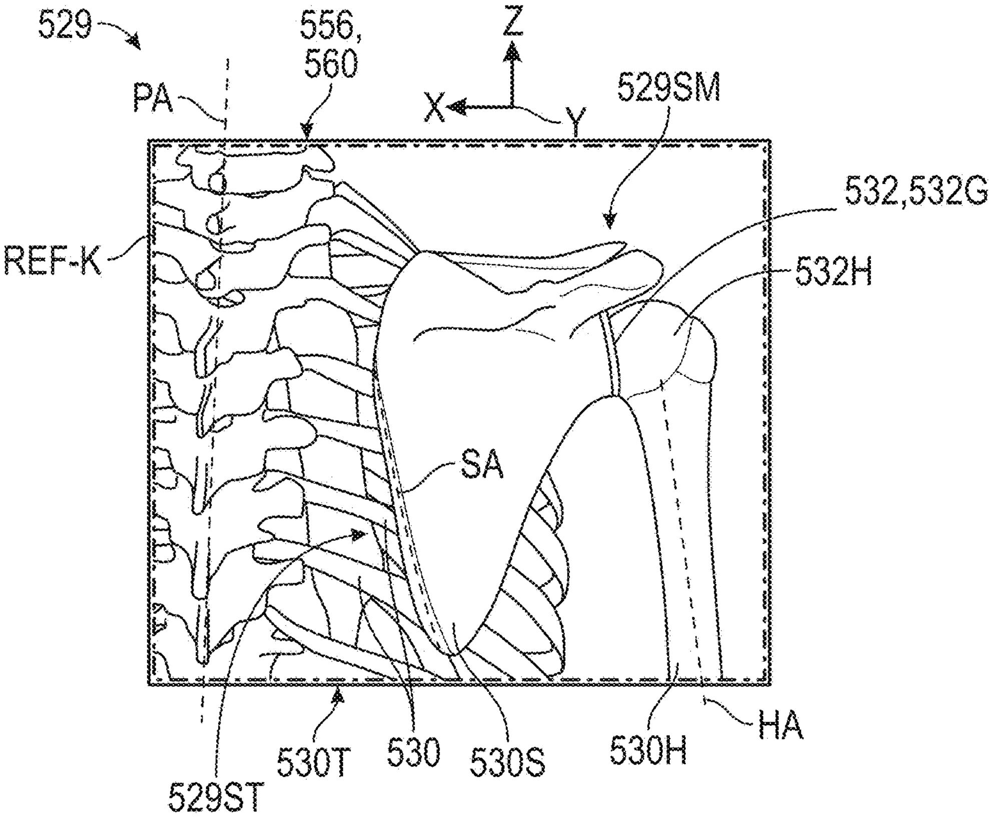
FIGS. 36A-36E disclose an anatomical model.
Figure 36B:
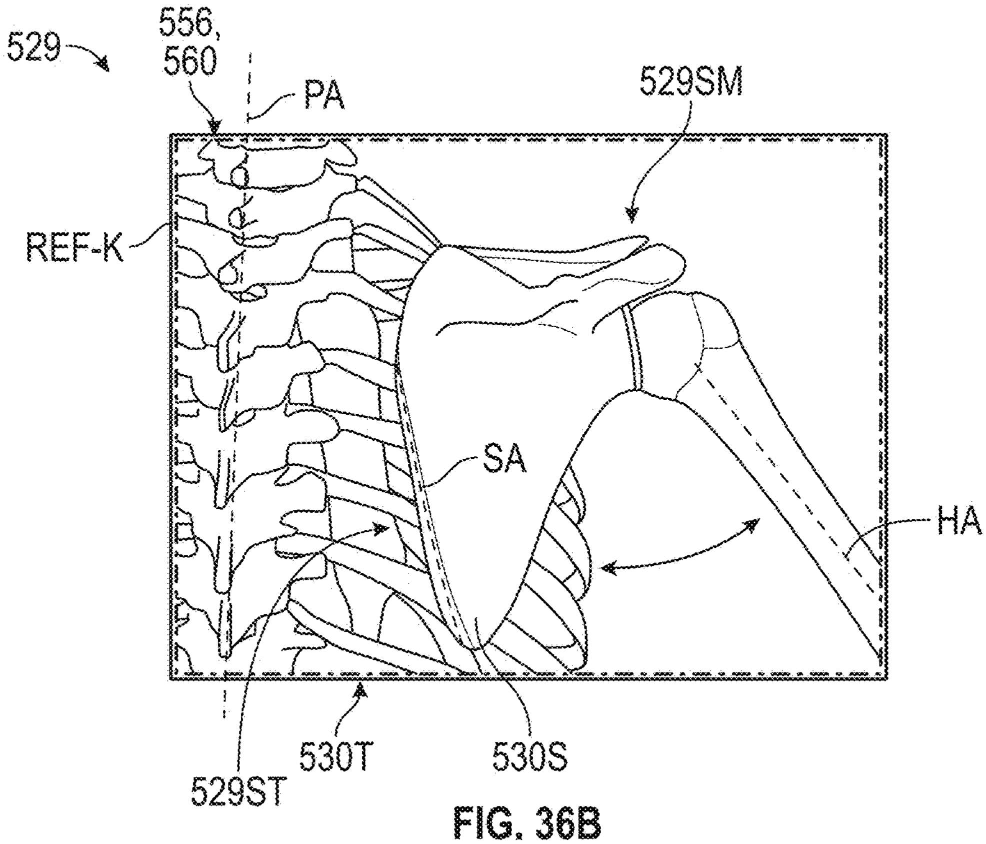
Figure 36C:
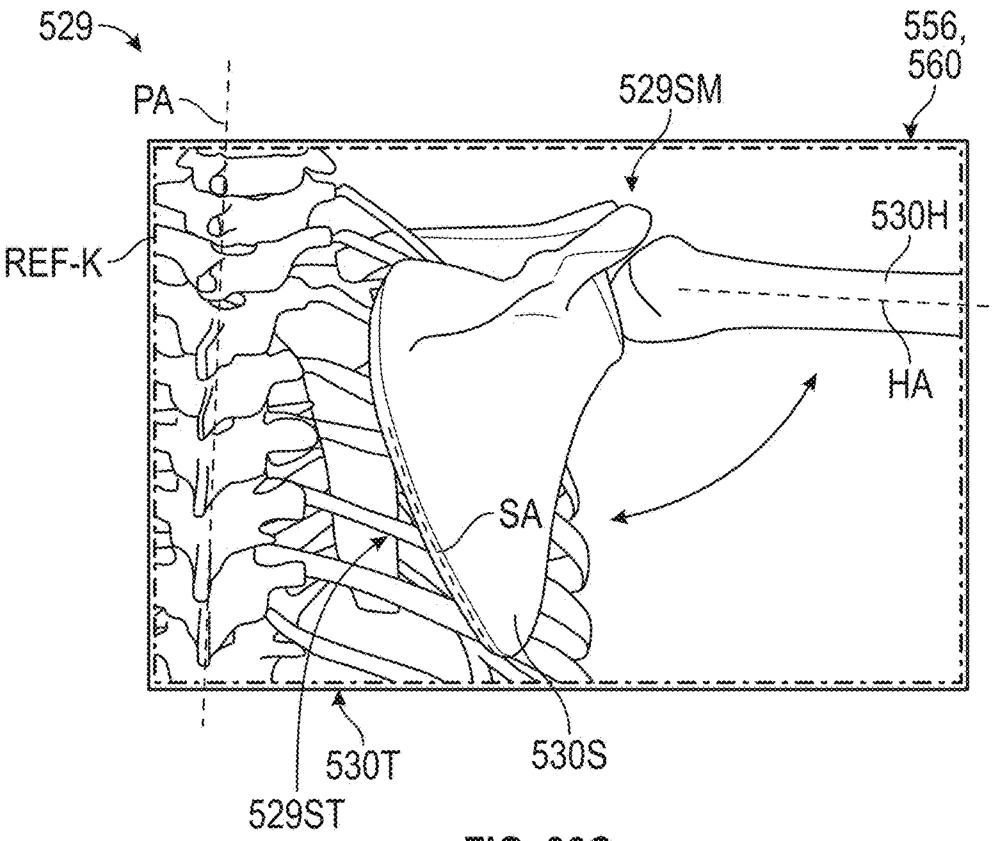
Figure 36D:
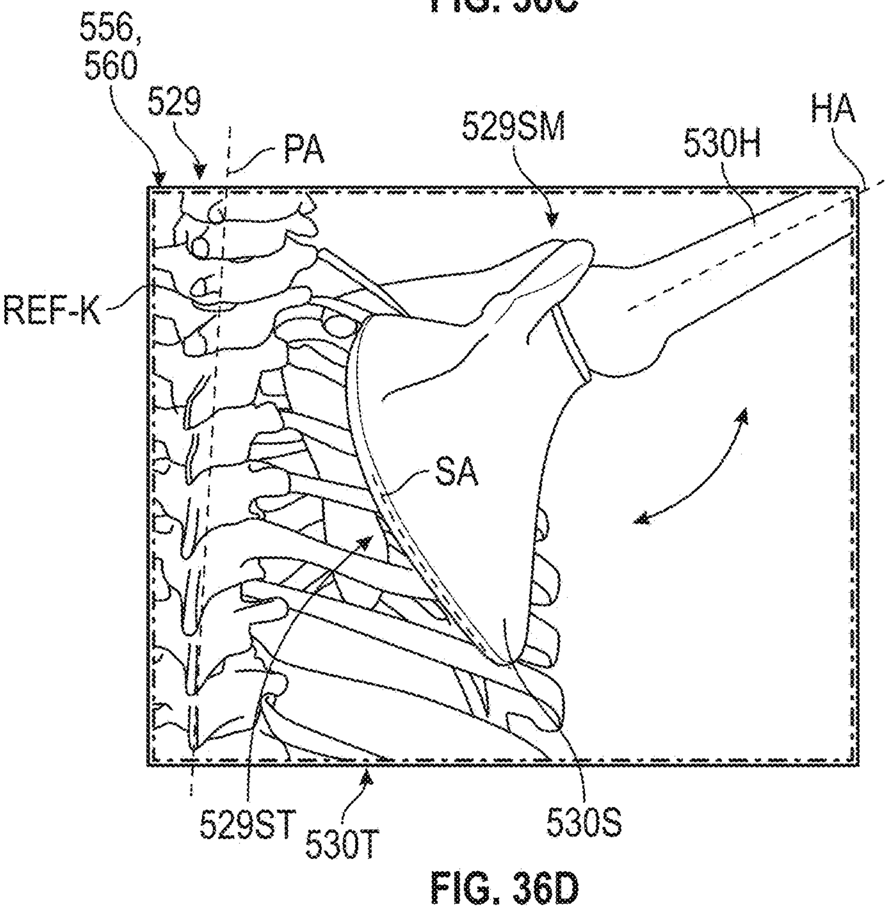
Figure 36E:
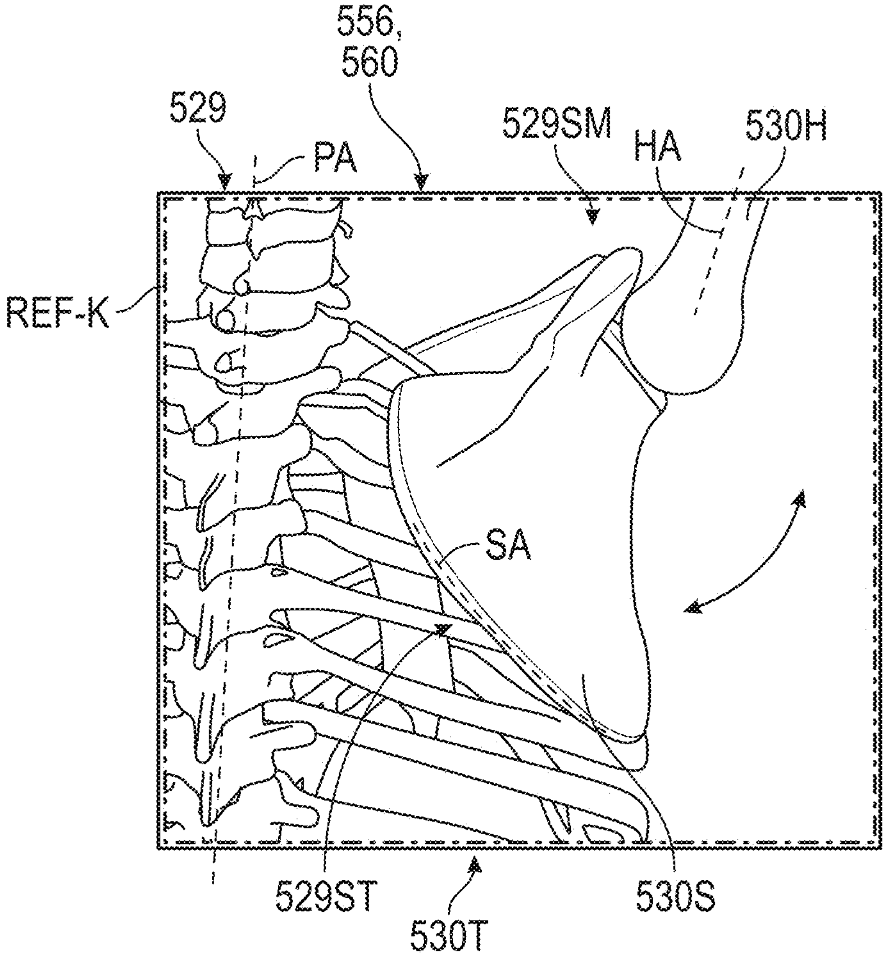

The planning environment 28 may be operable to display (e.g., depict) movement of the humerus model 530H, scapula model 530S and/or thorax model 530T in one or more display windows 560 of a user interface 556, including incrementally and/or continuously across the range of motion associated with one or more kinematic planes REF-K. FIG. 36A may be associated with a starting (e.g., minimum) position of the humerus model 530H. FIG. 36E may be associated with a stopping (e.g., maximum) position of the humerus model 530H. One or more impingement points may limit the starting and/or stopping positions. Impingement may occur between the scapula and thorax models 530S, 530T. Impingement may occur between the humerus implant model 532H and the scapula model 532S and/or glenoid implant model 532G. FIGS. 36B-36D may be associated with intermediate positions of the humerus model 530H. FIG. 36B may be associated with only, or a majority of, humeroscapular movement. FIGS. 36C-36E may be associated with a combination of humeroscapular and scapulothoracic movement. FIG. 36E may be associated with only, or a majority of, scapulothoracic movement.

In the implementation of FIGS. 36A-36E, an overall range of motion of the humerus model 530H may include approximately 150 degrees of abduction. All, or at least a majority of, movement between the starting position of FIG. 36A and the intermediate position of FIG. 36B may be associated with humeroscapular movement. The scapulothoracic contribution may vary (e.g., increase) as the humerus model 530H approaches an impingement point. All, or at least a majority of, movement between the intermediate (e.g., impingement) position of FIG. 36D and stopping position of FIG. 36E may be associated with scapulothoracic movement. The contributions of humeroscapular and scapulothoracic movement across the range of motion may vary for different patients based on the bony anatomy, posture, implant position and/or soft tissue associated with the shoulder joint.

The planning environment 28 may be operable to determine (e.g., assign, compute and/or predict) one or more numerical relationships associated with the humeroscapular and/or scapulothoracic contributions to the range of motion. The numerical relationships may include ratios, percentages or single and/or multivariate functions (e.g., linear and/or non-linear curves) relative to the humeroscapular and scapulothoracic contributions and/or the overall range of motion. One or more ratios may be established for discrete increments of the range of motion of the arm associated with humeroscapular and scapulothoracic movement. The numerical relationship(s) may be established based on any of the factors and/or other patient characteristics disclosed herein, either alone and/or in combination.

The numerical relationship may include a contribution ratio (HS:ST) between the humeroscapular contribution (HS) and the scapulothoracic contribution (ST) to the range of motion. Contribution ratios may be established for respective increments of the range of motion and/or the overall range of motion (e.g., between minimum and maximum positions). The contribution ratio(s) may be cumulative and/or non-cumulative.

The planning environment 28 may be operable to determine the contribution ratio for a set of positions relative to the overall range of motion. The set of positions may include a first position associated with commencement of the scapulothoracic contribution and may include a second position associated with a maximum limit relative to the overall range of motion. The contribution ratio associated with the first position may differ from the contribution ratio associated with the second position. The planning environment 28 may be operable to display the contribution ratio for the set of positions relative to the overall range of motion.

For abduction of the arm, in implementations a range between 0 degrees and 60 degrees may be associated with only humeroscapular movement (e.g., a contribution ratio of 1:0). A range above 60 degrees to 70 degrees may be associated with a contribution ratio of approximately 3:1. A range above 70 degrees to 80 degrees may be associated with a contribution ratio of approximately 2:1. A range above 80 degrees may be associated with only scapulothoracic movement (e.g., a contribution ratio of 0:1).

The anatomical model 529 and/or bone model(s) 530 associated with the patient may be assigned an AMC 80 associated with another patient. The scapulothoracic and/or humeroscapular contributions associated with the respective AMC 80 may be assigned to the anatomical model 529 associated with the patient. The ROM modeler 101 (FIG. 8) may be operable to perform a range of motion simulation in one or more kinematic planes for one or more bone models 530 based on the scapulothoracic and/or humeroscapular contributions associated with the assigned AMC 80. The assigned scapulothoracic contribution may be linear or non-linear (e.g., progressively increase) between a starting position of the contribution and a position associated with impingement.

Figure 37:
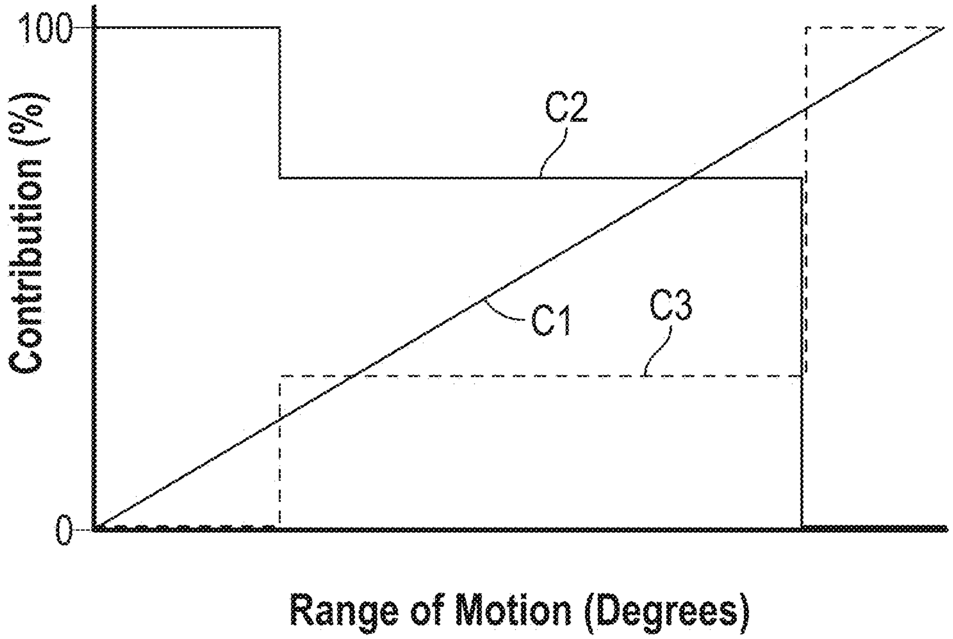
FIGS. 37-38 disclose plots associated with scapulothoracic and humeroscapular movements.
Figure 38:
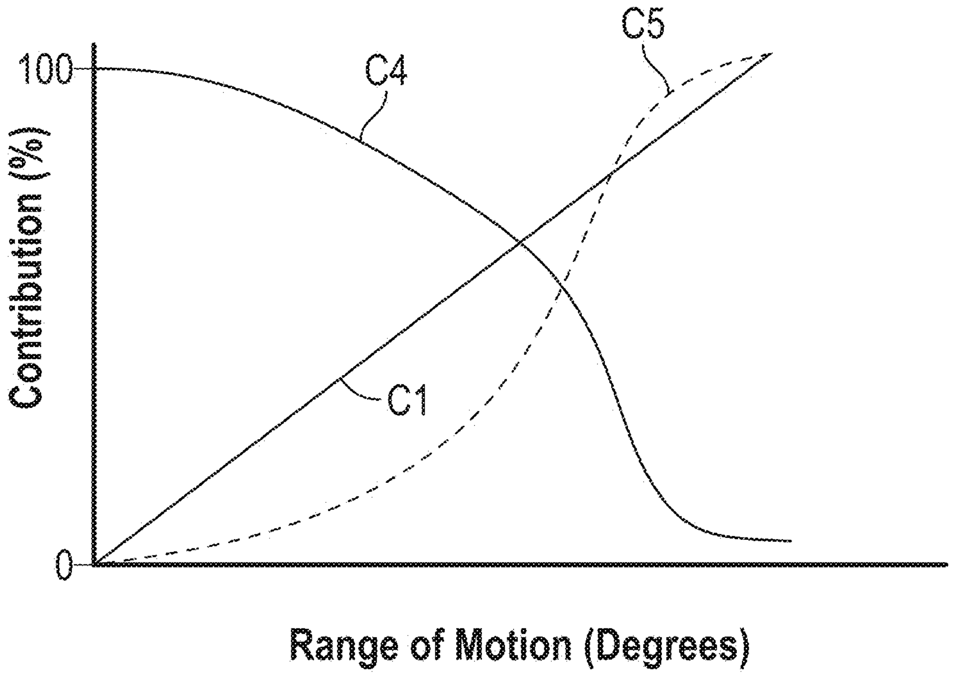

The planning environment 28 may be operable to determine the scapulothoracic contribution based on a parametric relationship with respect to the humeroscapular contribution. The parametric relationship may include a step function and/or a curve progression. The scapulothoracic and/or humeroscapular contributions may be established as a step function (e.g., FIG. 37), curve progression (e.g., FIG. 38) or other relationship with respect to the range of motion. In the implementation of FIG. 37, a curve C1 may be associated with the (e.g., overall) range of motion with respect to a kinematic plane. Curve C2 may be associated with a humeroscapular contribution to the range of motion. Curve C3 may be associated with a scapulothoracic contribution to the range of motion. Curves C2, C3 may be defined as respective step functions. In the implementation of FIG. 38, curve C4 may be associated with a humeroscapular contribution to the range of motion. Curve C5 may be associated with a scapulothoracic contribution to the range of motion. Curves C4, C5 may be defined as multivariate curves. The curves C1, C2 and/or C4, C5 may be inversely proportional to each other. Numerical relationships may be established for respective anatomical models 29 and/or bone models 30. The numerical relationships may be stored and/or accessed in the database 38.

The planning environment 28 may be operable to assign one or more numerical relationships (e.g., ratios) to the anatomical model 529. The ROM modeler 101 may be operable to perform a range of motion simulation based on the assigned numerical relationships(s). The display module 48 may be operable to display one or more indicators (e.g., values) of the humeroscapular and/or scapulothoracic contributions relative to each other and/or the overall range of motion. The display module 48 may be operable to display the numerical relationships(s) in one or more display windows 60 of the user interface 56 (e.g., FIGS. 47-50).

Various techniques may be utilized to determine scapulothoracic and other movements for a patient. In implementations, movement may be determined with an ultrasound device, including for a portion or entirety of the range of motion. The arm may be positioned. The device may record the position of one or more landmarks to determine how much the scapula and/or humerus may move for any particular full-arm movement. The data module 46 may be operable to store the measured values in the database 38. The data module 46 may be operable to associate the measured values with the respective anatomical model 29 and/or bone model(s) 30. The comparison module 52 may be operable to determine numerical relationship(s) between the humeroscapular and scapulothoracic contributions and/or overall range of motion based on the measurements.

Various factors (e.g., indicators or parameters) associated with the anatomy of a patient may be utilized to predict or otherwise determine an amount of scapulothoracic and/or humeroscapular motion in any given arm movement relative to the respective kinematic plane(s), including any of the factors disclosed herein. The factors may include a profile of the patient, such as age, activity, size, etc. The factors may include various landmark characteristics, including the size and/or orientation (e.g., angle) of the bone(s), scapula characteristics (e.g., curvature) and/or humerus characteristics. The factors may include a starting position of the scapula and/or humerus relative to the kinematic plane(s). The comparison module 52 may be operable to determine the starting position of the scapula and/or humerus based on a posture of the patient. The factors may include one or more soft tissue characteristics (e.g., tension, attachment points, etc.). The factors may include implant geometry, position and/or orientation. The factors may include one or more impingement (e.g., collision) points between the anatomy and/or implant(s), which may be determined based on a range of motion simulation. Any of the factors and/or other patient characteristics disclosed herein may be incorporated into the planning environment 28 to determine (e.g., predict) post-operative range of motion based on scapulothoracic and/or humeroscapular contributions in one or more kinematic planes.

Characteristics associated with the patient profile may include patient age and activity. Older patients may be relatively more stiff and/or less mobile. A shape and curvature of the anatomy may be (e.g., highly) correlated to patient size, including the scapula, thorax and/or humerus.

One or more anatomical landmark characteristics (e.g., classifications) associated with the anatomy may influence scapulothoracic motion, including landmarks associated with the scapula, humerus and/or thorax. The surgeon or clinician may obtain one or more objective measurements of the anatomy, which may be accessed by the planning environment 28. Various techniques may be utilized to measure or otherwise determine the landmarks, including directly with a surgical (e.g., ultrasound) device and/or by evaluating images of the anatomy. The planning environment 28 may be operable to determine an amount of the scapulothoracic movement based on one or more landmark characteristics associated with the humerus bone model, the scapula bone model, and/or the thorax bone model. The planning environment 28 may be operable to assign the scapulothoracic contribution based on the determined amount of the scapulothoracic movement for a range of motion.

Figure 39A:
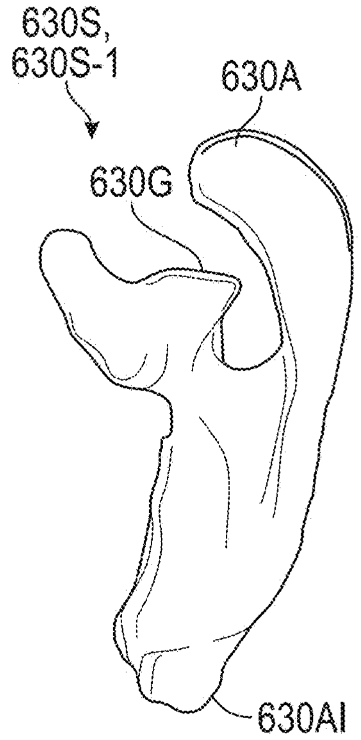
FIGS. 39A-39C and 40A-40C disclose a set of scapula models.
Figure 39B:
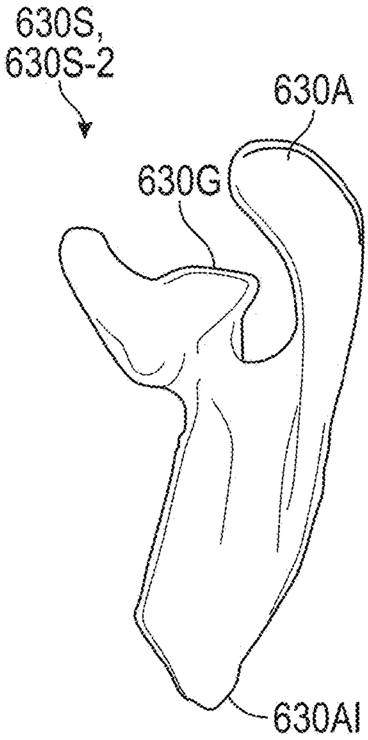
Figure 39C:
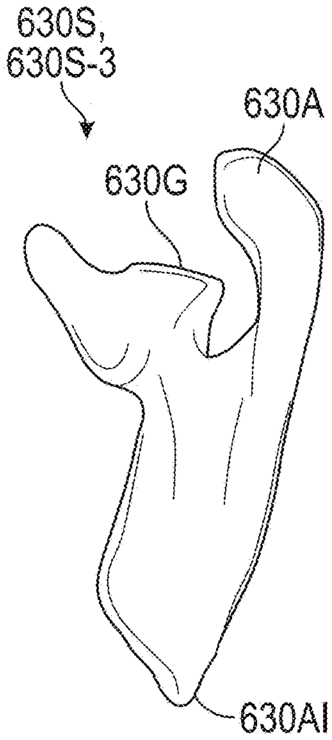
Figure 40A:
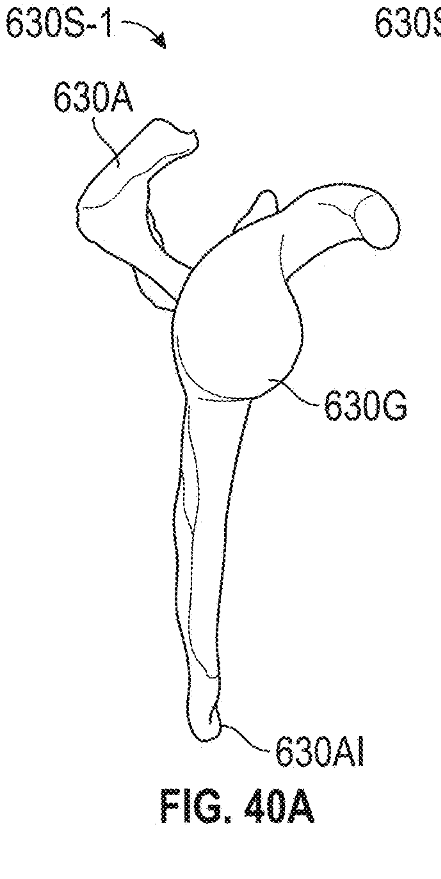
Figure 40B:
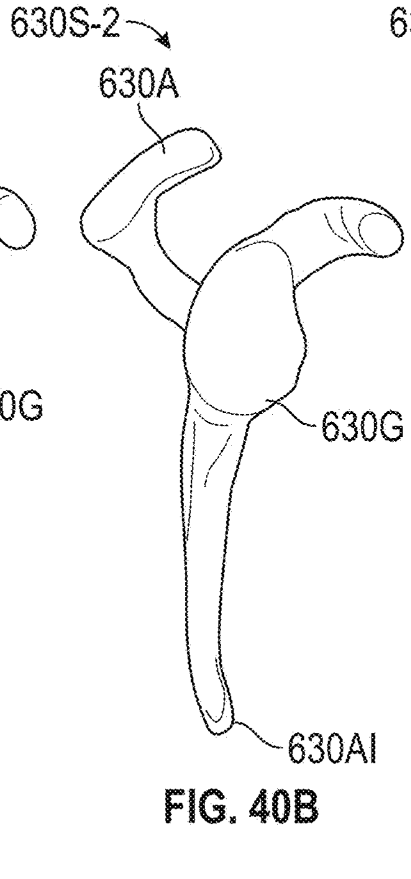
Figure 40C:
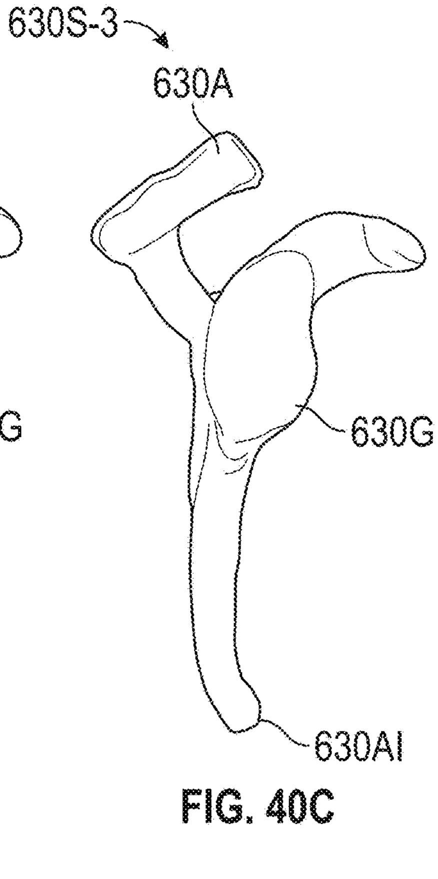

Referring to FIGS. 39A-39C, with continuing reference to FIGS. 2 and 4, the planning environment 28 may be operable to evaluate one or more landmarks of the anatomy to determine changes associated with a condition of the patient, which may affect scapulothoracic motion. Aspects of the acromion may be considered. The landmark characteristics may include (e.g., an amount of) lateralization of an acromion 630A associated with the scapula model 630S. FIGS. 39A-39C disclose scapula models 630S-1 to 630S-3, which may be associated with acromion profiles for the same patient over different periods of time, or which may be associated with the acromion profiles for different patients of a patient population. FIGS. 40A-40C disclose lateral views of the respective scapula models 630S-1 to 630S-3. Each scapula model 630S may include an acromion 630A (see also FIGS. 34-35). In implementations, the spatial module 50 may be operable to determine an amount of lateralization (e.g., pronouncement) of the acromion 630A associated with the scapula model 630S. The comparison module 52 may be operable to determine an angular (e.g., starting) position that scapulothoracic motion may contribute to the overall range of motion of an associated humerus model (e.g., model 530H of FIGS. 36A-36E) based on the determined lateralization of the acromion 630A.

Various techniques for measuring lateralization of the acromion may be utilized. The spatial module 50 may be operable to determine the amount of lateralization of the acromion 630A relative to one or more anatomical landmarks, axes and/or reference planes associated with the scapula model 630S. An amount of lateralization of the acromion may be associated with one or more predefined modes 76 of the SSM 75, such as size, geometry, posture, etc. The amount of lateralization may be associated with a combination of predefined modes 76.

Referring to back to FIG. 35, with continuing reference to FIGS. 2, 4, aspects of the scapula and/or thorax may be considered to determine the scapulothoracic and/or humeroscapular contributions to the range of motion. The curvature and/or shape of the scapula model 430S and/or thorax model 430T may be correlated to patient size. The curvature and/or shape of the scapula may be evaluated with the SSM 75. In implementations, the curvature of the scapula of the patient may be determined based on one or more predefined modes of variation 76 of the SSM 75. The curvature, shape and/or distribution may be associated with a combination of the predefined modes 76. The predefined modes 76 may include a size of the scapula and/or thorax. The predefined modes 76 may include a position and/or orientation of the bone(s) of the thorax relative to each other and/or the scapula of the patient.

The spatial module 50 may be operable to determine various landmark characteristics of the scapula. The landmark characteristics may influence different regions of the scapula. In implementations, a geometry and/or orientation of the angulus inferior may affect deltoid tension. Other landmarks characteristics may include insertion points for the muscular tissue along the humerus and/or scapula. The landmark characteristic(s) may be associated with one or more predefined modes 76 of the SSM 75.

Referring back to FIGS. 40A-40C, with continuing reference to FIGS. 2, 4 and 39A-39C, the scapula models 630S-1 to 630S-3 may be associated with an angulus inferior 660AI (see also 330AI of FIGS. 33 and 430AI of FIG. 35). The anatomical landmark characteristics may include an (e.g., amount of) curvature of the angulus inferior 660AI associated with the scapula model 630S. The scapula models 630S-1 to 630S-3 include profiles of the angulus inferior 630AI having different curvatures for the same patient over different periods of time or for different patients of a patient population. The spatial module 50 may be operable to determine the curvature of the angulus inferior 630AI. Any potential impingement between the scapula model 630S and the thorax model (e.g., 360T of FIGS. 34-35) associated with the scapula and thorax may restrict scapulothoracic movement. If the patient tends to hunch over then the scapula may exhibit a curvature over time. The angulus inferior typically extends straight down to a generally C-shaped geometry. Bones typically follow stress and forces. The force may be typically downward through the angulus inferior. Poor posture may alter the stress on the scapula, in which the forces may be perpendicular to the angulus inferior. The altered stress may cause a curvature of the angulus inferior. The curvature may restrict movement due to impingement with the rib cage. The curvature may restrict scapulothoracic movement because the scapula may now conform to the rib cage.

The statistical shape modeler 72 and/or another portion of the planning environment 28 may be operable to determine the amount of curvature of the angulus inferior 630AI in response to comparing the scapula model 630S of the patient to a representative scapula model of another patient of the representative patient population (e.g., FIG. 35). The statistical shape modeler 72 and/or another portion of the planning environment 28 may be operable to select the representative scapula model in response to analyzing the representative patient population within SSM 75. An amount of curvature of the angulus inferior 630AI may be associated with one or more predefined modes 76 of the SSM 75, such as size, geometry, posture, etc. The curvature of the angular inferior 630AI may be associated with a combination of predefined modes 76. The SSM modeler 72 may be configured to evaluate two or more predefined modes 76 concurrently to determine a best fit between the patient anatomy and the anatomy of another patient associated with the SSM 75. Any of the factors disclosed herein, alone and/or in combination, may be utilized in combination with the SSM 75 and/or associated mode(s) 76 to predict or otherwise determine scapulothoracic movement associated with a range of motion.

Other factors associated with the glenoid may include superior tilt. An increase in superior tilt may reduce the amount of scapulothoracic movement. The scapula model 630S may include a glenoid model 630G. The spatial module 50 may be configured to determine the amount of superior tilt associated with the glenoid model 630G (e.g., relative to a plane of the scapula model 630S and/or relative to a kinematic plane of the patient).

Figure 8:
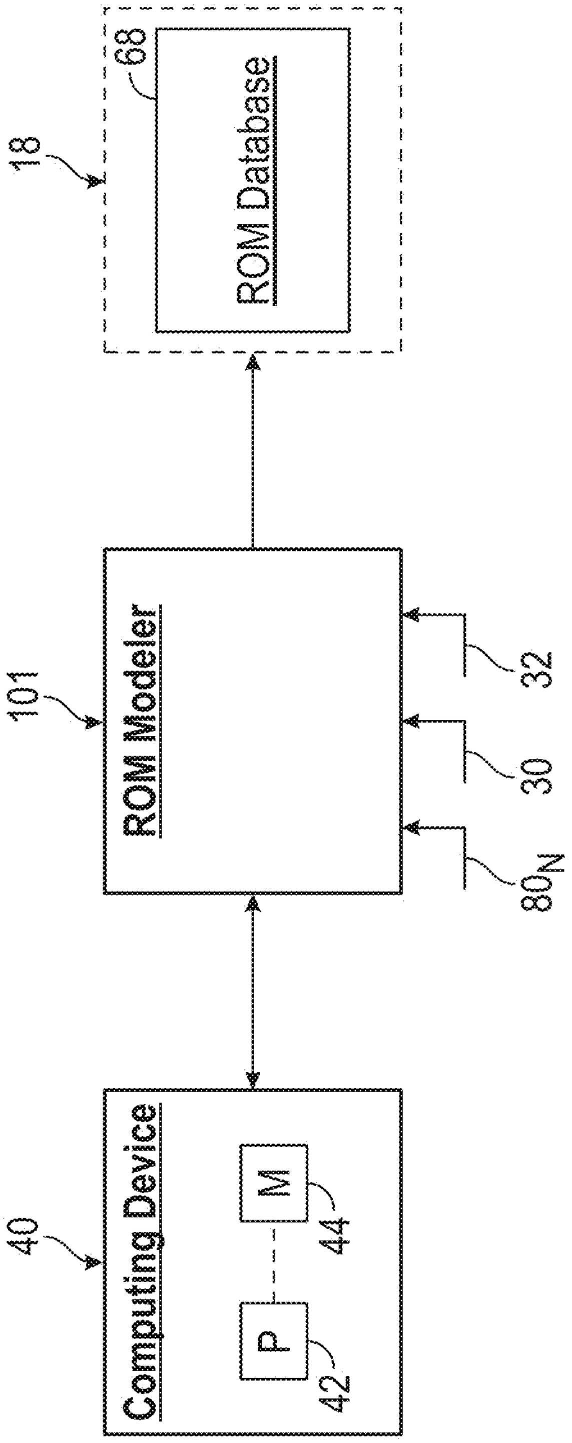
FIG. 8 discloses aspects of the surgical planning system of FIG. 1 including a range of motion modeler.
Figure 41A:
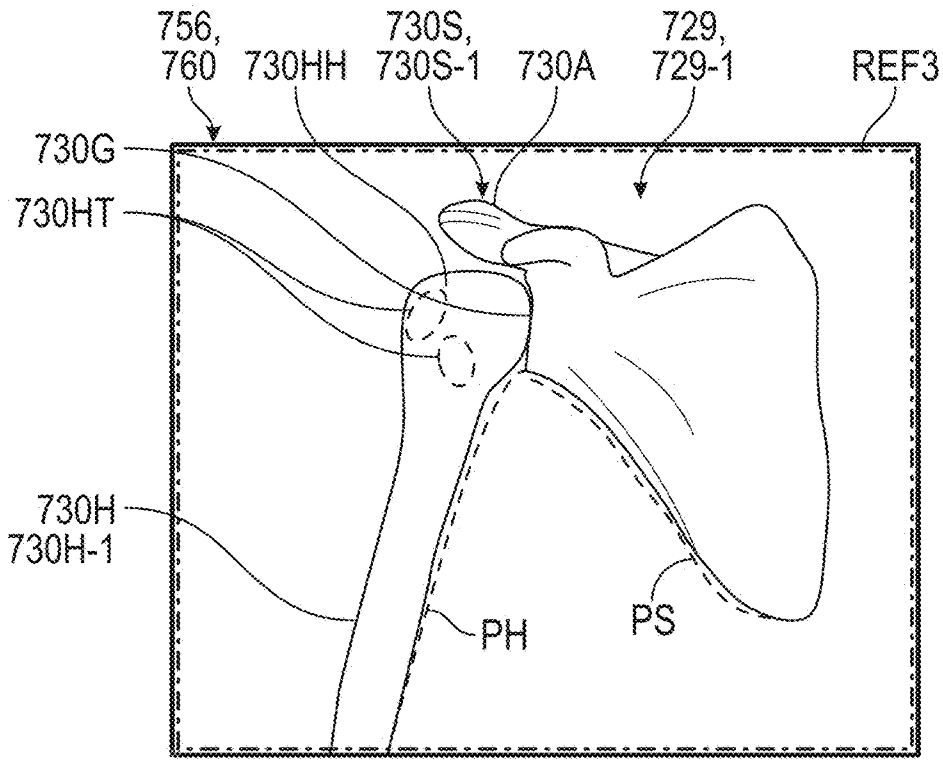
FIGS. 41A-41B disclose shoulder models associated with a gothic arch.
Figure 41B:
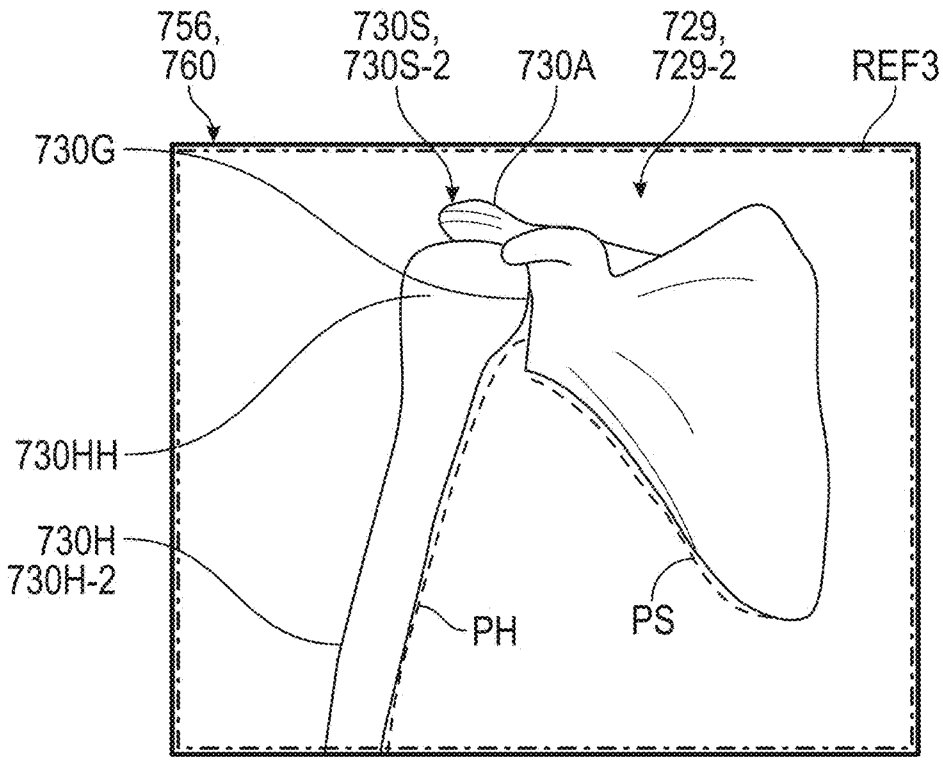

Referring to FIG. 41A-41B, with continuing reference to FIGS. 2, 4 and 8, a humerus model 730H may include a humeral head 730HH associated with a humeral head of the anatomy. One or more aspects of the humerus may be utilized to predict or otherwise determine scapulothoracic movement, including various landmarks. The landmarks may include the (e.g., greater or lesser) tuberosities 730HT of the humeral head (FIG. 41A).

The landmarks may include a position of the humeral head relative to the glenoid and/or acromion. The spatial module 50 may be configured to determine a superior migration of the humeral head 730HH, including relative to the glenoid model 730G and/or acromion model 730A. The superior migration may be determined relative to one or more landmarks and/or kinematic planes of the anatomy. The humeral head may be relatively superior to the glenoid (e.g., "riding high"), which may limit rotation of the humerus relative to the scapula. Superior migration may cause impingement between the humerus and acromion. The ROM modeler 101 and/or another portion of the planning environment 28 may be operable to determine impingement, scapulothoracic movement and/or the associated range of motion based on the determined superior migration.

Retrotorsion of the humerus may be measured or otherwise determined. Severe retrotorsion may be caused by the humeral head being offset from the glenoid, rather than sitting in the joint. The spatial module 50 may be configured to determine a retrotorsion of the humerus model 730H relative to the glenoid model 730G.

Another factor associated with the glenoid and humerus may include the presence of a broken "gothic arch" condition. The gothic arch may be established by the scapula neck and the calcar region of the humerus. The landmark characteristics may include a broken gothic arch condition associated with a position of a humerus bone model 730H relative to a scapula bone model 730S. The spatial module 50 may be operable to determine a profile PS of the scapula neck associated with a scapula model 730S and/or a profile PH of the calcar region associated with a humerus model 730H. the profiles PH, PS may be established in a common plane REF3. FIG. 41A may be representative of an intact gothic arch. FIG. 41B may be representative of a broken gothic arch. A broken gothic arch may be indicated by a humeral head that has risen. A broken gothic arch may indicate a fatty infiltration of the rotator cuff and/or an irreparable cuff, which may cause pain or discomfort. The patient may avoid use the rotator cuff by compensating with scapulothoracic movement. Superior tilt of the glenoid or a broken gothic arch may indicate superior migration of the humerus. The spatial module 50 may be operable to determine a gothic arch condition, which may include whether the gothic arch may be broken or not (e.g., binary value).

Figure 42B:
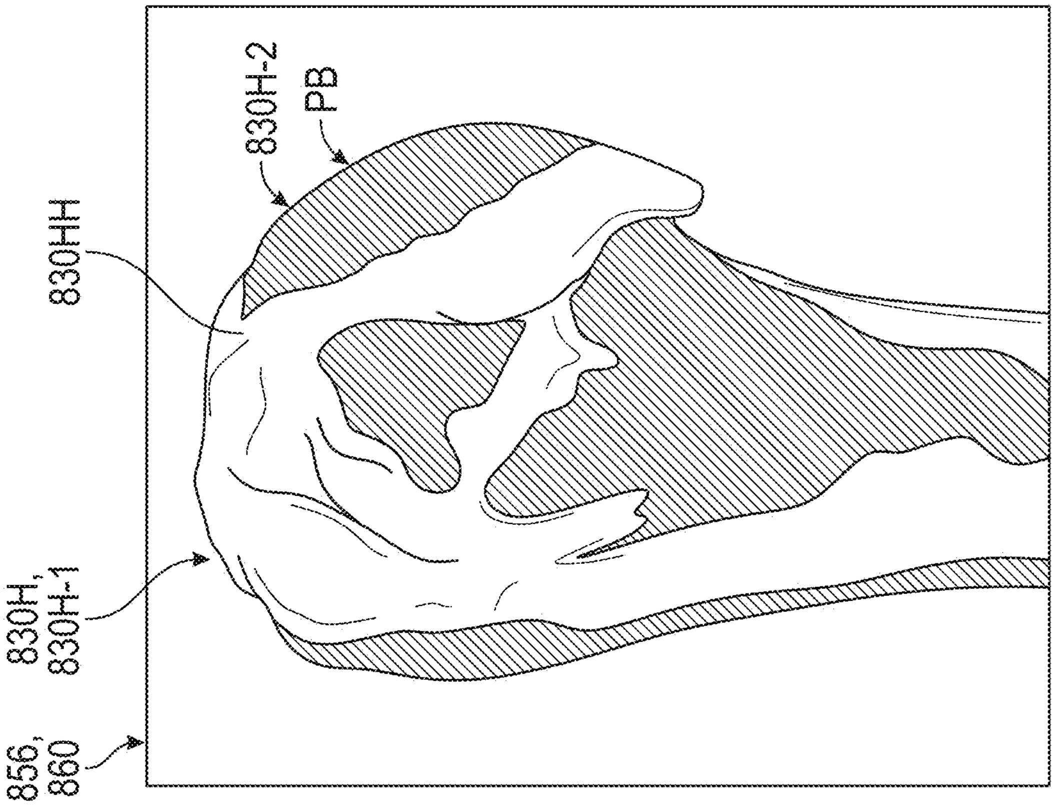
FIGS. 42A-42B disclose a humerus model.
Figure 42A:
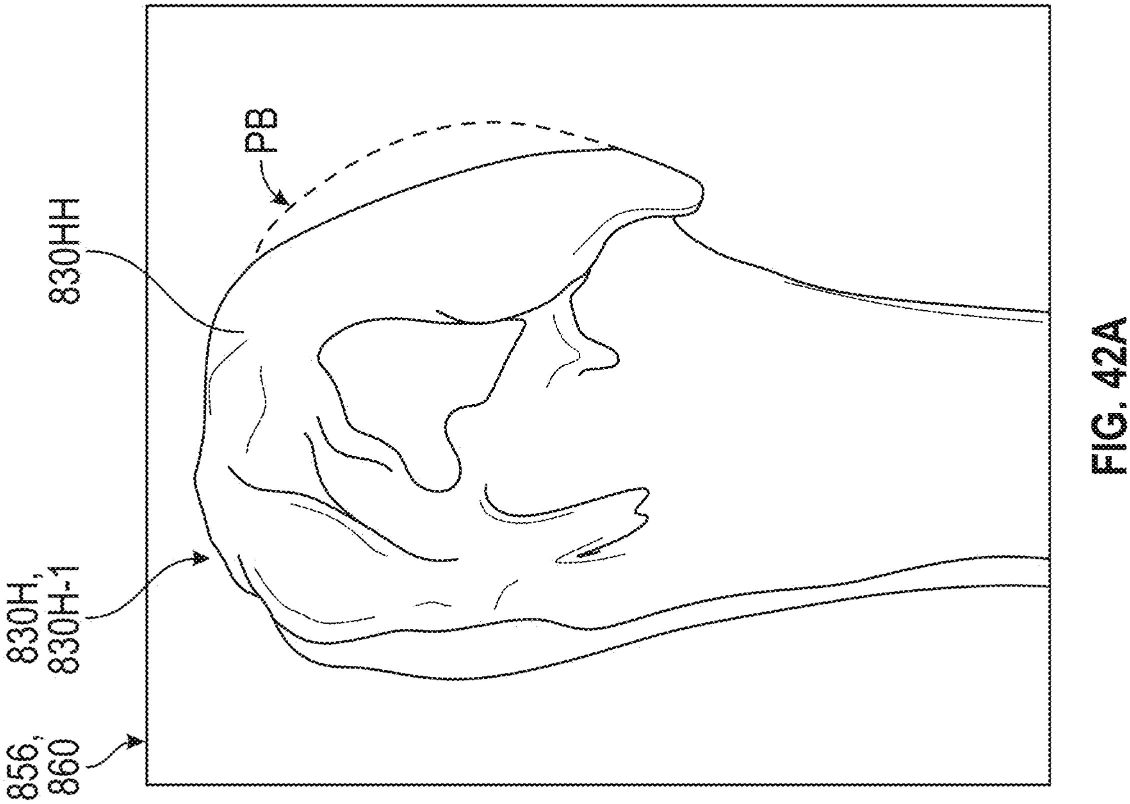

Referring to FIGS. 42A-42B, with continuing reference to FIGS. 2 and 4, another factor may include a condition of the humeral head. The condition may be associated with osteonecrosis, in which an (e.g., articular) portion of the humeral head may lose its blood supply, die and collapse. A collapsed condition may impair mobility and/or cause pain or discomfort when the patient attempts to move their arm, which may lead the patient to compensating with scapulothoracic movement. The landmark characteristics may include a collapsed condition of a humerus model with respect to a premorbid boundary. The spatial module 50 may be operable to determine whether a humeral head 830HH of the humerus model 830H-1 of the patient may be collapsed in response to comparing the humeral head 830HH relative to a premorbid boundary PB (shown in dashed lines in FIG. 42A). The SSM modeler 72 and/or another portion of the planning environment 28 may be operable to determine the collapsed condition of the humerus model 830H-1 of the patient in response to comparing the humerus model 830H-1 of the patient to the premorbid boundary PB associated with a representative humerus model 830H-2 of another patient of the representative patient population. The premorbid boundary PB may be established (e.g., approximated) by the humeral head 830HH associated with the humerus model 830H-2 of another patient, which may be selected based on the SSM 75. The statistical shape modeler 72 may be configured to fit the humeral head model 830H-1 of the patient within the premorbid boundary PB represented by a profile of the humeral head 830HH of the humerus model 830H-2.

The comparison module 52 may be operable to determine (e.g., adjust) the humeroscapular and scapulothoracic contributions in response to determining a collapsed condition of the humeral head. The scapulothoracic contribution may be increased and the humeroscapular contribution may be decreased in response to determining occurrence of the collapsed condition. In implementations, the SSM modeler 72 may assign an AMC 80 to the humerus model 830H-1 of the patient corresponding to the humerus model 830H of another patient that may most closely fit a profile of the humerus, which may include a collapsed humeral head. The AMC 80 may include any of the parameters disclosed herein, such as humeroscapular and/or scapulothoracic contributions, which may be utilized to determine range of motion of the patient humerus model 830H-1.

Referring back to FIGS. 21-26, with continuing reference to FIG. 2, another factor may include the starting position of the humerus. The planning environment 28 may be operable to determine a starting position of the humerus model 330H and/or a starting position of the scapula model 330S based on one or more posture parameters. The spatial module 50 may be operable to set an initial position of the humerus bone model 330H based on the determined posture and/or various characteristics of the scapula bone model 330S and/or thorax bone model 330T. The spatial module 50 may be operable to set an initial position of the scapula bone model 330S based on the determined posture and/or various characteristics of the thorax bone model 330T, including the position and/or orientation of the bone(s) associated with the thorax bone model 330T. The posture of the patient may influence movement (e.g., abduction) of the arm. The posture may be categorized as Types A-C. Type C posture may be associated with a relatively lesser amount of scapulothoracic movement than Type A or B due to a position of the scapula, including abduction of the arm.

The planning environment 28 may be operable to determine a contribution (e.g., amount) of the scapulothoracic movement to the range of motion based on one or more posture parameters associated with a posture of the patient. The posture parameter(s) may include a scapular angle associated with a scapula. The posture parameter(s) may include a set of posture types. Each of the posture types may be associated with a discrete range of scapular angles. The planning environment 28 may be operable to determine the posture parameter(s) and/or receive the posture parameter(s) based on a user input. The planning environment 28 may be operable to determine the humeroscapular contribution based on the starting position of the humerus model 330H. The planning environment 28 may be operable to determine the scapulothoracic contribution based on the starting position of the scapula model 330S.

The comparison module 52 may be operable to determine the scapulothoracic component of the range of motion and/or numerical relationship(s) (e.g., ratio) between the scapulothoracic and humeroscapular contributions based on the posture of the patient. The surgeon or clinical user may interact with the user interface 356 to adjust or otherwise determine a position of an implant model(s) 332 based on the determined posture and/or contribution(s). This may occur because certain acts of daily living may not be possible even considering scapulothoracic movement, or because the implant model(s) 332 may not be in a configuration that may prioritize or increase the amount of recruitment from the deltoid and/or scapulothoracic movement. The scapulothoracic recruitment may differ based on the posture and/or associated posture type. For a reverse implant, the patient may rely heavily on scapulothoracic movement to drive upward movement of the arm. The surgeon or clinical user may interact with the user interface 356 to position the implant model 332 to maximize or otherwise increase abduction associated with the posture of the patient. The comparison module 52 may be operable to determine the posture and/or posture type utilizing any of the techniques disclosed herein.

The comparison module 52 may be operable to assign different amounts associated with scapulothoracic motion to the posture types. The assigned amount may be the same or may differ from the actual amount for the patient. The assigned amount may serve as an approximation, which may be suitable for planning. The predetermined amount may be approximately 30% for Type A posture, approximately 20% for Type B posture and approximately 10% for Type C posture. But, for external rotation there may be minor amounts of movement of the scapula. Type A posture may be best case, whereas Type C posture may be worst case. The comparison module 52 may be operable to add 5%, 15% and 25% to the humeroscapular range of motion for Type A, B and C posture types, respectively, to estimate the overall range of motion.

Figure 47:
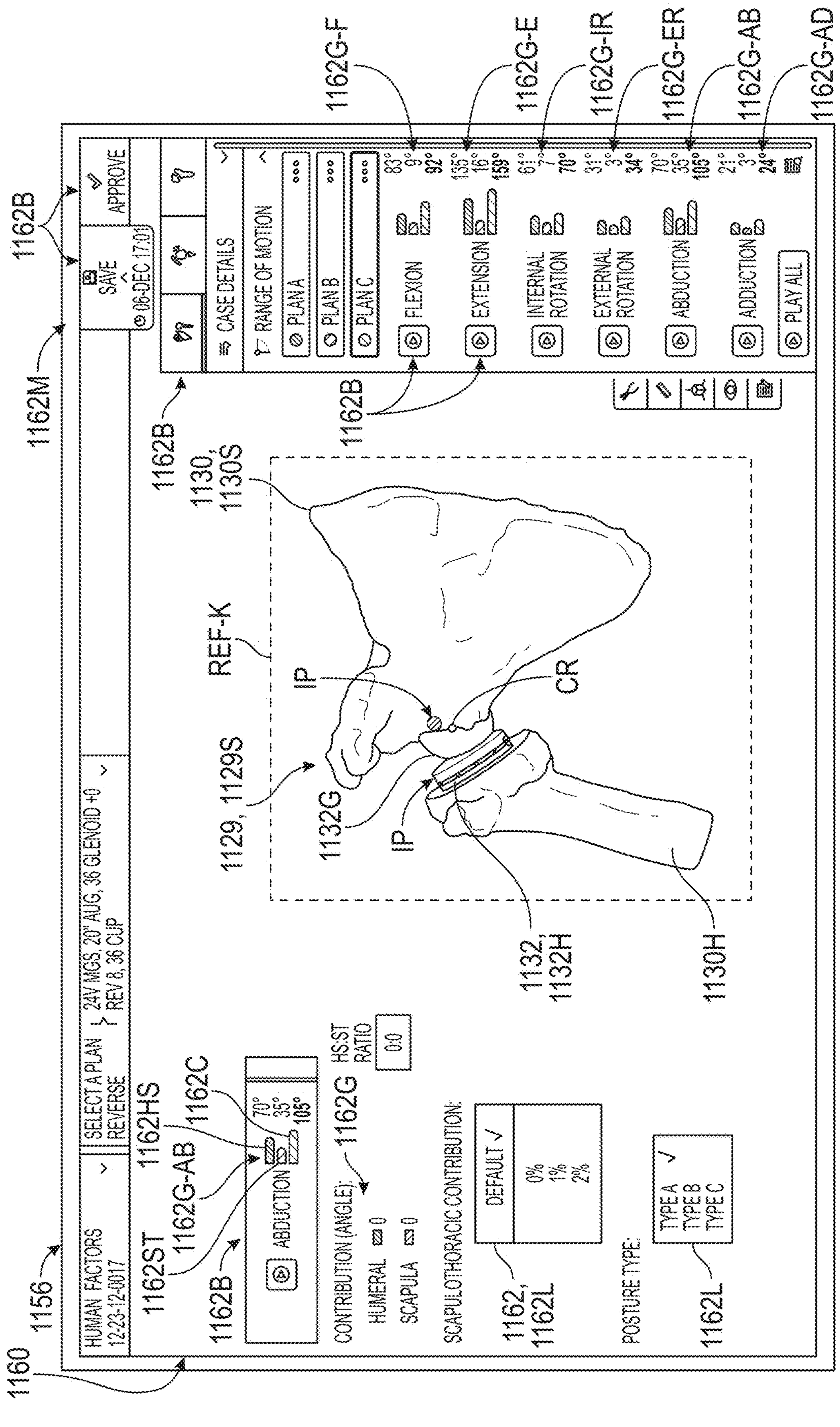
FIGS. 47-50 disclose a shoulder model in a user interface according to another implementation.
Figure 48:
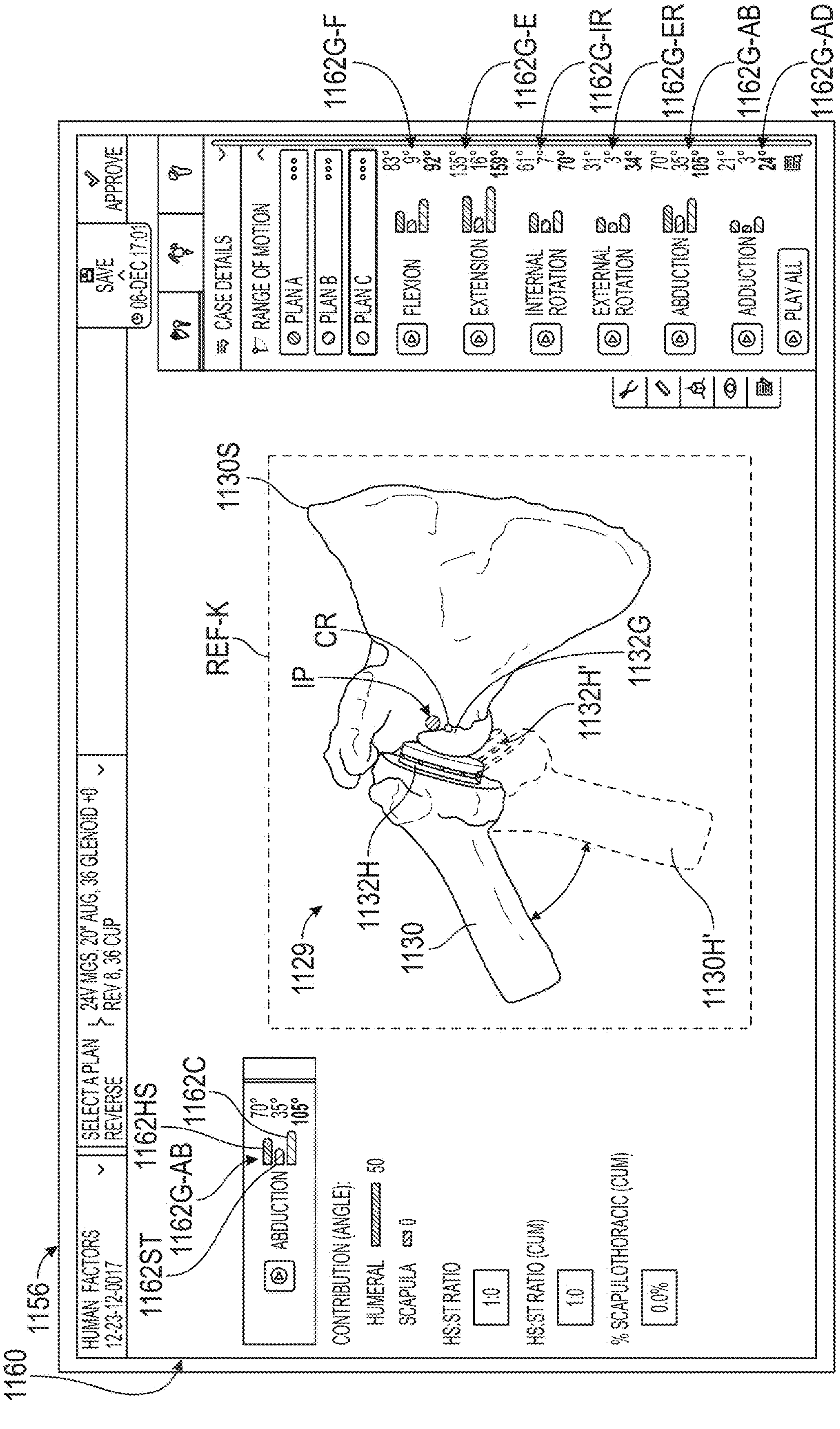

The planning environment 28 may be operable to automatically determine the posture and may set (e.g., adjust) the scapulothoracic contribution based on posture. In implementations, the surgeon or clinical user may interact with the user interface 56 to select the posture type. In the implementation of FIG. 47, the surgeon or clinical user may interact with a drop down list 1162L and/or another portion of the user interface 1156 to select a posture type (e.g., posture A). In the implementation of FIG. 22, the surgeon or clinical user may interact with one or more radial buttons 362R to select the scapular angle (e.g., 30 degrees), which may be associated with a respective posture type.

Other techniques for determining posture may be utilized. In implementations, the planning environment 28 may be operable to determine posture based on a curvature of the spine. The curvature may be established by the vertebrae associated with the thorax bone model 330T. The spatial module 50 may be operable to determine the curvature. The statistical shape modeler 72 may be operable to assign an AMC 80 to the anatomical model 329 based on the curvature. Curvature of the spine may be associated with one or more modes of variation 76 of a (e.g., thorax) SSM 75. The curvature may be associated with a standing or lying position of the patient, which may be associated with an acquisition orientation of the imagery.

Figure 43A:
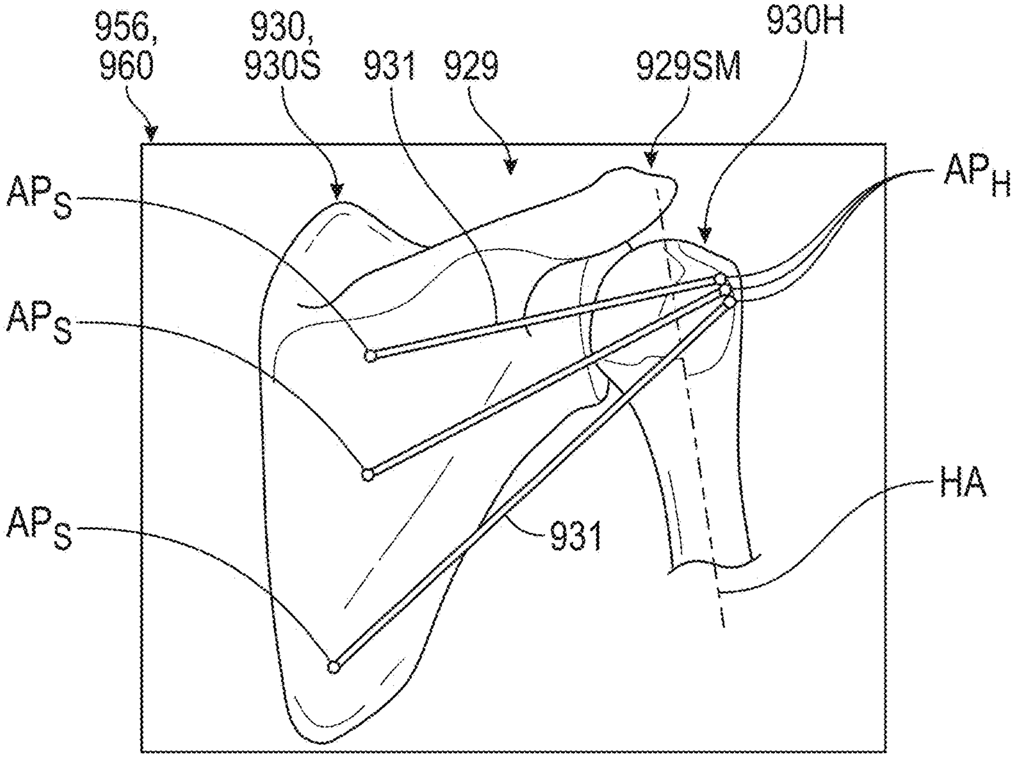
FIGS. 43A-43B and 44A-44B disclose a ligament model.
Figure 43B:
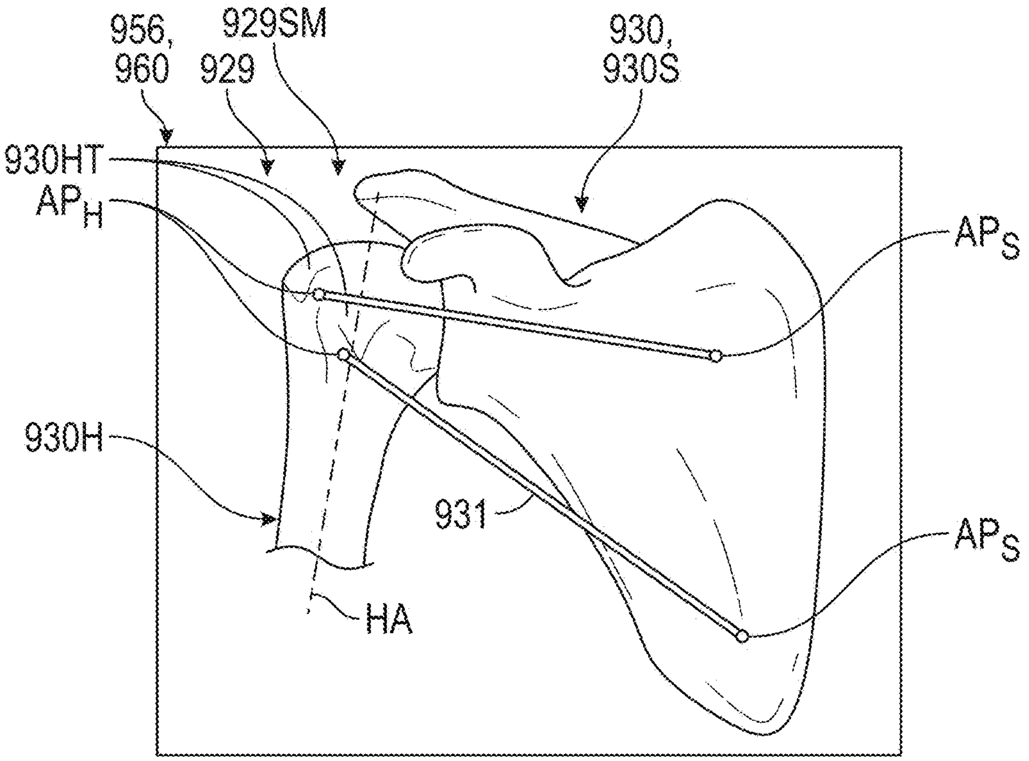
Figure 44A:
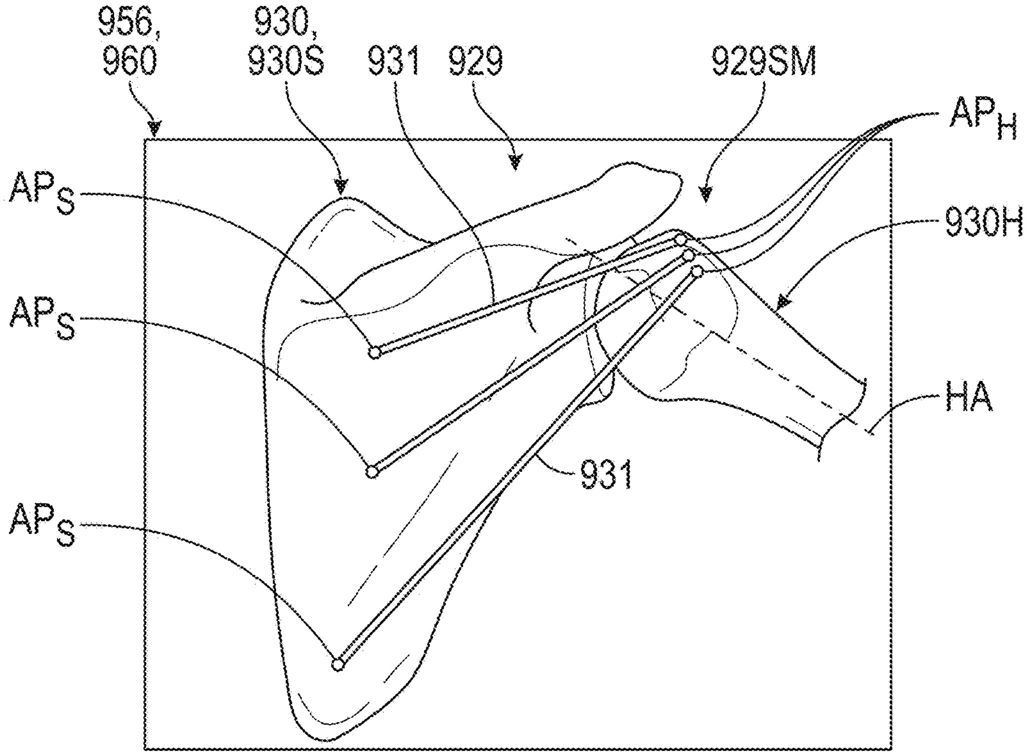
Figure 44B:
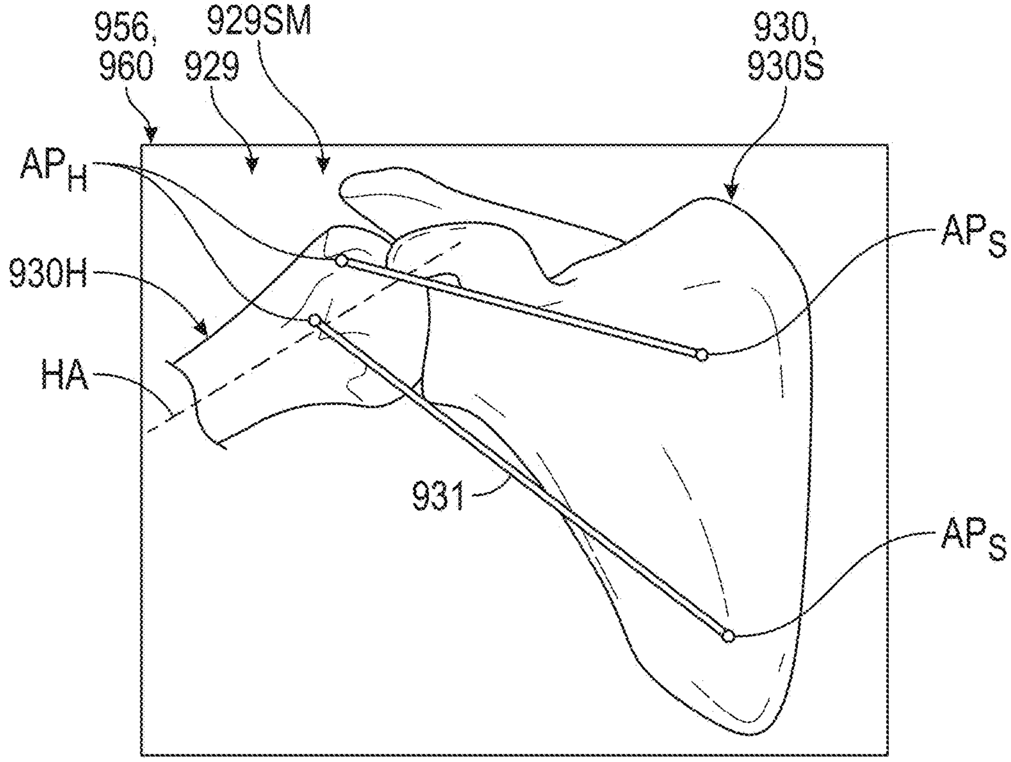

Referring to FIGS. 43A-43B and 44A-44B, with continuing reference to FIGS. 2 and 8, another factor for predicting or otherwise determining scapulothoracic movement may include condition(s) of the soft tissue associated with the joint(s). FIGS. 43A-43B may be associated with a humerus model 930H in a first position relative to a scapula model 930S. FIGS. 44A-44B may be associated with the humerus model 930H in a second position relative to the scapula model 930S. The scapula model 930S and humerus model 930H may be associated with a shoulder joint model 929SM. The first position may be associated with approximately 10 degrees of abduction. The second position may be associated with approximately 60 degrees of abduction. The comparison module 52 and/or another portion of the planning environment 28 may be configured to determine the scapulothoracic contribution to the range of motion based on determining the condition(s) of the soft tissue. Various techniques may be utilized to determine the soft tissue condition(s), such as evaluating MRI imagery of the patient anatomy. The ROM modeler 101 may be operable to perform a range of motion simulation based on the determined soft tissue condition(s). Scapulothoracic motion may be affected based on the condition of the rotator cuff and how elastic the tissue may be. Other soft tissue conditions may include joint tension (e.g., tightness of joint), such as conjoint tension which may affect external rotation of the humerus.

Some patients may experience a rotator cuff deficit. Scapulothoracic movement may occur at a relatively earlier position with a cuff-deficient shoulder. The patient may be incapable of lifting the humerus and therefore may compensate with movement of the scapula.

With abduction, scapulothoracic movement may depend on the condition of the supraspinatus and infraspinatus. If there is fatty infiltration of the supraspinatus and/or infraspinatus, then the scapulothoracic contribution may be greater than the humeroscapular contribution to the range of motion. This may be because it may hurt to move the humerus upward in relation to the scapula since the two abductors that move the humerus may be fatty-infiltrated and in poor condition. Accordingly, the patient may compensate by moving the scapula upward.

Other factors that may be considered to predict or otherwise determine scapulothoracic movement may include the bony structures (i.e., the tuberosities) that may support the rotator cuff and/or the remodeling of the bony structures. Various indicators may play a role in deltoid insertion position and mechanical lever arm potential of the deltoid.

The indicators may include the insertion points of the muscular structures performing these motions.

The planning environment 28 may be operable to determine one or more soft tissue attachment (e.g., insertion) points AP along adjoining bone models 930, such as the scapula bone model 930S and/or humerus bone model 930H. The planning environment 28 may be operable to determine an/the amount of the scapulothoracic movement based the soft tissue attachment point(s) AP. The spatial module 50 and/or another portion of the planning environment 28 may be configured to determine a location of soft tissue attachment point(s) AP based on one or more landmarks of the respective bone model(s) 930. The attachment points AP may include one or more scapula attachment points $AP_S$ and/or one or more humerus attachment points $AP_H$. The attachment points AP may be distributed along the respective bone model 930. In implementations, the surgeon or clinician may interact with the display window 960 and/or another portion of the user interface 956 to set the position of the attachment points AP. The spatial module 50 may be operable to determine the attachment point(s) AP utilizing various techniques, such as bone density based on the associated imagery of the patient anatomy. Localized bone density at the attachment points AP may differ from adjacent portions of the bone.

The spatial module 50 may be operable to establish one or more ligament models 931, which may be associated with the anatomical model 929 and/or associated bone models 930. The ligament model(s) 931 may be representative of ligaments of the patient. The ligament model(s) 931 may be dimensioned to span between and interconnect respective pairs of the scapula and humerus attachment points $AP_S$, $AP_H$. Various characteristics may be assigned to the ligament model 931, including an elasticity suitable for simulating movement of the shoulder joint. The ROM modeler 101 may be operable to perform a range of motion simulation based on the attachment point(s) AP and/or associated ligament model(s) 931. The comparison module 52 may be operable to determine the scapulothoracic contribution to the range of motion and/or numerical relationship(s) between the scapulothoracic and humeroscapular contributions based on the attachment point(s) AP and/or associated ligament model(s) 931, which may be displayed in the user interface 956 utilizing any of the techniques disclosed herein.

A rotator cuff deficit may be determined based on soft tissue point(s) $AP_H$ along the humeral head. The soft tissue points $AP_H$ may be associated with the rotator cuff, including the supraspinatus and infraspinatus. The humerus may degenerate at the soft tissue points $AP_H$, which may cause the bone to remodel. The spatial module 50 may be operable to evaluate the bone at one or more of the soft tissue points $AP_H$, including any remodeling, to predict or otherwise determine a scapulothoracic contribution to the range of motion of the humerus.

Patients that present for a reverse shoulder arthroplasty may have a supraspinatus and infraspinatus which may be heavily fatty-infiltrated. Fatty infiltration of the rotator cuff muscles may cause discomfort or pain when moving the humerus. The patient may compensate with relatively greater scapulothoracic movement to avoid moving the humerus. Since shoulder arthroplasty is an elective procedure, the patient may have progressed into a deficient state over many years and may have grown accustomed to compensating with movement the shoulder. In so doing, the bone may morph and remodel. If the insertion points of the supraspinatus and infraspinatus have not been loaded for a period of time (e.g., a few years), the supraspinatus and infraspinatus may degenerate. The spatial module 50 may be operable to evaluate how pronounced the tuberosities 930HT of the humeral head 930HH (e.g., FIG. 43B). The comparison module 52 may be operable to determine at what angle scapulothoracic movement may begin to occur relative to the range of motion based on the determined pronouncement.

The disclosed factors may be affected by various characteristics of the selected implant(s), including implant type (e.g., anatomical or reverse), size, position and/or orientation. Implant position may affect how much and/or when scapulothoracic movement may occur relative to a range of motion of the arm.

In a reverse shoulder procedure, the deltoid may provide abduction of the arm instead of the supraspinatus. Abduction by the deltoid may be limited. After the limit is reached, scapulothoracic movement may provide a majority, or all, of the overall movement of the arm.

Figure 45:
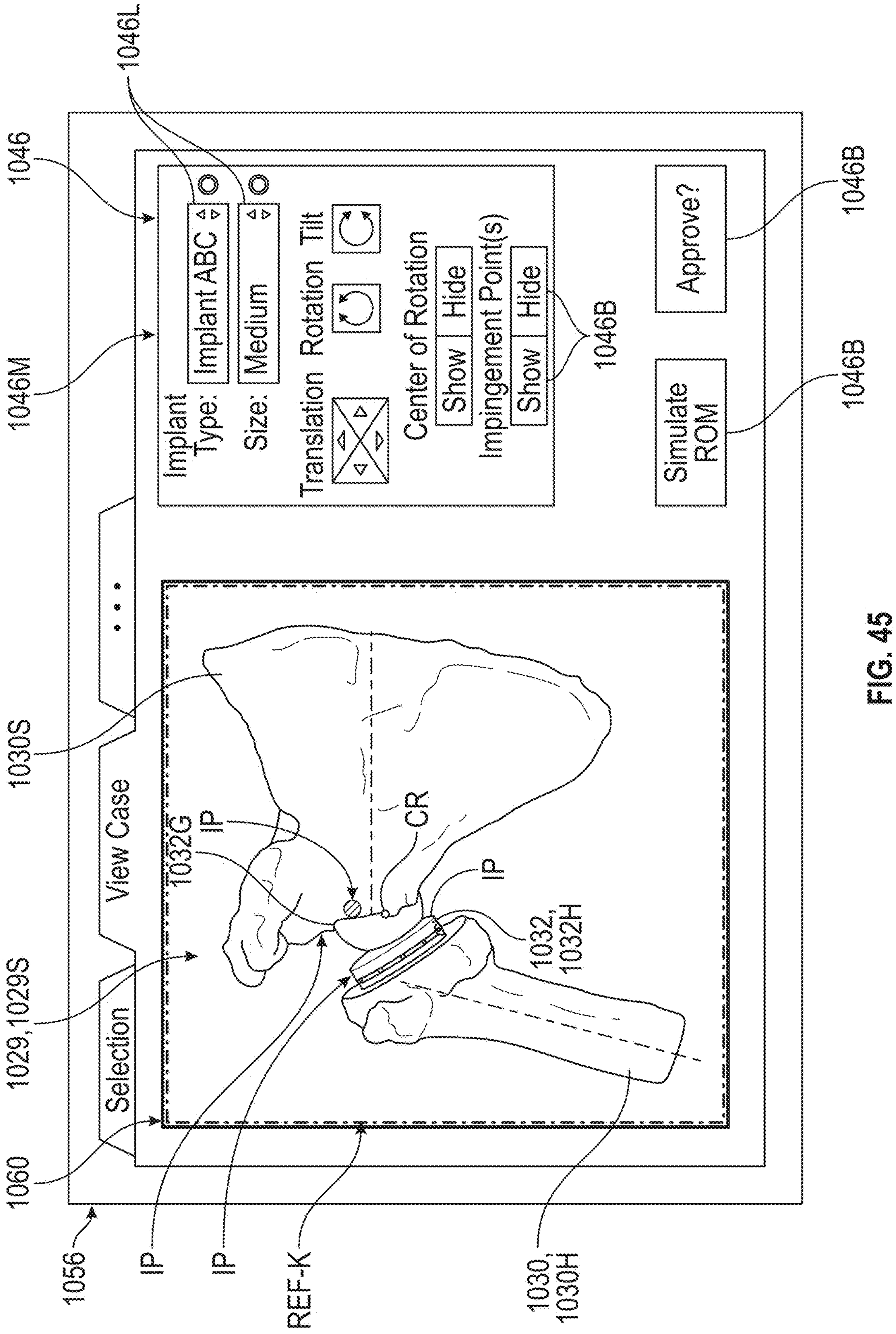
FIGS. 45-46 disclose a shoulder model in a user interface.
Figure 46:
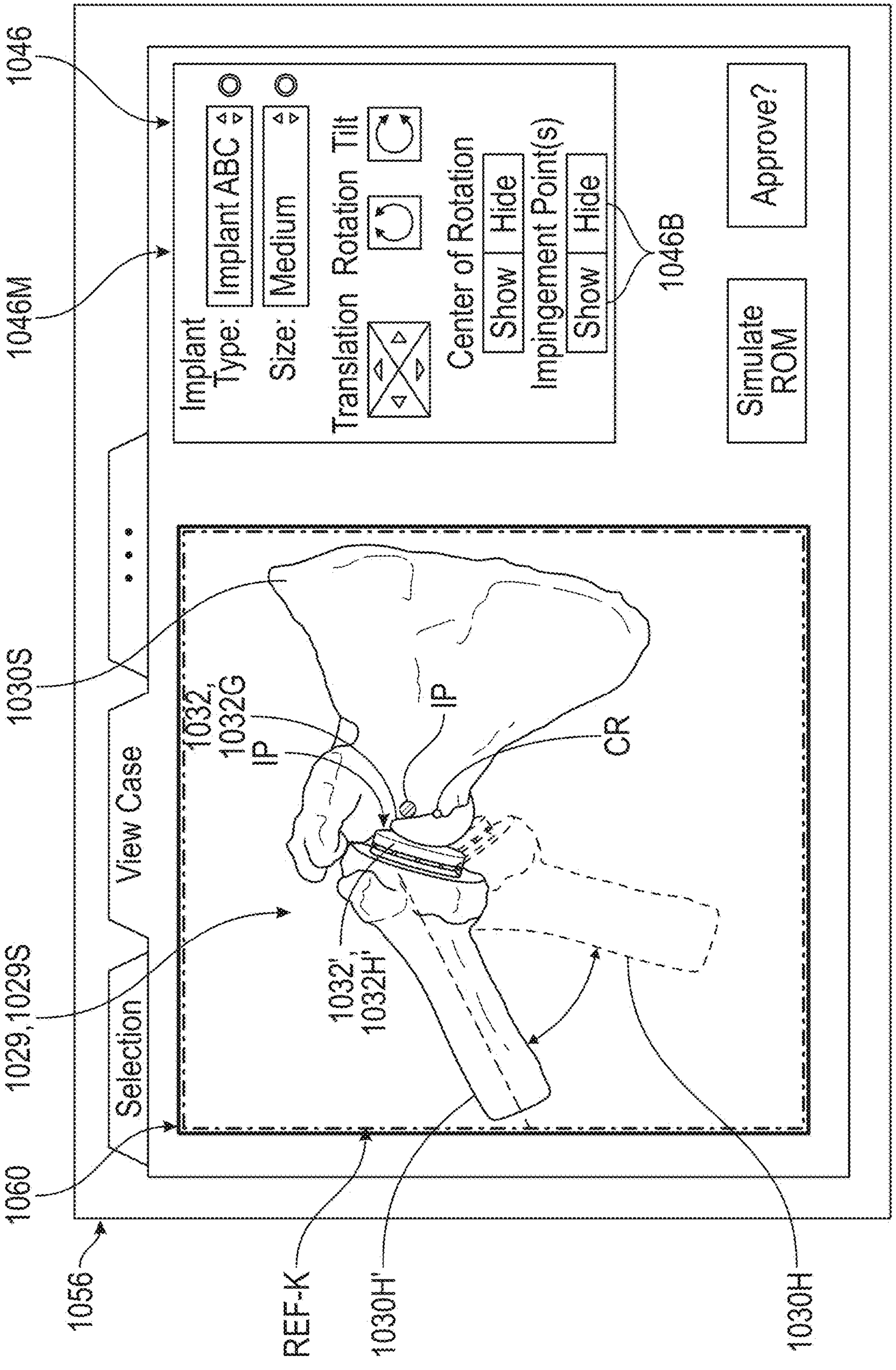

Referring to FIGS. 45-46, with continuing reference to FIGS. 2 and 8, the planning environment 28 may be operable to determine the scapulothoracic and/or humeroscapular contributions to the range of motion based on one or more implant characteristics for restoring functionality to the joint. The implant characteristic(s) may be specified in the surgical plan 36. The implant characteristic(s) may include a position, orientation and/or geometry of the implant, which may be associated with a respective implant model 32. Implant head sizes may be associated with respective amounts of lateralization and/or centers of rotation. The surgeon or clinical user may select and position the implant to achieve acts of daily living/lifestyle goals for the patient. The implant may be associated with an implant model 32. The implant model 32 may include a concave or convex articulation surface dimensioned to articulate with an adjacent bone or implant.

In the implementation of FIGS. 45-46, the anatomical model 1029 may include one or more bone models 1030. The bone models 1030 may include a scapula bone model 1030S and/or humerus bone model 1030H. One or more implant models 1032 may be positioned relative to the bone models 1030. The implant models 1032 may include a glenoid implant model 1032G positioned relative to a glenoid of the scapula model 1030S and/or a humerus implant model 1032H positioned relative to a humeral head of the humerus model 1030H. The glenoid implant model 1032G may be associated with a glenosphere securable to a glenoid. The humerus implant model 1032H may be associated with a humeral cup securable to a humerus. In other implementations, the glenoid implant model 1032G may be associated with a pad securable to the glenoid. The humerus implant model 1032H may be associated with a humeral head securable to a humerus.

The ROM modeler 101 may be operable to determine (e.g., predict) and/or simulate a range of motion of the humerus model 1030H associated with scapulothoracic movement of the scapula model 1030S based on one or more impingement (e.g., collision) points (e.g., zones), a degree of lateralization and/or a center of rotation of the joint. FIG. 45 discloses the humerus model 1030H and associated implant model 1032H in a first (e.g., starting) position. FIG. 46 discloses the humerus model 1030H and associated implant model 1032H in a second (e.g., intermediate or stopping) position, as indicated by humerus model 1030H' and associated implant model 1032H'. The display module 48 may be configured to display the bone models 1030, 1030' and/or implant models 1032, 1032' in a display window 1060 of the user interface 1056.

The center of rotation established by the implant model 1032 (e.g., glenosphere associated with model 1032G) may affect the impingement/collision points. If the center of rotation is medialized, the joint may have relatively low tension (e.g., "laxed"). If the center of rotation is lateralized, the joint may have relatively high tension (e.g., "over-stuffed"), which may cause pain. The patient may compensate to avoid or otherwise reduce the pain, which may result in a relatively earlier employment of the scapulothoracic movement. The impingement point(s) may be established based on bone-to-bone, bone-to-implant and/or implant-to-implant collisions. If the implant is positioned such that there is an implant-to-implant or implant-to-bone collision, the scapulothoracic movement may occur at a relatively earlier stage (e.g., lesser degree of abduction).

The spatial module 50 may be operable to determine one or more impingement points IP between adjacent bone model(s) 1030 of the anatomical model 1029 and/or implant model(s) 1032, including between the humerus implant model 1032H and the glenoid implant model 1032G and/or the scapula bone model 1030S. Each impingement point IP may be a single coordinate or may be a localized region along the associated surface. The spatial module 50 may be operable to determine a center of rotation CR associated with the joint. The center of rotation CR may be established by the glenoid implant model 1032G. The humerus implant model 1032H and/or humerus bone model 1030H may be rotatable in one or more directions about the center of rotation CR.

The ROM modeler 101 may be configured to determine a range of motion of the humerus bone model 1130H with respect to one or more kinematic planes REF-K associated with the patient. A global reference system may be established relative to one or more kinematic planes, including any of the kinematic planes disclosed herein. Registering the bone model(s) 1130 in the global reference system may improve determining a range of motion of the associated bone of the patient.

The spatial module 50 may be operable to determine the impingement point(s) IP based on the center of rotation CR. The ROM modeler 101 may be operable to perform a range of motion simulation in one or more kinematic planes REF-K to determine the impingement point(s) IP. In implementations, the surgeon or clinical user may interact with the display window 1060 and/or another portion of the user interface 1056 to select or otherwise specify the center of rotation CR. The display module 48 may be operable to display the center of rotation CR and/or impingement point (s) IP in the display window 1060. The comparison module 52 may be operable to determine the scapulothoracic and/or humeroscapular contributions to the range of motion based on the center of rotation CR and/or impingement point(s) IP. The ROM modeler 101 may be configured to perform a range of motion simulation based on the center of rotation CR to determine the impingement point(s) IP.

The ROM modeler 101 may be configured to perform a range of motion simulation along or otherwise relative to the kinematic plane(s) REF-K. The range of motion modeler 101 may be configured to align the humerus bone model 1030H relative to the kinematic plane(s) REF-K. Various kinematic planes may be utilized, such as a coronal (e.g., frontal), axial (e.g., horizontal or transverse) and/or a sagittal (e.g., longitudinal) plane of the patient. The coronal plane may be associated with deflection and/or extension of an associated bone. The axial plane may be associated with internal and/or external rotation of an associated bone. The sagittal plane may be associated with abduction and/or adduction of an associated bone. The range of motion modeler 101 may be configured to move the humerus bone model 1030H along the kinematic plane REF-K. In the implementation of FIG. 46, the range of motion modeler 101 may be configured to move the humerus bone model 1030H in adduction and/or abduction to determine a range of motion relative to the kinematic plane REF-K.

The ROM modeler 101 and/or another portion of the planning environment 28 may be operable to determine range of motion based on any of the factors disclosed herein. The comparison module 52 may be operable to determine scapulothoracic and/or humeroscapular movements based on the based on the determined factor(s) and one or more range of motion simulations. The comparison module 52 may be operable to determine the scapulothoracic contribution to the range of motion and/or a ratio between the scapulothoracic and humeroscapular contributions based on the determined factor(s).

The surgeon or clinical user may interact with the planning environment 28 to establish a surgical plan 36 based on the determined scapulothoracic and/or humeroscapular contributions to achieve one or more acts of daily living and/or lifestyle goals and/or evaluate range of motion with respect to planned implant positioning. The scapulothoracic and/or humeroscapular contributions determined (e.g., assigned or predicted) for the anatomical model 29 and/or bone model(s) 30 of the patient may be established based on any of the factors and/or other patient characteristics disclosed herein, alone and/or in combination. The ROM modeler 101 may be operable to perform a range of motion simulation based on the contribution(s). Any of the factors and/or other patient characteristics disclosed herein may establish one or more predefined modes 76 of the SSM 75. The SSM 75 may be utilized to determine the scapulothoracic and/or humeroscapular contributions to the range of motion in one or more kinematic planes. An implant model 32 may be assigned a default starting position and/or orientation relative to the respective bone model 30. The comparison module 52 may be operable adjust the default starting position and/or orientation of the implant model 32 based on the determined scapulothoracic and/or humeroscapular contributions.

Methods of planning an orthopaedic procedure may include any of the techniques disclosed herein. A three-dimensional scapula model and a three-dimensional thorax model of a patient may be positioned relative to each other to establish a scapulothoracic joint model. A three-dimensional humerus model may be positioned relative to the scapula model to establish a shoulder joint model. At least one implant model may be positioned at a respective implant position relative to the shoulder joint model. An overall range of motion of the humerus model may be determining relative to one or more kinematic planes based on the position of the at least one implant model.

A scapulothoracic contribution of scapulothoracic movement between the scapula model and the thorax model may be determined for a range of motion. A humeroscapular contribution of humeroscapular movement between the humerus model and the scapula model may be determined for the range of motion. Determining the scapulothoracic movement may include comparing the scapula model and the thorax model of the patient to a three-dimensional representative scapula model and a three-dimensional representative thorax model of another patient of a representative patient population. Determining the humeroscapular contribution and/or the scapulothoracic contribution to the range of motion may include determining one or more posture parameters associated with a posture of the patient. The scapulothoracic contribution may be determined based on one or more landmark characteristics associated with the humerus model, the scapula model and/or the thorax model of the patient. Determining the humeroscapular contribution and/or the scapulothoracic contribution may include performing a range of motion simulation of the humerus model in one or more kinematic planes based on the posture parameter(s). Numerical relationship(s) between the humeroscapular contribution and the scapulothoracic contribution may be determined for at least one or more positions relative to the overall range of motion. A surgical plan associated with the shoulder joint model may be established based on the determined numerical relationship. The surgical plan may include one or more implant parameters such as an implant type, an implant dimension and/or the implant position. The overall range of motion may be determined in response to setting the implant parameters. The surgical plan may be established based on the implant parameter(s). One or more values and/or other indicators associated with the numerical relationship(s) may be displayed in a user interface.

Referring to FIGS. 47-50, with continuing reference to FIGS. 2 and 8, a user interface 1156 is disclosed. An anatomical model 1129 associated with a patient may be displayed in a display window 1160 of the user interface 1156. The anatomical model 1129 may include a scapula bone model 1130S and a humerus bone model 1130H. A glenoid implant model 1132G may be positioned relative to a glenoid of the scapula model 1130S. A humerus implant model 1132H may be positioned relative to a proximal portion of the humerus bone model 1130H. Articulation surfaces of the implant models 1132G, 1132H may be positioned in engagement with each other to establish a joint.

The surgeon or clinical user may interact with the user interface 1156 and/or another portion of the planning system 20 to determine (e.g., evaluate) the range of motion associated with the proposed implant position and/or orientation of the implant model(s) 1132. The surgeon or clinical user may select and position the implant model(s) 1132 to achieve sufficient range of motion based on goals of the patient. The surgeon may perform a tradeoff to achieve the goals. If the proposed implant position may not achieve the acts of daily living goals, then the surgeon or clinical user may adjust the position and/or orientation of the implant model(s) 1132 iteratively until the patient goals may be achieved. Knowing how much humeroscapular and scapulothoracic movement may be achievable may assist the surgeon or clinical user to fine tune the implant position, orientation and/or type to establish a surgical plan 36 for the patient. In scenarios, certain outcomes may only be achievable with a larger implant component (e.g., glenosphere), which may provide more abduction but not necessarily more internal rotation.

The spatial module 50 may be operable to cause the display module 48 to display the scapula and humerus bone models 1130S, 1130H and associated implant models 1132G, 1132H relative to each other based upon a range of motion simulation in the kinematic plane(s) REF-K. The ROM modeler 101 may be operable to perform the range of motion simulation. The surgeon or clinical user may select one or more buttons 1162B or other objects 1162 from a menu 1162M to cause the ROM modeler 101 to perform the range of motion simulation for the associated kinematic motion, such as abduction. Kinematic motion in other plane(s) may be evaluated, such as external rotation.

The surgeon and patient may establish various acts of daily living/lifestyle goals, which may be accessible by the planning environment 28. The planning environment 28 may be operable to determine a cumulative range of motion. The cumulative range of motion may include eight positions (e.g., kinematic movements) defined for the arm. The ROM modeler 101 may be operable to determine a range of motion for each position. The range of motion for some positions may be relatively better than other positions. But, the patient may prioritize some positions over other positions to achieve certain acts of daily living/lifestyle goals. Certain patients may prioritize internal rotation (e.g., to reach a back pocket) over abduction (e.g., to reach a shelf or comb their hair).

Scapulothoracic movement may be utilized to establish a surgical plan 36 for the patient. The determined (e.g., assigned or predicted) scapulothoracic movement and associated contribution to the range of motion may be utilized to adjust or otherwise establish a position and/or orientation of implant model(s) 32 associated with the surgical plan 36. The implant position and/or orientation may be established based on acts of daily living/lifestyle goals of the patient.

Scapulothoracic movement may be incorporated in the planning environment 28 to determine (e.g., predict) post-operative range of motion in one or more kinematic planes. Determining scapulothoracic movement may provide a relatively better prediction of what the post-operative range of motion may be for the patient. The display module 48 may be configured to display in the user interface 1156 how much scapulothoracic movement may contribute to the range of motion for the respective position(s), including the maximum range of motion. The display module 48 may be configured to animate or otherwise display in the display window 1160 movement of the humerus model 1130H and any associated movement of the scapula model 1130S, which may occur in response to the ROM modeler 101.

The range of motion simulation may include motion of the humerus model 1130H based on scapulothoracic movement of the scapula model 1130S. The display module 48 may be operable to display movement of the scapula model 1130S in the display window 1160 during the range of motion simulation of the humerus model 1130H. The display model 48 may be operable to display movement of the humerus model 1130H in the display window 1160 based on the scapulothoracic movement of the scapula model 1130S. The ROM modeler 101 may be operable to perform the range of motion simulation based on any of the factors and/or other patient characteristics disclosed herein, including the scapulothoracic and/or humeroscapular contributions assigned to the anatomical model 1129. The scapulothoracic and/or humeroscapular contributions may be determined utilizing any of the techniques disclosed herein and may be expressed as one or more numerical relationships (e.g., ratios, percentages, etc.). The scapulothoracic contributions for the movements and/or kinematic planes may be the same or may differ from each other.

Scapulothoracic motion may be evaluated to determine range of motion in one or more of the positions. The comparison module 52 may be configured to add a predetermined amount to the humeroscapular-only range of motion based on the determined (e.g., assigned or predicted) amount of scapulothoracic motion. In an implementation, the user interface 1156 may indicate that the patient may achieve 90 degrees of abduction with at least some humeroscapular movement. The comparison module 52 may be configured to add to the humeroscapular motion a predetermined amount associated with scapulothoracic movement (e.g., 30 degrees) to establish an overall range of motion (e.g., 120 degrees). The display module 48 may be configured to display or otherwise communicate the humeroscapular and scapulothoracic range of motion and/or associated contributions in the display window 1160 and/or another portion of the user interface 1156.

The comparison module 52 may be configured to determine one or more numerical relationships between the humeroscapular and scapulothoracic contributions and/or the overall range of motion, including any of the numerical relationships disclosed herein. The display module 48 may be configured to display the numerical relationship(s) in the user interface 1156. The humeroscapular and/or scapulothoracic contributions may be displayed in angular degrees, ratios, percentages, etc.

The display module 48 may be operable to display the numerical relationship(s) between the humeroscapular and scapulothoracic contributions and/or overall range of motion in the display window 1160 and/or another portion of the user interface 1156. The numerical contribution(s) may be displayed by graphic(s) 1162G, such as a set of indicators (e.g., bars, curves) and/or text boxes associated with the respective values. The displayed values may include ratios, percentages, and/or respective amounts. The graphics 1162G may include a set of indicators associated with the humeroscapular contribution 1162HS, scapulothoracic contribution 1162ST and combined value (e.g., summation of the contributions) 1162C for the respective movement. The indicators 116HS, 1162ST, 1162C may be a set of bars associated with the respective values. Each movement may be associated with a respective set of indicators 116HS, 1162ST, 1162C (e.g., indicators 1162G-F, 1162G-E, 1162G-IR, 1162G-ER, 1162G-AB, 1162G-AB, 1162G-AD, etc.), which may be displayed in the user interface 1160. The indicators may be associated with cumulative and/or non-cumulative values for the respective movement.

The comparison module 52 may be operable to assign default values to the respective bone models 1130H, 1130S based on the determined humeroscapular and scapulothoracic contributions. The user interface 1156 may include one or more objects 1162 configured to set the humeroscapular and/or scapulothoracic contributions of the associated humerus model 1130H and/or scapula model 1130S of the respective anatomical model 1129, such as a slider bar or list. In the implementation of FIG. 47, the objects 1162 may include a drop down list 1162L with preselected values (e.g., percentages) for setting the scapular contribution. The ROM modeler 101 may be operable to perform a range of motion simulation in the user interface 1156 based on the selected value(s). The comparison module 52 may be operable to assign (e.g., estimate) default values for the humeroscapular and/or scapulothoracic contributions to the respective bone models 1130H, 1130S for one or more movements based on the determined humeroscapular and scapulothoracic contributions for another movement (e.g., abduction). The assigned scapulothoracic contribution may be based on a preselected ratio of the determined scapulothoracic contribution for the other movement (e.g., abduction). The preselected ratios may be the same or may differ for the movements of the respective bone model 1130H/1130S. In implementations, the comparison module 52 may be operable to assign approximately ⅓ of the value (e.g., ratio of 1:3) of the scapulothoracic contribution for abduction to the scapulothoracic contribution for one or more other movements, such as flexion, extension, internal rotation, external rotation and/or adduction (e.g., approximately 9 degrees scapulothoracic contribution for flexion based on approximately 35 degrees for abduction). Utilizing the techniques disclosed herein, the surgeon or clinical user may be provided with an approximation of the scapulothoracic and/or humeroscapular contributions to the range of motion for one or more movements based on a limited set of imagery and/or simulation utilized to determine the scapulothoracic contribution for another movement (e.g., abduction), which may improve planning to achieve acts of daily living goals of the patient.

In implementations for abduction of the humerus model 1130H, the range of motion of the arm may be associated with approximately 120 degrees of total abduction for an associated implant position. Approximately 90 degrees of the abduction may be associated with humeroscapular movement and/or a combination of humeroscapular and scapulothoracic movement. A balance of the total range of motion (e.g., 30 degrees) may be associated with only scapulothoracic movement. The display module 48 may be configured to display or otherwise communicate values associated with the humeroscapular and scapulothoracic movements with respect to the range of motion in the display window 1160 and/or another portion of the user interface 1156.

The humerus model 1130H of FIG. 47 may be associated with a first (e.g., starting) position of the movement (e.g., abduction). The position associated with FIG. 47 may be associated with approximately 15 degrees of abduction relative to a vertical axis of the patient. The humeroscapular and scapulothoracic contributions may be zero degrees at the starting position. The contribution ratio between the humeroscapular and scapulothoracic contributions may be 1:0 beginning from the starting position (e.g., 0% scapulothoracic). The humerus model 1130H of FIGS. 48-49 may be associated with different (e.g., intermediate) positions of the movement. The position associated with FIG. 48 may be associated with approximately 50 degrees of abduction relative to the starting position. The position associated with FIG. 49 may be associated with approximately 80 degrees of abduction relative to the starting position. The position associated with FIG. 50 may be associated with approximately 105 degrees of abduction relative to the starting position and approximately 120 degrees of abduction relative to a vertical axis of the patient. A range of motion between 0 and 50 degrees may be associated with only humeroscapular movement. The cumulative humeroscapular contribution and scapulothoracic contribution associated with the humerus model 1130H of FIG. 48 may be approximately 50 degrees and approximately 0 degrees, respectively, for an overall movement of approximately 50 degrees relative to the starting position. The contribution ratio may be 1:0 between the positions of the humerus model 1130H associated with FIGS. 47 and 48. A range between 0 degrees and 50 degrees may be associated with only humeroscapular movement (e.g., contribution ratio of 1:0). The display module 48 may be operable to display a current (e.g., intermediate or stopping) position of the humeral bone model 1130H relative to the starting position. An instance of the humeral bone model 1130H' may be displayed in phantom at the starting position (shown in dashed lines in FIGS. 48-50) relative to the position of humerus model 1130H along the range of motion. The humerus model 1130H position may differ from the humerus model 1130H' associated with the starting position.

Figure 49:
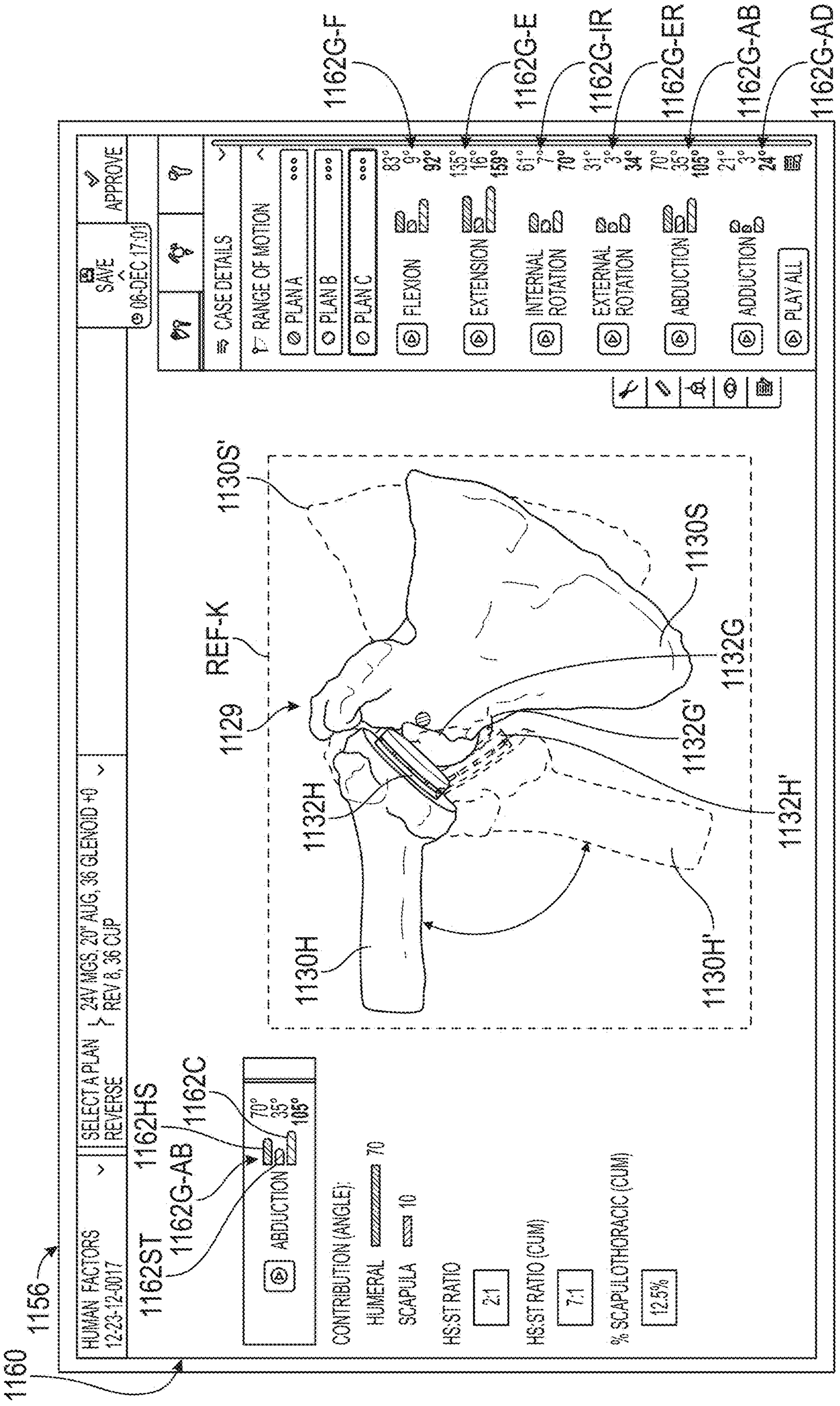

In the implementation of FIG. 49, a combined movement of the humeral model 1130H and scapula model 1132S may contribute to the overall range of motion. The humeral model 1130H may be associated with humeroscapular motion. The humeral model 1130H position may differ from the humeral model 1130H' associated with the starting position. The scapula model 1130S may be associated with scapulothoracic motion. The display module 48 may be operable to display a current (e.g., intermediate or stopping) position of the scapula bone model 1130S relative to the starting position. An instance of the scapula bone model 1130S' may be displayed in phantom at the starting position (shown in dashed lines in FIGS. 49-50). The scapula model 1130S position may differ from the scapula model 1130S' associated with the starting position.

The humeroscapular and scapulothoracic contributions to the range of motion may be assigned to the humeral model 1130H and scapula model 1132S based on any of the techniques disclosed herein. The display window 1160 may be operable to display a position and/or movement of the humeral model 1130H and scapula model 1132S, including relative to the starting positions associated with humeral and scapula models 1130H', 1130S', based on the assigned contributions. A range between 50 degrees and 80 degrees may be associated with a combination of humeroscapular movement and scapulothoracic movement. The cumulative humeroscapular contribution and scapulothoracic contribution associated with FIG. 49 may be approximately 70 degrees and approximately 10 degrees, respectively, for an overall movement of approximately 80 degrees relative to the starting position. The non-cumulative contribution ratio may be 2:1 between the positions associated with FIGS. 48 and 49. The cumulative contribution ratio may be approximately 7:1 (e.g., 12.5% scapulothoracic) at the position associated with FIG. 49.

At the position of the humerus bone model 1130H of FIG. 49, the humerus implant model 1132H may impinge on the glenoid implant model 1132G and/or the scapula model 1132S at an impingement point IP. The impingement may limit relative movement between the humerus and scapula bone models 1130H, 1130G.

Figure 50:
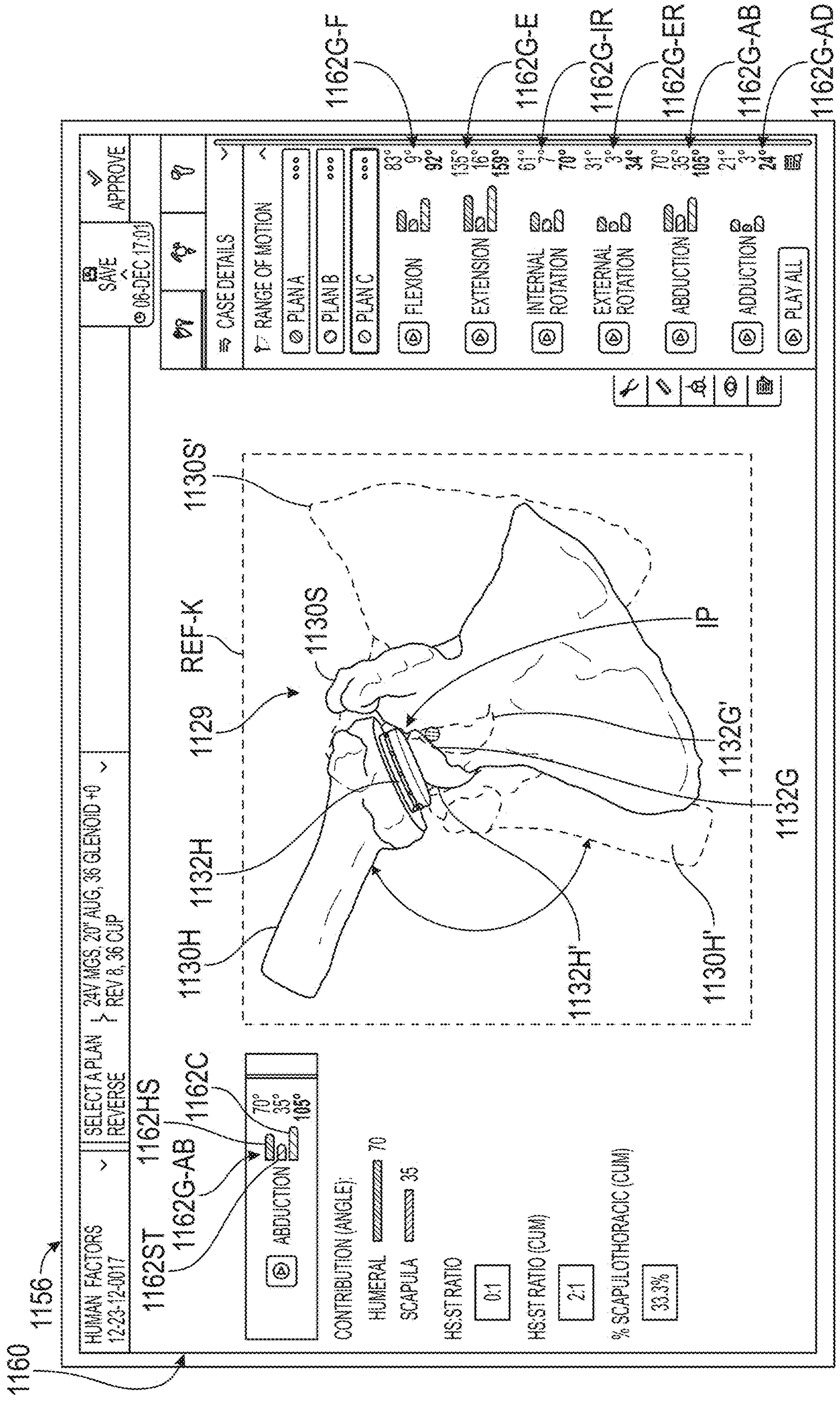

The humerus model 1130H of FIG. 50 may be associated with a second (e.g., stopping) position of the movement. The humeroscapular contribution between the position of FIG. 49 and the position of FIG. 50 may be approximately zero due to the impingement. A range of motion above 75 degrees may be associated with only scapulothoracic movement. The cumulative humeroscapular contribution and scapulothoracic contribution associated with the humerus model 1130H of FIG. 50 may be approximately 70 degrees and approximately 35 degrees, respectively, for an overall movement of approximately 105 degrees relative to the starting position. The cumulative (e.g., overall) contribution ratio may be approximately 2:1 (e.g., 33.3% scapulothoracic) at the position associated with FIG. 50. The non-cumulative contribution ratio between the positions associated with FIGS. 49 and 50 may be 0:1 (e.g., 100% scapulothoracic).

The surgeon or clinical user may interact with the user interface 1156 to adjust a position and/or orientation of the implant model(s) 1130, including subsequent to display of the range of motion simulation in the display window 1160. The surgeon or clinical user may interact with the user interface 1156 to cause the range of motion simulation to execute based on the adjusted position(s) and/or orientation(s). The surgeon or clinical user may approve a surgical plan 36 based on the range of motion simulation(s), humeroscapular and/or scapulothoracic contribution(s), and/or other information communicated by the user interface 1156.

The planning environment 28 may be operable to establish a patient-specific implant design based on the determined scapulothoracic movement and/or associated contribution. The implant design may include various parameters, including size, shape and/or porosity. The porosity may be determined based on various characteristics of the anatomy, including bone quality. The implant design may be associated with an implant model 32 and/or surgical plan 36.

The proposed surgical planning systems and methods of this disclosure may be utilized to create and implement surgical plans that are tailored to the individual patient, which may improve healing. The disclosed systems and methods may reduce complexity in implementing the surgical plans, including reduced packaging and instrumentation. In certain implementations, the system and methods may utilize feedback loops for continuously improving the recommendations provided when developing surgical plans. Range of motion of an arm of the patient may be evaluated based on scapulothoracic contribution, which may be utilized to determine implant characteristics to achieve acts of daily living. The proposed systems and methods therefore provide improved functionality compared to prior planning systems.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A surgical planning system for performing an orthopaedic procedure comprising:

one or more processors operably coupled to memory;

wherein the memory is configured to store a plurality of three-dimensional bone models associated with one or more bones, and the plurality of bone models include a humerus model, a scapula model, and a thorax model associated with a patient, the humerus model and the scapula model associated with a shoulder joint model, and the scapula model and the thorax model associated with a scapulothoracic joint model; and wherein the one or more processors are collectively operable to execute a planning environment, and the planning environment is operable to:

position at least one implant model relative to the shoulder joint model;

determine an overall range of motion of the humerus model relative to one or more kinematic planes based on the position of the at least one implant model, the overall range of motion based on a humeroscapular contribution of humeroscapular movement between the humerus model and the scapula model and a scapulothoracic contribution of scapulothoracic movement between the scapula model and the thorax model;

determine a numerical relationship between the humeroscapular contribution and the scapulothoracic contribution for at least one position relative to the overall range of motion;

establish a surgical plan associated with the overall range of motion based on the numerical relationship; and generate a range of motion indicator including a graphical representation of predicted range of motion data based on the numerical relationship between the humeroscapular contribution and the scapulothoracic contribution, and update the graphical representation in response to repositioning the at least one implant model relative to the shoulder joint model.

2. The surgical planning system as recited in claim 1, wherein the planning environment is operable to:

display the numerical relationship in a user interface.

3. The surgical planning system as recited in claim 1, wherein the planning environment is operable to:

determine one or more soft tissue insertion points along the scapula model and/or the humerus model; and determine an amount of the scapulothoracic movement based the one or more soft tissue insertion points.

4. The surgical planning system as recited in claim 1, wherein the planning environment is operable to:

receive image data associated with the patient; and generate the scapula, thorax and humerus models based on the image data.

5. The surgical planning system as recited in claim 1, wherein the numerical relationship includes a contribution ratio between the humeroscapular contribution and the scapulothoracic contribution, and the planning environment is operable to:

determine the contribution ratio for a set of positions relative to the overall range of motion, the set of positions including a first position associated with commencement of the scapulothoracic contribution and a second position associated with a maximum limit relative to the overall range of motion, and the contribution ratio associated with the first position differs from the contribution ratio associated with the second position; and display the contribution ratio for the set of positions relative to the overall range of motion.

6. The surgical planning system as recited in claim 1, wherein the planning environment is operable to:

determine an amount of the scapulothoracic movement based on one or more posture parameters associated with a posture of the patient.

7. The surgical planning system as recited in claim 6, wherein:

the one or more posture parameters include a scapular angle associated with a scapula.

8. The surgical planning system as recited in claim 6, wherein:

the one or more posture parameters include a set of posture types, each of the posture types associated with a discrete range of scapular angles.

9. The surgical planning system as recited in claim 6, wherein the planning environment is operable to:

determine a starting position of the humerus model and a starting position of the scapula model based on the one or more posture parameters; and determine the humeroscapular contribution based on the starting position of the humerus model and determine the scapulothoracic contribution based on the starting position of the scapula model.

10. The surgical planning system as recited in claim 1 wherein:

the three-dimensional bone models include one or more bone models associated with one or more bones of a representative patient population; and the planning environment is operable to determine the scapulothoracic movement in response to comparing the scapula model and the thorax model of the patient to a representative scapula model and a representative thorax model of another patient of the representative patient population.

11. The surgical planning system as recited in claim 10, wherein the planning environment is operable to:

select the representative scapula model in response to analyzing the representative patient population within a statistical shape model.

12. The surgical planning system as recited in claim 1, wherein the planning environment is operable to:

determine an amount of the scapulothoracic movement based on one or more landmark characteristics associated with the humerus model, the scapula model, and/or the thorax model; and assign the scapulothoracic contribution based on the determined amount of the scapulothoracic movement.

13. The surgical planning system as recited in claim 12, wherein the one or more landmark characteristics comprise:

an amount of lateralization of an acromion associated with the scapula model;

an amount of curvature of an angulus inferior associated with the scapula model;

a collapsed condition of the humerus model with respect to a premorbid boundary; and/or a broken gothic arch condition associated with a position of the humerus model relative to the scapula model.

14. A surgical planning system for performing an orthopaedic procedure comprising:

one or more processors operably connected to memory;

wherein the memory is operable to store a plurality of three-dimensional bone models associated with respective bones of a representative patient population, and the plurality of bone models include a first set associated with a scapula, a second set associated with a thorax, and a third set associated with a humerus; and wherein the one or more processors are collectively operable to execute a planning environment, and the planning environment is operable to:

select a representative scapula model from the first set of the bone models in response to comparing the representative scapula model to a patient scapula model associated with the scapula of a patient, wherein the representative scapula model is associated with a representative thorax model of the second set of the bone models, the patient scapula model and a patient thorax model establish a first spatial relationship, and the representative scapula and thorax models establish a second spatial relationship;

determine a range of motion of a patient humerus model associated with a humerus of the patient model relative to one or more kinematic planes in response to comparing the first and second spatial relationships; and generate a range of motion indicator including a graphical representation of predicted range of motion data determined from the comparison of the first and second spatial relationships, and display the first spatial relationship between the patient scapula model and the patient thorax model in a user interface.

15. The surgical planning system as recited in claim 14, wherein the planning environment is operable to:

position at least one implant model relative to the patient scapula model and/or the patient humerus model; and determine the range of motion of the humerus model based on the position of the at least one implant model.

16. The surgical planning system as recited in claim 14, wherein the range of motion is an overall range of motion of the patient humerus model relative to the one or more kinematic planes, and the planning environment is operable to:

determine the overall range of motion based on a humeroscapular contribution of humeroscapular movement between the patient humerus model and the patient scapula model and a scapulothoracic contribution of scapulothoracic movement between the patient scapula model and the patient thorax model; and determine a numerical relationship between the humeroscapular contribution and the scapulothoracic contribution for at least one position relative to the overall range of motion.

17. The surgical planning system as recited in claim 14, wherein the planning environment is operable to:

select the representative scapula model in response to analyzing the representative patient population within a statistical shape model.

18. The surgical planning system as recited in claim 17, wherein:

the planning environment is operable to:

create a plurality of anatomical makeup classifications based on a plurality of predefined modes within the statistical shape model that characterize anatomical differences within the representative patient population and a plurality of standard deviations of anatomical variances contained within each of the plurality of predefined modes; and assign the anatomical makeup classifications to the bone models; and the memory is operable to store the anatomical makeup classifications.

19. The surgical planning system as recited in claim 18, wherein the planning environment is operable to:

select the representative scapula model in response to varying one or more of the predefined modes.

20. The surgical planning system as recited in claim 18, wherein:

the predefined modes include a posture mode associated with posture; and the planning environment is operable to:

assign the anatomical makeup classifications to the bone models based on the posture mode;

determine one or more posture parameters associated with a posture of the patient based on the anatomical makeup classification associated with the representative scapula model and/or the representative thorax model; and determine the range of motion based on the one or more posture parameters.

* * * * *